US009011857B2

(12) United States Patent
Braun et al.

(10) Patent No.: US 9,011,857 B2
(45) Date of Patent: *Apr. 21, 2015

(54) METHODS OF TREATING CANCER BY ADMINISTERING EMP2 ANTIBODIES

(71) Applicant: The Regents of The University of California, Oakland, CA (US)

(72) Inventors: Jonathan Braun, Tarzana, CA (US); Lynn K. Gordon, Tarzana, CA (US); Kaori Shimazaki, Los Angeles, CA (US); Madhuri Wadehra, Manhattan Beach, CA (US); Kathy A. Kelly, Pacific Palisades, CA (US); Anna M. Wu, Sherman Oaks, CA (US)

(73) Assignee: The Regents of The University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/684,901

(22) Filed: Nov. 26, 2012

(65) Prior Publication Data

US 2013/0230527 A1 Sep. 5, 2013

Related U.S. Application Data

(63) Continuation of application No. 12/682,032, filed as application No. PCT/US2008/079244 on Oct. 8, 2008, now Pat. No. 8,318,906, and a continuation-in-part of application No. 11/868,788, filed on Oct. 8, 2007, now Pat. No. 8,648,052, which is a continuation-in-part of application No. PCT/US2006/014238, filed on Apr. 14, 2006.

(60) Provisional application No. 60/671,755, filed on Apr. 15, 2005.

(51) Int. Cl.
| | |
|---|---|
| *A61K 39/00* | (2006.01) |
| *A61K 39/395* | (2006.01) |
| *C07K 16/30* | (2006.01) |
| *C07K 16/12* | (2006.01) |
| *C07K 16/28* | (2006.01) |
| *A61K 45/06* | (2006.01) |

(52) U.S. Cl.
CPC ............ *C07K 16/30* (2013.01); *A61K 39/39558* (2013.01); *C07K 16/125* (2013.01); *C07K 16/28* (2013.01); *A61K 45/06* (2013.01); *C07K 2316/96* (2013.01); *C07K 2317/21* (2013.01); *C07K 2317/622* (2013.01); *C07K 2317/73* (2013.01); *C07K 2319/00* (2013.01); *C07K 2317/52* (2013.01)

(58) Field of Classification Search
CPC .................. A61K 39/39558; A61K 2039/505; A61K 2121/00; C07K 16/2863; C07K 2317/21; C07K 2317/24; C07K 2317/626; C07K 2317/76
See application file for complete search history.

(56) References Cited

U.S. PATENT DOCUMENTS

| | | |
|---|---|---|
| 5,264,188 A | 11/1993 | Lew |
| 5,270,163 A | 12/1993 | Gold et al. |
| 5,288,514 A | 2/1994 | Ellman |
| 5,475,096 A | 12/1995 | Gold et al. |
| 5,506,337 A | 4/1996 | Summerton et al. |
| 5,519,134 A | 5/1996 | Acevedo et al. |
| 5,525,735 A | 6/1996 | Gallop et al. |
| 5,539,083 A | 7/1996 | Cook et al. |
| 5,549,974 A | 8/1996 | Holmes |
| 5,569,588 A | 10/1996 | Ashby et al. |
| 5,593,853 A | 1/1997 | Chen et al. |
| 5,786,362 A | 7/1998 | Krongrad |
| 6,413,245 B1 | 7/2002 | Yaacobi et al. |
| 6,506,781 B1 | 1/2003 | Cobb et al. |
| 6,750,015 B2 | 6/2004 | Horwitz et al. |
| 6,794,378 B2 | 9/2004 | Iino et al. |
| 7,229,770 B1 | 6/2007 | Price et al. |
| 7,288,531 B2 | 10/2007 | Pal et al. |
| 7,304,042 B2 | 12/2007 | Pal et al. |
| 7,345,027 B2 | 3/2008 | Tolentino et al. |
| 7,504,385 B2 | 3/2009 | Binetti et al. |
| 7,511,025 B2 | 3/2009 | Wyatt et al. |
| 7,517,865 B2 | 4/2009 | Meyers |
| 7,521,431 B2 | 4/2009 | Reich et al. |
| 7,585,848 B2 | 9/2009 | Masuda et al. |
| 7,592,325 B2 | 9/2009 | Jimenez et al. |

(Continued)

FOREIGN PATENT DOCUMENTS

| | | |
|---|---|---|
| EP | 0430539 A2 | 6/1991 |
| EP | 0488401 A1 | 6/1992 |

(Continued)

OTHER PUBLICATIONS

Abrami, L. et al., "Cross-talk between Caveolae and Glycosylphosphatidylinositol-rich Domains", *Journal of Biological Chemistry*, vol. 276, No. 33, pp. 30729-30736 (2001).

Agrawal et al., "Antisense therapeutics: is it as simple as complementary base recognition?" *Molecular Medicine Today*, vol. 6, pp. 72-81 (2000).

Amarzguioui, M. et al., "An algorithm for selection of functional siRNA sequences," *Biochemical and Biophysical Research Communications*, 316:1050-1058 (2004).

Anderson, E.M. et al., "Experimental validation of the importance of seed complement frequency to SiRNA specificity," *RNA*, 14:853-861 (2008).

(Continued)

*Primary Examiner* — Robert Landsman
(74) *Attorney, Agent, or Firm* — Morgan, Lewis & Bockius LLP; Annette S. Parent

(57) ABSTRACT

The present invention provides methods and compositions useful in the treatment or prevention of *Chlamydia* infections and cancer. The methods and compositions inhibit the entry of *Chlamydia* into a host cell expressing EMP2 by interfering with the interaction between the *Chlamydia* and EMP2. The methods and compositions target cancers which express or overexpress EMP2 nucleic acids and polypeptides by targeting EMP2.

6 Claims, 26 Drawing Sheets

(56) References Cited

U.S. PATENT DOCUMENTS

| | | | |
|---|---|---|---|
| 7,629,323 | B2 | 12/2009 | Surmeier et al. |
| 7,638,482 | B2 | 12/2009 | LaVallie et al. |
| 2003/0228305 | A1 | 12/2003 | Frantz et al. |
| 2004/0175385 | A1 | 9/2004 | Marks et al. |
| 2005/0244463 | A1 | 11/2005 | Huang et al. |
| 2006/0062785 | A1 | 3/2006 | Freson et al. |
| 2007/0065889 | A1 | 3/2007 | Roberts et al. |
| 2013/0004493 | A1 | 1/2013 | Gordon et al. |

FOREIGN PATENT DOCUMENTS

| | | |
|---|---|---|
| WO | WO 91/19735 | 12/1991 |
| WO | WO 91/19813 | 12/1991 |
| WO | WO 92/00091 | 1/1992 |
| WO | WO 93/20242 | 10/1993 |
| WO | WO 03/057160 | 7/2003 |
| WO | WO 2005/055808 | 6/2005 |
| WO | WO 2006/094014 | 9/2006 |
| WO | WO 2009/048980 | 4/2009 |
| WO | WO 2011/063161 | 5/2011 |

OTHER PUBLICATIONS

Bersinger, N.A., et al., "Production of endometrial placental protein 14 and prolactin by cultured endometrial explants after collagenase and freeze/thaw treatment, and in response to progesterone", *Early Pregnancy: Biology and Medicine*, vol. 1, pp. 134-140 (1995).

Birmingham, A. et al., "3' UTR seed matches, but not overall identity, are associated with RNAi off-targets," *Nature Methods*, 3(3):199-204 (2006).

Carey, A.J. and Beagley, K.W., "*Chlamydia trachomatis*, a Hidden Epidemic: Effects on Femal Reproduction and Options for Treatment", *Am. J. Reprod. Immunol.*, Abstract only (2010).

Chen, Y. et al., "RNAi for Treating Hepatitis B Viral Infection", *Pharmaceutical Research*, vol. 25, No. 1, pp. 72-86 (2008).

Colman, "Effects of amino acid sequence changes on antibody-antigen interactions" *Research in Immunology*, vol. 145, pp. 33-36 (1994).

Cui, W. et al., "OptiRNAi, an RNAi design tool," *Computer Methods and Programs in Biomedicine*, 75:67-73 (2004).

Delevoye, C. et al., "SNARE Protein Mimicry by an Intracellular Bacterium", *PLOS Pathogens*, vol. 4, Issue 3, (2008).

Dudek, P., et al., TROD: T7 RNAi Oligo Designer, *Nucleic Acids Research* 32:W121-W123 (2004).

Elbashir, S.M. et al., "Analysis of gene function in somatic mammalian cells using small interfering RNAs," *Methods* 26:199-213 (2002).

Flynn, M. A. et al., Efficient delivery of small interfering RNA for inhibition of IL-12p40 expression in vivo, *Journal of Inflammation* 1:4 (2004).

Ge, Q. et al., "Use of siRNAs to prevent and treat influenza virus infection", *Virus Research*, vol. 102, pp. 37-42 (2004).

Gura, "Systems for Identifying New Drugs Are Often Faulty" *Science*, vol. 278, pp. 1041-1042 (1997).

Henschel, A. et al., "DEQOR: a web-based tool for the design and quality control of siRNAs, *Nucleic Acids Research* 32:W113-W120 (2004).

Hsieh, A. C. et al., "A library of siRNA duplexes targeting the phosphoinositide 3-kinase AT pathway: determinants of gene silencing for use in cell-based screens," *Nucleic Acids Research* 32(3):893-901 (2004).

Jackson, A. L., et al., "Position-specific chemical modification of siRNAs reduces 'off- target' transcript silencing," *RNA* 12:1197-1205 (2006).

Jain, "Barriers to Drug Delivery in Solid Tumors" *Scientific American*, July, pp. 58-65 (1994).

Jen et al., "Suppression of Gene Expression by Targeted Disruption of Messenger RNA: Available Options and Current Strategies" *Stem Cells*, vol. 18, pp. 307-319 (2000).

Kim, B. et al., Inhibition of Ocular Angiogenesis by siRNA Targeting Vascular Endothelial Growth Factor Pathway Genes, *American Journal of Pathology* 165(6):2177-2185 (2004).

Lane, B. Josh et al., "Chlamydial Entry Involves TARP Binding of Guanine Nucleotide Exchange Factors", *PLOS Pathogens*, vol. 4, Issue 3 (2008).

Leitinger and Hogg, "The involvement of lipid rafts in the regulation of integrin function", *Journal of Cell Science*, vol. 115, pp. 963-972 (2002).

Levenkova, N. et al., "Gene specific siRNA selector," *Bioinformatics* 20(3): 430-432 (2004).

Luo, K. Q. et al., "The gene-silencing efficiency of siRNA is strongly dependent on the local structure of mRNA at the targeted region," *Biochemical and Biophysical Research Communications* 318:303-310 (2004).

Ma, Z. et al., Cationic lipids enhance siRNA-mediated interferon response in mice, *Biochemical and Biophysical Research Communications* 330:755-759 (2005).

Melkonian, K., et al., "Role of Lipid Modifications in Targeting Proteins to Detergent-resistant Membrane Rafts", *The Journal of Biological Chemistry*, vol. 274, No. 6, pp. 3910-3917 (1999).

Milhavet, O. et al., "RNA Interference in Biology and Medicine," *Phamacol Rev* 55:629-648 (2003).

Moffett, S. et al., "Lipid-dependent Targeting of G Proteins into Rafts", *The Journal of Biological Chemistry*, vol. 275, No. 3, pp. 2191-2198 (2000).

Mohan et al., "Characterization of the Epithelial Membrane Protein 2 in the Progression of Endometrial Adenocarcinoma" *Modem Pathology*, Jan. 18 (Supp.1), p. 196A (2005).

Morales, S.A. et al., "FAK Activation and the Role of Epithelial Membrane Protein 2 (EMP2) in Collagen Gel Contraction", *Investigative Ophthalmology & Visual Science*, vol. 50, No. 1, pp. 462-469 (2009).

Morales, S. A., "Functional Consequences of Interactions between FAK and Epithelial Membrane Protein 2 (EMP2)," *IOVS*, 50(10):4949-4956 (2009).

Morrissey, D. V. et al., "Activity of Stabilized Short Interfering RNA in a Mouse Model of Hepatitis B Virus Replication," *Hepatology* 41(6):1349-1356 (2005).

Morrissey, D. V. et al., Potent and persistent in vivo anti-HBV activity of chemically modified siRNAs, *Nature Biology* 23(8):1002-1007 (2005).

MSNBC News Services, "Mixed results on new cancer drug" Nov. 9, pp. 1-4 (2000).

Naito, Y. et al., "siDirect: highly effective, target-specific siRNA design software for mammalian RNA interference," *Nucleic Acids Research*, 32:W124-W129 (2004).

Nichols, B. et al., "Rapid Cycling of Lipid Raft Markers between the Cell Surface and Gogli Complex", *The Journal of Cell Biology*, vol. 153, No. 3, pp. 529-541 (2001).

Niu et al., "Restricted expression pattern of the putative tumor suppressor gene, Epithelial Membrane Protein 2 in the eye" *Invest Ophthalmol Vis. Sci.* E-Abstract 2419 (2002).

Opalinska et al., "Nucleic-Acid Therapeutics: Basic Principles and Recent Applications" *Nature Reviews Drug Discovery*, vol. 1, pp. 503-514 (2002).

Pancoskca, P. et al., "Efficient RNA interference depends on global context of the target BF sequence: quantitative analysis of silencing efficiency using Eulerian graph representation of siRNA," *Nucleic Acids Research*, 32(4):1469-1479 (2004).

Pareek et al., "Detection and Processing of Peripheral Myelin Protein PMP22 in Cultured Schwann Cells" *Journal Biol. Chemistry*, vol. 268, No. 14, pp. 10372-10379 (1993).

Paul, Ed., "Fv Structure and Diversity in Three Dimensions" *Fundamental Immunology, Third Edition*, Raven Press, New York, Chapter 8, pp. 292-295 (1993).

Reich, S. J. et al., "Small interfering RNA (siRNA) targeting VEGF effectively inhibits ocular neovascularization in a mouse model," *Molecular Vision*, 9:210-216 (2003).

Reynolds, A. et al., "Rational siRNA design for RNA interference," *Nature Biology* 22(3):326-330 (2004).

Rossi, J.J. et al., "A practical siRNA microbicide?" *Gene Therapy*, vol. 13, pp. 1493-1494 (2006).

Rudikoff et al., "Single amino acid substitution altering antigen-binding specificity" *Proc. Natl. Acad. Sci.*, vol. 79, No. 6, pp. 1979-1983 (1982).

(56) References Cited

OTHER PUBLICATIONS

Schiffelers, R. M. et al., "Cancer siRNA therapy by tumor selective delivery with ligand-targeted sterically stabilized nanoparticle," *Nucleic Acids Research*, 32(19):e149 (2004).
Schubert, S. et al., "Local RNA Target Structure Influences siRNA Efficacy: Systematic Analysis of Intentionally Designed Binding Regions", *J. Mol. Biol.*, vol. 348, pp. 883-893 (2005).
Shimazaki, K. et al., "Blockade of epithelial membrane protein 2 (EMP2) abrogates infection of *Chlamydia muridarum* murine genital infection model," *FEMS Immunol Med Microbiol* 1-10 (2008).
Shimazaki, K. et al., Epithelial membrane protein 2 modulates infectivity of *Chlamydia muridarum* (MoPn), *Microbes and Infection* 9:1003-1010 (2007).
Shimazaki et al., "Diabodies Targeting Epithelial Membrane Protein 2 Reduce Tumorigencity of Human Endometrial Cancer Cell Lines" *Clin. Cancer Res.*, vol. 14, No. 22, pp. 7367-7377 (2008).
Soutschek, J. et al., "Therapeutic silencing of an endogenous gene by systemic administration of modified siRNAs," *Nature*, 432:173-178 (2004).
Swanson, K. et al., "*Chlamydia trachomatis* Species-Specific Induction of Ezrin Tyrosine Phosphorylation Functions in Pathogen Entry", *Infection and Immunity*, vol. 75, No. 12, pp. 5669-5677 (2007).
Takasaki, S. et al., "An Effective Method for Selecting siRNA Target Sequences in Mammalian Cells," *Cell Cycle* 3(6):790-795 (2004).
Taxman, D. J. et al., "Criteria for effective design, construction, and gene knockdown by shRNA vectors," *BMC Biotechnology* 6:7 (2006).
Taylor et al., "Epithelial membrane protein-2 and epithelial membrane protein-3: two novel members of the peripheral myelin protein 22 gene family" *Gene*, vol. 175, pp. 115-120 (1996).
Ui-Tei, K. et al., "Guidelines for the selection of highly effective siRNA sequences for mammalian and chick RNA interference," *Nucleic Acids Research* 32(3):936-948 (2004).
Verma, U. N. et al., "Small Interfering RNAs Directed against β-Catenin Inhibit the in Vitro and in Vivo Growth of Colon Cancer Cells," Clinical Cancer Research, 9:1291- 1300 (2003).
Wadehra, M. et al., "The Tetraspan Protein Epithelial Membrane Protein-2 Interacts with $β_1$ Integrins and Regulates Adhesion", *The Journal of Biological Chemistry*, vol. 277, pp. 41094-41100 (2002).
Wadehra, M. et al., "Characterization of the Biology and Pathobiology of Epithelial Membrane Protein-2", University of California Los Angeles Dissertation, ProQuest Information and Learning Company, Ann Arbor Michigan (2002).
Wadehra, M. et al., "Epithelial membrane protein-2 is expressed in discrete anatomical regions of the eye", *Experimental and Molecular Pathology*, vol. 74, Issue 2, pp. 106-112 (2003).
Wadehra, M. et al., "The tetraspan protein EMP2 increases surface expression of class I major histocompatibility complex proteins and susceptibility to CTL-mediated cell death", *Clinical Immunology*, vol. 107, pp. 129-136 (2003).
Wadehra, M. et al., "The Tetraspan Protein EMP2 Modulates the Surface Expression of Caveolins and Glycosylphosphatidyl Inositol-linked Proteins", *Molecular Biology of the Cell*, vol. 15, pp. 2073-2083 (2004).
Wadehra, M. et al., "Epithelial membrane protein-2 regulates surface expression of alphavbeta3 integrin in the endometrium", *Developmental Biology*, vol. 287, Issue 2, pp. 336-345 (2005).
Wadehra, M. et al., "Expression of Epithelial Membrane Protein-2 is Associated with Endometrial Adenocarcinoma of Unfavorable Outcome", *Cancer*, vol. 107(1): pp. 90-98 (2006).
Wang, C. et al., "Epithelial membrane protein 2,a 4-transmembrane protein that suppresses B-ceillymphoma tumorigenicity," *Blood*, 97(12):3890-3895 (2001).
Wang, L., et al., "A Web-based design center for vector-based siRNA and siRNA cassette," *Bioinformatics* 20( 11 ): 1818-1820 (2004).
Xia, H. et al., "siRNA-mediated gene silencing in vitro and in vivo," *Nature Biotechnology*, 20:1006-1010 (2002).

Yano, J. et al., "Antitumor Activity of Small Interfering RNA/ Cationic Liposome Complex in Mouse Models of Cancer," *Clinical Cancer Research* 10:7721-7726 (2004).
Yuan, B. et al., "siRNA Selection Server: an automated siRNA oligonucleotide prediction server," *Nucleic Acids Research*, 32:W130-W134 (2004).
Zhang, Y. et al., "Intravenous RNA Interference Gene Therapy Targeting the Human Epidermal Growth Factor Receptor Prolongs Survival in Intracranial Brain Cancer," *Clinical Cancer Research*, 10:3667-3677 (2004).
Altshul, S. et al., "Basic Local Alignment Tool", *J. Mol. Biol.*, 215:403-410 (1990).
Altschul, S. et al., "Gapped BLAST and PSI-BLAST: a new generation of protein database search programs", *Nucleic Acids Research*, 25:17 3389-3402 (1997).
Ambati, J., et al. "Age-related macular degeneration: etiology, pathogenesis, and therapeutic strategies." *Surv Ophthalmol.* 48:257-293 (2003).
Batzer, M. et al., "Enhanced evolutionary PCR using oligonucleotides with inosine at the 3'-terminus", *Nucleic Acids Res.*, 19:18 5081 (1991).
Campbell et al., "Phosphate Ester Synthesis Using a Modified Mitsunobu Condensation", *J. Org. Chem.*, 59: 658 (1994).
Cho, C. et al., "An unnatural biopolymer", *Science* 261: 1303 (1993).
Connolly, D. et al., "Tumor vascular permeability factor stimulates endothelial cell growth and angiogenesis", J. Clin. Invest. 84: 1470-1478 (1989).
Connolly, D. et al., "Human vascular permeability factor. Isolation from U937 cells", J. Biol. Chem., 264: 20017-20024 (1989).
De Witt, S. Hobbs et al., "'Diversomers': An approach to nonpeptide, nonoligomeric chemical diversity", *Proc. Natl., Acad. Sci. USA*, 90: 6909-6913 (1993).
Dufner, P. et al., "Harnessing phage and ribosome display for antibody optimisation", *Trends in Biotechnology*, vol. 24: No. 11, pp. 523-529 (2006).
Dvorak, H.F., "Tumors: wounds that do not heal. Similarities between tumor stroma generation and wound healing", *N. Engl. Journ. Med.*, 315: 1650-1659 (1986).
Friedlander, M. et al., "Definition of Two Angiogenic Pathways by Distict $α_v$ Integrins", Science, vol. 270, pp. 1500-1502 (1995).
Gerhardinger et al., "Expression of vascular endothelial growth factor in the human retina and in nonproliferative diabetic retinopathy", *Am. J. Pathol.* 152: 1453-1462 (1998).
Hagihara, M. et al., "Vinylogous polypeptides: an alternative peptide backbone", *J. Am. Chem. Soc.*, 114: 6568 (1992).
Henikoff S. and Henikoff, J., "Amino acid substitution matrices from protein blocks", *Proc. Natl., Acad. Sci., USA*, 89: 10915-10919 (1992).
Hirschmann, R. et al., "Nonpeptidal peptidomimetics with beta-D-glucose scaffolding. A partial somatostatin against bearing a close structural relationship to a potent, selective substance P antagonist." *J. Am. Chem. Soc.*, 114: 9217-9218 (1992).
Hughes, L. and Maurice, D., "A Fresh Look at Iontophoresis", Arch Ophthalmol, vol. 102, pp. 1825-1829 (1984).
Husain, D. et al. "Photodynamic therapy and digital angiography of experimental iris neovascularization using liposomal benzoporphyrin derivative", *Opthamology* 104: 1242-12450 (1997).
Kim, I. et al., "Constitutive expression of VEGF, VEGFR-1, and VEGFR-2 in normal eyes", *Invest. Opthalmol. Vis. Sci.* 40: 2115-2121 (1999).
Kliffen, M. et al., "Increased expression of angiogenic growth factors in age-related maculopathy", Br. J Opthalmol. 81: 154-162 (1997).
Kvanta, A. et al., "Subfoveal fibrovascular membranes in age-related macular degeneration express vascular endothelial growth factor", *Invest. Opthalmol. Vis. Sci.* 37: 1929-1934 (1996).
Lee, V. H. L. et al., "Review: Topical Ocular Drug Delivery: Recent Developments and Future Challenges", *Journal of Ocular Pharmacology*, vol. 2, No. 1, pp. 67-108 (1986).
Leung, D.W. et al., "Vascular endothelial growth factor is a secreted angiogenic mitogen", *Science* 246:1306-1309 (1989).
Liang et al. "Parallel Synthesis and Screening of a Solid Phase Carbohydrate Library," *Science* 274:1520-1522 (1996).

(56) References Cited

OTHER PUBLICATIONS

Lopez, P. et al., "Transdifferentiated retinal pigment epithelial cells are immunoreactive for vascular endothelial growth factor in surgically excised age-related macular degeneration-related choroidal neovascular membranes", *Invest. Opthalmol. Vis. Sci.* 37: 855-868 (1996).

McCafferty, J. et al., "Phage antibodies: filamentous phage displaying antibody variable domains", *Nature*, 348: 552-554 (1990).

McConnell, V. et al., "Assessment of a putative locus for exudative age-related macular degeration on chromosome 16p", *J. Med. Genet.* 41: Supplement 1 (2004).

Miller, J.W. et al., "Vascular endothelial growth factor in ocular neovascularization and proliferative diabetic retinopathy", *Diabetes Metab. Rev.* 13: 37-50 (1997).

Morales, S. et al., "FAK Activation and the Role of Epithelial Membrane Protein 2 (EMP2) in Collagen Gel Contraction", IOVS, 50: 462-469 (2009).

Morales, S. et al., "Epithelial Membrane Protein 2 Controls VEGF Expression in ARPE-19 Cells", *IVOS*, 54: 2367-2372 (2013).

Ohtsuka, E. et al., "An Alternative Approach to Deoxyoligonucleotieds as Hybridization Probes by Insertion of Deoxyinosine at Ambiguous Codon Positions", *The Journal of Biol. Chem.*, 260:5 2605-2608 (1985).

Olsen, T.W. et al., "Human scleral permeability. Effects of age, cryotherapy, transscleral diode laser, and surgical thinning", Invest. Ophthalmol. Vis. Sci. 36: 1893-1903 (1995).

Plouet, J. et al., "Isolation and characterization of a newly identified endothelial cell mitogen produced by AtT-20 cells", EMBO J., 8:3801-3806 (1989).

Rossolini, G. et al., "Use of deoxyinosine-containing primers vs degenerate primers for polymerase chain reaction based on ambiguous sequence information", *Mol. Cell. Probes*, 8:91-98 (1994).

Sathish, J. et al. "Challenges and approaches for the development of safer immunomodulatory biologics", *Nature Reviews*, vol. 12, pp. 306-324 (2013).

Schwesinger, C. et al., "Intrachoroidal neovascularization in transgenic mice overexpressing vascular endothelial growth factor in the retinal pigment epithelium", Am. J. Pathol. 158: 1161-1172 (2001).

Sorbera, L.A. et al. "Treatment of Age-Related Macular Degeneration Humanized Monoclonal Anti-VEGF Antibodiy Angiogenesis Inhibitor", *Drugs of the Future*, 28: 541-545 (2003).

Sundaresan, G. et al., "$^{124}$I-Labeled Engineered Anti-CEA Minibodies and Diabodies Allow High-Contrast, Antigen-Specific Small-Animal PET Imaging of Xenografts in Athymic Mice", *Journal of Nuclear Medicine*, 44:12, 1962-1969 (2003).

Vaughan et al. "Human Antibodies with Sub-nanomolar Affinities Isolated from a Large Non-immunized Phage Display Library," *Nature Biotechnology* 14(3):309-314 (1996).

Witte, L. et al., "Monoclonal antibodies targeting the VEGF receptor-2 (Flk1/KDR) as an anti-angiogenic theraeutic strategy", *Cancer and Metatasis Review*, 17: pp. 155-161 (1998).

Wu, A. and Senter, P., "Arming antibodies: prospects and challenges for immunoconjugates", *Nature Biotech*, 23:1, 1137-1146 (2005).

Yi, X. et al., "Vascular endothelial growth factor expression in choroidal neovascularization in rats", *Graefes Arch Clin Exp Opthalmol* 235: 313-319 (1997).

Yu, L. et al., "Interaction between Bevacizumab and Murine VEGF-A: A Reassessment", *IVOS*, 49:2, pp. 522-527 (2008).

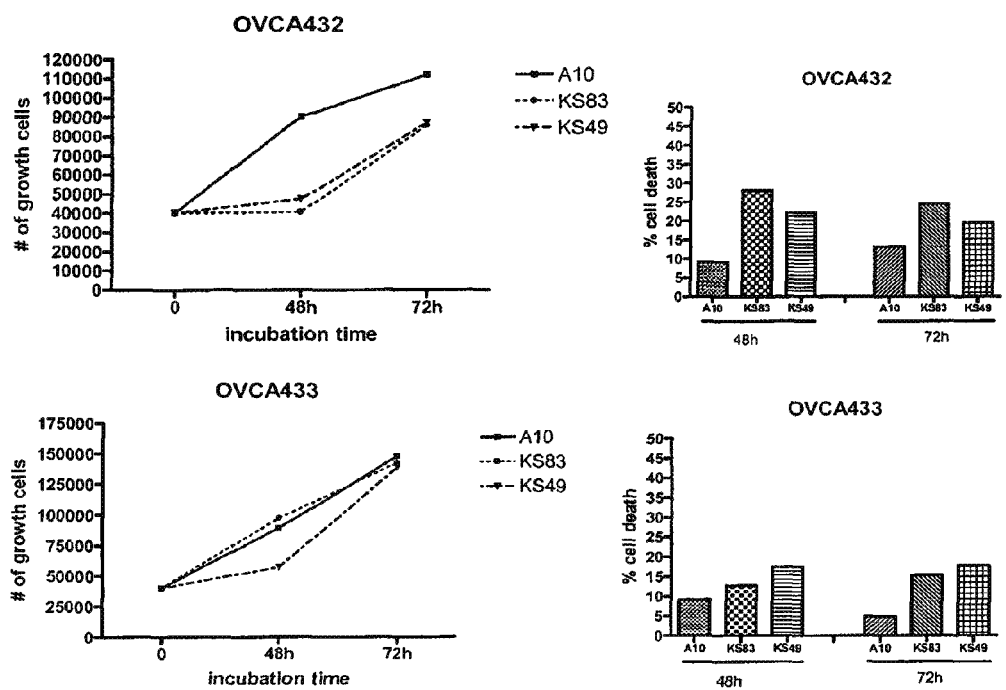
Figure 21, continued

S49 heavy chain (SEQ ID NO.:6):
MAQVQLVQSGGGVVQPGRSLRLSCAASGFTFSSYAMH WVRQAPGKGLEWVAVIS
                                    CDR-H1 (SEQ ID NO.:14)
YDGSNKYYADSVKGRFTISRDNSKNTLYLQMNSLRAEDTAVYYCARDRRGRKSA
CDR-H2 (SEQ ID NO.:16)                                CDR-H3 (SEQ ID NO.:39)
GIDYWGQGTLVTVSS S49 light chain (SEQ ID NO.:7):
DIQMTQSPSSLSASVGDRVTITCQASQDISNYLN WYQQKPGKAPKLLIYAASSL
                        CDR-L1 (SEQ ID NO.:18)    CDR-L2 (SEQ ID NO.:21)
QSGVPSRFSGSGSGTDFTLTISSLQPEDFATYYCLQDYNGWT FGQGTKVDIKRA
                                    CDR-L3 (SEQ ID NO.:40)
AAAEQKLISEEDLNGAA S83 heavy chain (SEQ ID NO.:8):
MAQVQLVESGGGLVQPGGSLRLSCAASGFTFGSYAMH WVRQAPGKGLEWVAVIS
                                    CDR-H1 (SEQ ID NO.:14)
YDGSNKYYADSVKGRFTISRDNSKNTLYLQMNSLRAEDTAVYYCARTVGATGAF
CDR-H2 (SEQ ID NO.:16)                                CDR-H3 (SEQ ID NO.:37)
DIWGQGTMVTVSS S83 light chain (SEQ ID NO.:9):
DIVMTQSPSTVSASVGDRVIIPCRASQSIGKWLA WYQQKPGKAPKLLIYKASSL
                      CDR-L1 (SEQ ID NO.:19)      CDR-L2 (SEQ ID NO.:22)
EGWVPSRFSGSGSGTEFSLTISSLQPDDGATYVCQQGHNFPPT FGGGTKLEIKR
                                    CDR-L3 (SEQ ID NO.:38)
AAAEQKLISEEDLNGAA

Figure 24

S41 heavy chain (SEQ ID NO.:10):
MAQVQLVQSGGGLVQPGRSLRLSCAASGFSFSEYPMHWVRQAPGRGLESVAVIS
                              CDR-H1 (SEQ ID NO.:15)
YDGEYQKYADSVKGRFTISRDDSKSTVYLQMNSLRPEDTAVYYCARTINNGMDV
  CDR-H2 (SEQ ID NO.:41)                   CDR-H3 (SEQ ID NO.:17)
WGQGTTVTVSS S41 light chain (SEQ ID NO.:11):
DIVMTQSPSSLSASVGDRVTITCRASQGIRNDLGWYQQKPGKAPELLIYGASSL
                        CDR-L1 (SEQ ID NO.:20)          CDR-L2 (SEQ ID NO.:23)
QSGVPSRFSGSGSGTDFTLTISSLQPEDSATYYCLQDYNGWTFGQGTKLEIKRA
                                 CDR-L3 (SEQ ID NO.:40)
AAEQKLISEEDLNGAA S89 heavy chain (SEQ ID NO.:12):
MAQVQLVQSGGGLVQPGRSLRLSCAASGFSFSEYPMHWVRQAPGRGLESVAVIS
                              CDR-H1 (SEQ ID NO.:17)5
YDGEYQKYADSVKGRFTISRDDSKSTVYLQMNSLRPEDTAVYYCARTINNGMDV
  CDR-H2 (SEQ ID NO.:17)                   CDR-H3 (SEQ ID NO.:41)
WGQGTTVTVSS S89 light chain (SEQ ID NO.:13):
DIVMTQSPSSLSASVGDRVTITCRASQGIRNDLGWYQQKPGKAPELLIYGASSL
                        CDR-L1 (SEQ ID NO.:20)          CDR-L2 (SEQ ID NO.:23)
QSGVPSRFSGSGSGTDFTLTISSLQPEDSATYYCLQDYRGWTFGQGTKLEIKRA
                                 CDR-L3 (SEQ ID NO.:40)
AAEQKLISEEDLNGAA Figure 24 (continued)

Diabody sequence (KS49)
Heavy chain, KS49 (SEQ ID NO.:43)
MAQVQLVQSGGGVVQPGRSLRLSCAASGFTFSSYAMHWVRQAPGKGLEWVAVISYDGSNKYYADS
VKGRFTISRDNSKNTLYLQMNSLRAEDTAVYYCARDRRGRKSAGIDYWGQGTLVTVSS

CDR1 SYAMH (SEQ ID NO.:14)
CDR2 VISYDGSNKYYADSVKG (SEQ ID NO.:16)

Light chain, KS49 (SEQ ID NO.:7)
DIQMTQSPSSLSASVGDRVTITCQASQDISNYLNWYQQKPGKAPKLLIYAASSLQSGVPSRFSGSGS
GTDFTLTISSLQPEDFATYYCLQDYNGWTFGQGTKVDIKRAAAEQKLISEEDLNGAA

CDR1 QASQDISNYLN (SEQ ID NO.:18)
CDR2 AASSLQS (SEQ ID NO.:21)

Diabody sequence (KS83)
Heavy chain, KS83 (SEQ ID NO.:44)
MAQVQLVESGGGLVQPGGSLRLSCAASGFTFSSYAMHWVRQAPGKGLEWVAVISYDGSNKYYADS
VKGRFTISRDNSKNTLYLQMNSLRAEDTAVYYCARTVGATGAFDIWGQGTMVTVSS

CDR1 SYAMH (SEQ ID NO.:14)
CDR2 VISYDGSNKYY ADSVKG (SEQ ID NO.:16)

Light Chain, KS83 (SEQ ID NO.:9)
DIVMTQSPSTVSASVGDRVIIPCRASQSIGKWLAWYQQKPGKAPKLLIYKASSLEGWVPSRFSGSGSG
TEFSLTISSLQPDDSATYVCQQSHNFPPTFGGGTKLEIKRAAAEQKLISEEDLNGAA

CDR1 RASQSIGKWLA (SEQ ID NO.:19)
CDR2 KASSLEG (SEQ ID NO.:22)

Figure 25

Diabody sequence (KS41)
Heavy Chain, KS41 (SEQ ID NO.:10)
MAQVQLVQSGGGLVQPGRSLRLSCAASGFSFSEYPMHWVRQAPGRGLESVAVISYDGEYQKYADS
VKGRFTISRDDSKSTVYLQMNSLRPEDTAVYYCARTINNGMDVWGQGTTVTVSS

CDR 1 EYPMH (SEQ ID NO.:15)
CDR 2 VISYDGEYQKYADSVKG (SEQ ID NO.:17)

Light Chain, KS41 (SEQ ID NO.:11)
DIVMTQSPSSLSASVGDRVTITCRASQGIRNDLGWYQQKPGKAPELLIYGASSLQSGVPSRFSGSGS
GTDFTLTISSLQPEDSATYYCLQDYNGWTFGQGTKLEIKRAAAEQKLISEEDLNGAA

CDR 1 RASQGIRNDLG (SEQ ID NO.:20)
CDR 2 GASSLQS (SEQ ID NO.:23)

Diabody sequence (KS89)
Heavy Chain, KS89 (SEQ ID NO.:12)
MAQVQLVQSGGGLVQPGRSLRLSCAASGFSFSEYPMHWVRQAPGRGLESVAVISYDGEYQKYADS
VKGRFTISRDDSKSTVYLQMNSLRPEDTAVYYCARTINNGMDVWGQGTTVTVSS

CDR1 EYPMH (SEQ ID NO.:15)
CDR 2 VISYDGEYQKY ADSVKG (SEQ ID NO.:17)

Light Chain, KS89 (SEQ ID NO.:13)
DIVMetTQSPSSLSASVGDRVTITCRASQGIRNDLGWYQQKPGKAPELLIYGASSLQSGVPSRFSGSG
SGTDFTLTISSLQPEDSATYYCLQDYNGWTFGQGTKLEIKRAAAEQKLISEEDLNGAA

CDR 1 RASQGIRNDLG (SEQ ID NO.:20)
CDR 2 GASSLQS (SEQ ID NO.:23)

Figure 25 (continued)

Full polypeptide sequence of anti-EMP2 diabodies

KS49 (SEQ ID NO:33)
MAQVQLVQSGGGVVQPGRSLRLSCAASGFTFSSYAMHWVRQAPGKGLEWVAVISYDGSNKYYADSVK
GRFTISRDNSKNTLYLQMNSLRAEDTAVYYCARDRRGRKSAGIDYWGQGTLVTVSSGGGSDIQMTQSP
SSLSASVGDRVTITCQASQDISNYLNWYQQKPGKAPKLLIYAASSLQSGVPSRFSGSGSGTDFTLTISS
LQPEDFATYYCLQDYNGWTFGQGTKVDIKRAAAEQKLISEEDLNGAAHHHHHH

KS83 (SEQ ID NO:34)
MAQVQLVESGGGLVQPGGSLRLSCAASGFTFSSYAMHWVRQAPGKGLEWVAVISYDGSNKYYADSVK
GRFTISRDNSKNTLYLQMNSLRAEDTAVYYCARTVGATGAFDIWGQGTMVTVSSGGGSDIVMT
QSPSTVSASVGDRVIIPCRASQSIGKWLAWYQQKPGKAPKLLIYKASSLEGWVPSRFSGSGTEFSLTI
SSLQPDDSATYVCQQSHNFPPTFGGGTKLEIKRAAAEQKLISEEDLNGAAHHHHHH

KS41 (SEQ ID NO:35)
MAQVQLVQSGGGLVQPGRSLRLSCAASGFSFSEYPMHWVRQAPGRGLESVAVISYDGEYQKYADSVK
GRFTISRDDSKSTVYLQMNSLRPEDTAVYYCARTINNGMDVWGQGTTVTVSSGGGSDIVMTQSPSSL
SASVGDRVTITCRASQGIRNDLGWYQQKPGKAPELLIYGASSLQSGVPSRFSGSGSGTDFTLTISSLQP
EDSATYYCLQDYNGWTFGQGTKLEIKRAAAEQKLISEEDLNGAAHHHHHH

KS89 (SEQ ID NO:36)
MAQVQLVQSGGGLVQPGRSLRLSCAASGFSFSEYPMtHWVRQAPGRGLESVAVISYDGEYQKYADSVK
GRFTISRDDSKSTVYLQMNSLRPEDTAVYYCARTINNGMDVWGQGTTVTVSSGGGSDIVMetTQSPSS
LSASVGDRVTITCRASQGIRNDLGWYQQKPGKAPELLIYGASSLQSGVPSRFSGSGSGTDFTLTISSLQ
PEDSATYYCLQDYNGWTFGQGTKLEIKRAAAEQKLISEEDLNGAAHHHHHH

Figure 26

METHODS OF TREATING CANCER BY ADMINISTERING EMP2 ANTIBODIES

CROSS-REFERENCES TO RELATED APPLICATIONS

This application is a Continuation of U.S. application Ser. No. 12/682,032 filed Jul. 7, 2010, now U.S. Pat. No. 8,318,906 which is a 371 of PCT/US08/79244 filed Oct. 8, 2008 and is a Continuation-in-part of U.S. patent application Ser. No. 11/868,788 filed Oct. 8, 2007, now U.S. Pat. No. 8,648,052, which is a Continuation-in-part of PCT/US06/14238 filed Apr. 14, 2006 which claims the benefit under 35 U.S.C. §119(e) to U.S. Application No. 60/671,755 filed Apr. 15, 2005, the disclosure of each of which is incorporated by reference in its entirety.

STATEMENT AS TO RIGHTS TO INVENTIONS MADE UNDER FEDERALLY SPONSORED RESEARCH AND DEVELOPMENT

This invention was made with Government support under Grant Nos. AI007323, CA009120, CA016042, CA086306, CA119367, GM007185, and HD048540, awarded by the National Institutes of Health. This work was supported by the U.S. Department of Veterans Affairs. The Government has certain rights in the invention.

REFERENCE TO A "SEQUENCE LISTING," A TABLE, OR A COMPUTER PROGRAM LISTING APPENDIX SUBMITTED ON A COMPACT DISK

The sequence listing contained in the file named "008074-5003-US02_ST25.txt" and having a size of 34.9 kilobytes, has been submitted electronically herewith via EFS-Web, and the contents of the txt file are hereby incorporated by reference in their entirety.

FIELD OF THE INVENTION

This invention relates anti-EMP2 antibodies, their pharmaceutical compositions and methods for using them in detecting and treating cancers, such as endometrial cancers, which express or overexpress EMP2 and in treating or preventing infection by *Chlamydia*.

BACKGROUND OF THE INVENTION

The epithelial membrane protein-2 (EMP2) is a member of the growth arrest specific-3/peripheral myelin protein-22 (GAS3/PMP22) family of tetraspan proteins. Other four-transmembrane families, connexins and tetraspanins, play roles in gap junctions, cell-cell recognition processes, and intracellular trafficking. Less is known about the GAS3/PMP22 family. The information available mainly relates to their potential roles in various diseases. For instance, mutations in the prototypic GAS3 family member PMP22 have been found to cause neurodegenerative disease (i.e., Dejerrine Sottas Syndrome and Charcot Marie Tooth Syndrome). EMP2 has also been implicated in B cell tumor progression and stress-induced apoptosis.

EMP2 is expressed at high levels in epithelial cells of the lung, eye, and genitourinary tracts. Like several tetraspan proteins (CD9, CD81, PMP22), EMP2 in murine fibroblasts is localized to lipid raft domains. EMP2 controls cell surface trafficking and function of certain integrins, GPI-linked proteins, and class I MHC molecules, and reciprocally regulates caveolin expression. (see, Claas et al., *J Biol Chem* 276:7974-84 (2001); Hasse et al., *J Neurosci Res* 69:227-32 (2002); Wadehra et al., *Exp Mol Pathol* 74:106-12 (2003); Wadehra et al., *Mol Biol Cell* 15:2073-2083 (2004); Wadehra et al., *J Biol Chem* 277:41094-41100 (2002); and Wadehra et al., *Clin Immunol* 107:129-136 (2003)).

Detailed studies of the subanatomic distribution of EMP2 in murine and human ocular tissue indicate that EMP2 is localized to epithelial layers of the cornea, ciliary body, and retinal pigmented epithelium-choroid, the stromal layers of the sclera, and the nerve fiber layer of the retina and optic nerve. This distribution is distinct from other TM4SF proteins and may relate to a role in apical membrane recycling.

Endometrial cancer (EC) is the most common gynecological malignancy. In the United States, the death rate from EC has doubled in the last twenty years, and currently a woman has approximately a 3% chance of developing EC during her lifetime (Silverberg et al., *World Health Organization Classification of Tumors: Tumors of the Breast and Female Genital Tract*, Lyon: IARC Press, p. 221-57 (2003); Sorosky J I, *Obstet Gynecol* 111:436-47 (2008)). EC is classified into two major sub-groups based on histology, clinical behavior, and epidemiology. The more common Type I is associated with estrogen predominance and pre-malignant endometrial hyperplasia (Hecht et al., *J Clin Oncol* 24:4783-91 (2006); Sherman, *Mod Pathol* 13:295-308 (2000)). Type II is mediated by non-hormonal risk factors, and often has a high grade or high-risk histology with an aggressive clinical course (Hecht et al., *J Clin Oncol* 24:4783-91 (2006)). Incidence of ECs generally increases with age, with 75-80% of new cases occurring in postmenopausal women (Creasman, *Semin Oncol* 24:S1-140-51-50 (1997)).

Primary treatment for ECs is the surgical removal of the tumor, but recurrence is common, and other therapeutic interventions (radiotherapy, chemotherapy, and endocrine therapy) benefit only a subset of patients (Markman, *Semin Oncol* 33: S33-8 (2006); Engleman et al., *Semin Oncol* 30:80-94 (2003)). Presently, there are few biomarkers that distinguish ECs at the pre-malignant stage, although emerging efforts are targeting molecules that underlie the process of tumorigenesis (Kelloff et al., *Clin Cancer Res* 12:3661-97 (2006); Gossett et al., *Int J Gynecol Cancer* 14:145-51 (2004)). Similarly, there are currently no biomarkers that can be targeted for tumor suppression and elimination. Thus, new modalities for early detection and treatment of ECs at premalignant and frankly malignant stages of disease are needed to improve management and prognosis.

One promising biomarker appears to be EMP2. EMP2 expression is associated with EMP2 neoplasia (Wadehra et al., *Cancer* 107:90-8 (2006)). In endometrial cancer, EMP2 is an independent prognostic indicator for tumors with poor clinical outcome. EMP2 positive tumors, compared to EMP2 negative tumors, had a significantly greater myometrial invasiveness, higher clinical state, recurrent or persistent disease following surgical excision, and earlier mortality. As EMP2 expression was independent of other known biomarkers such as the estrogen receptor and progesterone receptor (Wadehra et al., *Cancer* 107:90-8 (2006)), EMP2 represents a unique biomarker for patients who are not responsive to current hormone or chemotherapy. Moreover, EMP2 expression level positively correlates with the increasing pre-malignant potential of proliferative endometrium. That is, there is a gradation of endometrial EMP2 expression, with minimal expression in normal proliferative or quiescent premenopausal endometrium, and increasing expression in patients with disordered proliferative endometrium, endometrial hyperplasia, and endometrium carcinomas.

In the endometrium, EMP2 expression is regulated by progesterone and required for successful blastocyst implantation (Wadehra et al., *DevBiol* 292:430-41 (2006); Wadehra et al., *Reprod Biol Endocrinol* 6:15 (2008)). EMP2 appears to regulate trafficking of various proteins and glycolipids by facilitating transfer of molecules from post-Golgi endosomal compartments to appropriate plasma membrane locations. Specifically, EMP2 is thought to facilitate the appropriate trafficking of select molecules into glycolipids-enriched lipid raft microdomains (GEMs) (Wadehra et al., *Mol Biol Cell* 15:2073-83 (2004)). GEMs are cholesterol rich microdomains which are often associated with chaperones, receptosomes, and protein complexes that are important for efficient signal transduction (Leitinger et al., *J Cell Sci* 115:963-72 (2002); Moffett et al., *J Biol Chem* 275:2191-8 (2000)). Moreover, GEMs are involved in correct sorting of proteins from the Golgi apparatus to plasma membrane (Abrami et al., *J Biol Chem* 276:30729-36 (2001); Galbiati et al., *Cell* 106:403-11 (2001); Gruenberg et al., *Curr Opin Cell Biol* 7:552-63 (1995)). In this respect, modulation of EMP2 expression levels or its location on the plasma membrane alters the surface repertoire of several classes of molecules including integrins, focal adhesion kinase, class I major histocompatibility molecules and other immunoglobulin super-family members such as CD54 and GPI-linked proteins (Wadehra et al., *DevBiol* 287:336-45 (2005); Wadehra et al., *Clinical Immunology* 107:129-36 (2003); Morales et al., *Invest Ophthalmol Vis Sci* (2008)).

Chlamydiae are obligate gram-negative intracellular prokaryotic pathogens that are responsible for significant human morbidity and infections of multiple organ systems. More than 90 million new cases of sexually transmitted, genitourinary *Chlamydia trachomatis* infection are reported annually. These infections are a significant cause of infertility, ectopic pregnancy, and chronic pelvic pain syndromes (Brunham & Rey-Ladino, *J. Nat Rev Immunol* 5:149-61 (2005)). Ocular infections with *Chlamydia* may result in trachoma, the primary cause of infectious blindness worldwide (see, Engel, *Proc Natl Acad Sci USA* 101:9947-8 (2004)), and *Chlamydia* species also have been associated with other inflammatory diseases (see, Hannu et al. *Rheumatology* (Oxford) 38:411-4 (1999), Gencay et al., *Am J Respir Crit. Care Med* 163:1097-100 (2001); Smieja et al., *BMC Infect Dis* 2:21 (2002); and Dautry-Varsat et al., *Traffic* 5:561-570 (2004)). The pathophysiology of Chlamydial infections is only partly understood, in particular identification of host cellular proteins involved in Chlamydial infection that may reveal new strategies for disease control.

*Chlamydia* has a unique biphasic developmental cycle. The first step in infection requires attachment of a metabolically inactive but infectious, spore-like structure called the elementary body (EB). The initial reversible attachment of EB to epithelial cell layers is proposed to involve a number of Chlamydial and host ligands and adhesions. Possible candidates for attachment mediation include major outer membrane protein (MOMP), heat shock protein 70, OmcB, heparin sulfate-like glycosaminoglycans, polymorphic outer membrane protein gene family (pmp), estrogen receptor complex, and caveolae. Upon cellular attachment local actin polymerization, elicited by intracellular secretion of EB products and tyrosine phosphorylation of various protein species leads to endocytosis of the attached EB. After a few hours, an internalized EB differentiates into the reticulate body (RB), a metabolically active, non-infectious form which gives rise to >1000 progeny EBs, followed by host cell lysis and release of infectious EBs that begin another life cycle (see, Engel, *Proc Natl Acad Sci USA* 101:9947-8 (2004); Dautry-Varsat et al., *Traffic* 5:561-570 (2004); Gabel et al., *Infect Immun* 72:7367-73 (2004); Davis et al., *Proc Natl Acad Sci USA* 99:9427-32 (2002); Raulston et al., *Infect Immun* 70:535-43 (2002); Finlay, et al., *Science* 276:718-725 (1997); and Virok et al., *Infect Immun* 73:1939-46 (2005)).

Chlamydial infection can result from oral, vaginal, or anal sexual contact with an infected partner. *Chlamydia trachomatis* can be sexually transmitted. In women, the pathogen can cause pelvic inflammatory disease (PID) with a risk of tubal obstruction and infertility. In men, the bacteria can cause epidydimitis and infertility. *Chlamydia* can also cause acute respiratory tract infections in humans. Infection of the eye with *Chlamydia trachomatis*, or trachoma, is a leading cause of preventable blindness worldwide. Chlamydial infections are a particularly serious health threat to newborns who contract occular infections at birth from infected birth canals of their mothers. If untreated, almost 50% of these children develop inclusion conjunctivitis and 20% develop systemic infection resulting in serious pneumonia. *Chlamydia* also is likely to exacerbate atherosclerosis. In particular, coronary heart disease has been associated with increased titers of *Chlamydia* antibodies. In addition, reactive inflammatory arthritis is a common sequel to sexually acquired non-gonococcal genital tract infection. Approximately 50% of reactive inflammatory arthritis cases are associated with *Chlamydia trachomatis* infection of the genital tract. Chlamydial infection can be asymptomatic and irreversible damage may have already occurred before treatment is sought.

Accordingly, *Chlamydia* is a serious public health concern around the world. However, *Chlamydia* is an intracellular pathogen which is difficult to treat. There is no robust vaccine for *Chlamydia* and conventional antibiotic therapies often fail to clear chronic infections.

Recent studies indicate that the interaction between *Chlamydia* and host cells occurs at specific cholesterol- and glycosphingolipids-rich lipid raft microdomains. Lipid rafts, often experimentally defined by their insolubility in cold non-ionic detergents are believed to be subspecialized cell membrane regions important in assembly of receptor signaling complexes, protein trafficking, endocytic and secretory pathways. Many other proteins associated with bacterial infection have been found in lipid raft compartments. Dautry-Varsat et al., *Traffic* 5:561-570 (2004); Simons et al., *Nature* 387:569-572 (1997); Gabel et al., *Infect Immun* 72:7367-73 (2004); Claas et al., *J Biol Chem* 276:7974-84 (2001); Brown et al. *J Biol Chem* 275:17221-4 (2000); and Subtil et al., *J Cell Sci* 117:3923-33 (2004); and Webley et al., *BMC Infect Dis* 4:23 (2004).

As reported herein, the Applicants have discovered that EMP2 is a useful target for anti-cancer therapy for cancers which express or overexpress EMP2 molecular cell entry and also that EMP2 is a cell entry point for *Chlamydia*. Accordingly, EMP2 polypeptides, anti-EMP2 antibodies, and EMP2 siRNA can be used to modulate the ability of *Chlamydia* to enter a host cell to cause infection and disease and can be used also to treat cancers expressing or overexpressing EMP2 As discussed above, there remains a large need for methods and compositions which are useful in the prevention, treatment, and modulation of *Chlamydia* infection as well as the prevention, diagnosis and treatment of cancer. Accordingly, this invention provides novel compositions and methods for meeting these and other needs.

BRIEF SUMMARY OF THE INVENTION

In a first aspect, the invention relates to the discovery that epithelial membrane protein-2 (EMP2) is a molecular cell entry point for *Chlamydia* Inhibiting the access of *Chlamydia* to EMP2 can inhibit the ability of *Chlamydia* to enter a host cell and/or to cause infection. Accordingly, in this first aspect, the invention provides pharmaceutical compositions comprising EMP2 *Chlamydia* inhibitors and methods of using them in the prevention or treatment of infection with *Chlamydia* or the entry of *Chlamydia* into a host cell expressing EMP2. In this first aspect, the invention provides human-origin antibody sequences which encode for high-avidity binding proteins specific for EMP2 (e.g., KS49, KS83, KS41, and KS89).

Also in this first aspect, the invention provides pharmaceutical compositions comprising these anti-EMP2 antibodies. These antibodies are capable of specifically binding to the EMP2 of a host cell and of inhibiting the ability of *Chlamydia* to enter the host cell or infect a host. The anti-EMP2 antibody may attach to any epitope of the EMP polypeptide. In some embodiments the antibody can bind to a polypeptide comprising the amino acid sequence of SEQ ID NO:1 or SEQ ID NO:2. In some embodiments, the antibody recognizes an extracellular or external epitope (e.g., external loop antigen) of EMP2. In any of the above embodiments, the anti-EMP2 antibody can be a polyclonal antibody or a monoclonal antibody. In addition, the antibody may further be a human antibody, a humanized antibody, a chimeric antibody, a recombinant antibody, a diabody, minibody, triabody, or an antibody fragment having the light and heavy variable chain sequences or CDRs corresponding to the KS49, KS83, KS41, and KS89 sequences disclosed herein.

In this first aspect, the invention also accordingly provides for the use of an anti-EMP2 antibody in the manufacture of a medicament for treating *Chlamydia*.

In some embodiments, the above described pharmaceutical compositions which comprise the anti-EMP2 antibody are formulated for topical application to the surface of the eye or a mucosal surface. In some additional embodiments of the above, the pharmaceutical compositions are formulated as part of an antibiotic composition which may be a cream, lotion, gel or ointment. These antibiotics include, but are not limited to, azithromycin, amoxicillin, doxycycline, erythromycin, erythromycin ethylsuccinate, ofloxacin and levofloxacin. In some further embodiments, the pharmaceutical compositions according to the invention are formulated as part of a contraceptive composition which may be a cream, lotion, ointment, or gel comprising a spermicidal agent. In still other embodiments, the pharmaceutical compositions of the invention are formulated with a lubricant. In some embodiments, the EMP2 *Chlamydia* inhibitor is formulated as an intravaginal or condom-coating medicament including, but not limited to, ointments, lotions, gels, and creams.

In still other embodiments of the above pharmaceutical compositions which comprise an anti-EMP2 antibody, the compositions are formulated for topical administration to the eye. These compositions may be co-formulated with an antibiotic useful in treating *Chlamydia* infection.

In addition, the invention also provides methods of treating *Chlamydia* infections using the above-described pharmaceutical compositions. In this first aspect, the invention also provides methods for treating or preventing infection with *Chlamydia* in a subject by administering a pharmaceutical composition comprising a therapeutically effective amount of an anti-EMP2 antibody to the subject. In some embodiments, the person to be treated has been diagnosed as having a *Chlamydia* infection or has or will engage in behavior which places them at risk for such infection. In some embodiments, the *Chlamydia* species is *C. trachoma*. In some embodiments, the subject is a person who is infected with *Chlamydia* and has been diagnosed with conjunctivitis, pelvic inflammatory disease, arteriosclerosis, elevated C-reactive protein, arthritis, a urogenital tract infection or pneumonia exacerbated or associated with infection by *Chlamydia*. In some embodiments, the subject is also treating with an antibiotic useful in treating *Chlamydia* infections. These antibiotics include, but are not limited to, azithromycin, amoxicillin, doxycycline, erythromycin, erythromycin ethylsuccinate, ofloxacin and levofloxacin.

In this first aspect, the invention also provides compositions of anti-EMP2 antibodies which can be used to inhibit or prevent the entry of *Chlamydia* into a host cell which expresses EMP2 or is otherwise is capable of expressing EMP2. The EMP2 *Chlamydia* antibodies may be formulated in a physiologically acceptable carrier, preferably, sterile.

In each of the above embodiments, the host cell or subject to be treated can be human, primate, or mammal (e.g., mouse, rat, rabbit) or bird. In further embodiments of any of the above aspects, the *Chlamydia* is *C. trachoma*.

In a second aspect, the present invention relates to the EMP2 protein as a molecular target in the diagnosis and treatment of cancer. Accordingly, in this second aspect the invention provides methods of diagnosis and prognosis for individuals having, or suspected of having, or at increased risk for cancers that express or overexpress EMP2 protein or an EMP2 mRNA transcript (e.g., endometrial cancer, ovarian cancer, glioblastoma, breast cancer, prostate cancer, testicular cancer, and myeloma). The diagnostic methods generally comprise testing tissue sample from an individual having or suspected of having a cancer that overexpresses EMP2 protein or mRNA transcript and determining the presence or absence or amount of EMP2 protein or mRNA transcript in the tissue relative to a control tissue sample from an individual or site known to be negative for cancer. Typically, the tissue sample is serum, but can also be biopsy tissue, including tissue from the affected tissue.

Further, in this second aspect, the EMP2 markers can help in the prognosis of whether a cancer will progress to a treatment resistant or hormone independent state, become invasive, and/or metastasize. The present invention further provides methods of inhibiting the growth of and promoting the regression of a cancerous tumor that expresses or overexpresses EMP2 by contacting the cancer with anti-EMP2 antibody.

In some embodiments, the invention provides methods of diagnosing a cancer in a subject by determining the level of EMP2 protein expression or activity in a biological sample or biopsy of the cancer or tumor from the subject wherein an increased level of EMP2 is indicative of cancer. In some embodiments, determining the EMP2 protein levels involves steps of (a) contacting a tissue sample or biopsy from the subject with an antibody that specifically binds to EMP2 protein; and (b) determining whether or not EMP2 protein is overexpressed in the sample or biopsy; thereby diagnosing the cancer. In a further embodiment of such, the cancer can be endometrial cancer, ovarian cancer or a glioblastoma. In some further embodiments, still the tissue sample can be a needle biopsy, a surgical biopsy or a bone marrow biopsy. A tissue sample can be fixed or embedded in paraffin. A tissue sample can be, for instance, from the endometrium, ovary, or brain. The antibody in some embodiments is a monoclonal antibody or a diabody.

In other embodiments of the second aspect, the method indirectly determines the EMP2 protein level by (a) contacting a tissue sample with a primer set of a first oligonucleotide and a second oligonucleotide that each specifically hybridize to EMP2 nucleic acid; (b) amplifying the EMP2 nucleic acid in the sample; and (c) determining whether or not EMP2 nucleic acid is overexpressed in the sample; thereby diagnosing the cancer. The first oligonucleotide can comprise a nucleotide sequence of EMP2 cDNA and the second oligonucleotide can comprise a nucleotide sequence complementary to that of EMP2 cDNA. Preferably, both nucleotides are less than 50 base pairs in length. In a preferred embodiment, the cancer is endometrial or ovarian cancer.

In this second aspect, the invention also provides a method of prognosis for a cancer that overexpresses EMP2 by assessing the likelihood that the cancer will be invasive, metastasize, recur or be resistant to therapy. In a first embodiment in this aspect, the invention provides a method of further diagnosing a cancer that overexpresses EMP2 has increased EMP2 transcriptional activity and therefore has an increased likelihood of invasiveness, metastasizing, recurrence or resistance to therapy. The method comprises the steps of (a) contacting a tissue sample with an antibody that specifically binds to EMP2; and (b) determining whether or not the EMP2 is overexpressed in the sample; thereby diagnosing the cancer that overexpresses EMP2. The cancer may be diagnosed before or after obtaining and analyzing the sample for EMP2 expression or activity levels. The cancer may have been identified on the basis of histological appearance and not on the basis of the EMP2 level determination. The cancer can have been diagnosed as such with or without, or despite, knowledge of an elevated EMP2 level. In some further embodiments, still the tissue sample can be a needle biopsy, a surgical biopsy or a bone marrow biopsy. A tissue sample can be fixed or embedded in paraffin. A tissue sample can be, for instance, from the endometrium, ovary, or brain. The antibody in some embodiments is a monoclonal antibody or diabody.

In yet other embodiments in this second aspect, the invention provides a method of targeting patients for more aggressive or alternative cancer therapy or increased surveillance for a cancer recurrence based upon an elevated level of EMP2 in a tissue sample from the patient taken before, during, or after surgical removal of the cancerous tissue before, during, or after another cancer treatment. The EMP2 activity or expression levels can be determined as described above.

In some further embodiments, the invention provides a method of treating or inhibiting a cancer, a therapy resistant cancer, a metastasis of cancer, or recurrence of cancer, that overexpresses EMP2 in a subject comprising administering to the subject a therapeutically effective amount of one or more inhibitors of EMP2 expression. The cancer that overexpresses EMP2 can be, for instance, endometrial cancer, ovarian cancer, glioblastoma, breast cancer, prostate cancer, testicular cancer, and myeloma. The compound can be a compound as identified in the following aspect. The overexpression can be identified as described in the previous aspects. The compound can be administered concurrently with another cancer therapy.

In a different therapeutic approach, the treatment includes the administration of a progesterone or other non-estrogenic progesterone steroid to increase tissue expression of EMP2 so as to increase the sensitivity of the cancers to a therapy targeting cells expressing or over-expressing EMP2. The steroid can be a progesterone derivative (e.g., hydroxyprogesterone caproate, medroxyprogesterone acetate, or megestrol acetate). The therapy targeting the EMP2 can be an anti-EMP2 antibody as disclosed herein. In some embodiments, the anti-EMP2 antibody is a diabody. Optionally, the antibody or diabody may be further conjugated to, or covalently attached to, an antineoplastic agent.

In this second aspect, the invention also provides a method of identifying a compound that inhibits cancer, therapy resistant cancer, or metastasis, or a recurrence of cancer, the method comprising the steps of contacting a cell with a compound; and determining the effect of the compound on the expression or activity of the EMP2 polypeptide in the cell; wherein compounds which decrease the EMP2 expression or activity levels are identified as being able to inhibit cancer, its metastasis, or progression to a hormone-independent or treatment resistant state. In some embodiments, the compound increases the expression of EMP2 in the target cell.

The invention also provides a method of localizing a cancer that overexpresses EMP2 in vivo, and is therefore likely to be invasive, likely to metastasize, become hormone independent, or refractory to treatment, the method comprising the step of imaging in a subject a cell overexpressing EMP2. In some embodiments, the cancer that overexpresses EMP2 is selected from the group consisting of endometrial cancer, ovarian cancer, glioblastoma, breast cancer, prostate cancer, testicular cancer, and myeloma.

In addition, EMP2 proteins and EMP2-encoding nucleic acid molecules may be used in various immunotherapeutic methods to promote immune-mediated destruction of cancers particularly, when such tumors are invasive.

In some embodiments, the invention provides methods of treating cancer, particularly an invasive cancer or a metastasis, or preventing the progression of a cancer to a treatment resistant, hormone-independent, or metastasizing state by administering antibodies that bind to EMP2 to reduce their respective activity in the patient. Additionally, in some other embodiments, the antibodies are conjugated to effector moieties which thereby are preferentially cytotoxic to cells overexpressing the EMP2. In some embodiments, the antibodies are diabodies or humanized monoclonal antibodies.

In some embodiments, the invention provides methods of treating cancer or preventing the progression of a cancer to a treatment resistant, hormone-independent, or metastasizing state by administration of RNAi molecule or an antisense molecule specific for EMP2 and which accordingly are capable of inhibiting the expression of EMP2. In some embodiments, the RNAi molecule may be a short hairpin RNAi.

In this second aspect, the invention also provides EMP2 polypeptides, anti-EMP2 antibodies, and EMP2 siRNA which would be of use in treating or preventing cancers which overexpress EMP2. EMP2 is overexpressed in a number of classes of tumor, including endometrial cancer, ovarian cancer, glioblastoma, breast cancer, prostate cancer, testicular cancer, and myeloma. EMP2 antibodies may be used in diagnosis, prognosis, or the treatment of a cancer alone or when conjugated with an effector moiety. EMP2 antibodies conjugated with toxic agents, such as ricin, as well as unconjugated antibodies, may be useful therapeutic agents naturally targeted to EMP2 bearing cancer cells. Such antibodies can be useful in blocking invasiveness. EMP polypeptides and nucleic acids may be used in vaccine therapies for the cancer.

In any of the above aspects and embodiments, the tissue, cancer, subject, or patient to be treated is human or mammalian. In further embodiments, the cancer can be selected from endometrial cancer, ovarian cancer, glioblastoma, breast cancer, prostate cancer, testicular cancer, and myeloma. In still further embodiments, the anti-EMP2 antibody or EMP2-binding protein has the CDR or light and chain variable sequences for the KS49, KS83, KS41, and KS89 diabodies disclosed herein.

BRIEF DESCRIPTION OF THE DRAWINGS

FIG. 24. The amino acid sequences of the Heavy and Light chain variable regions of anti-EMP-2 antibodies KS49, KS41, KS89 and KS83 are shown. Suitable CDR sequences of the variable regions are identified using the Kabat CDR definition.

FIG. 25. The amino acid sequences of the Heavy and Light chain variable regions of anti-EMP-2 antibodies KS49, KS41, KS89 and KS83 showing the suitable CDR sequences for use in the antibodies of the invention.

FIG. 26. The amino acid sequences of the KS49, KS41, KS89 and KS83 diabodies with underlining of their linkers and polyhistidine tags.

DETAILED DESCRIPTION

Figure 1:
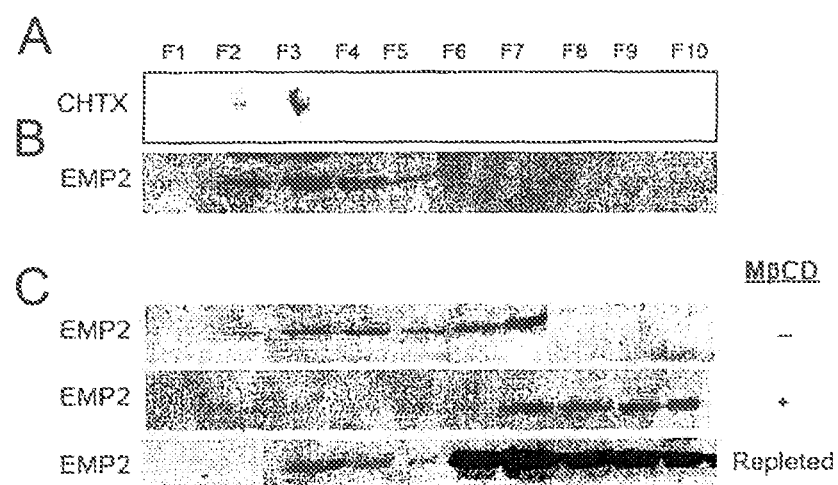
FIG. 1A-C. Illustration that EMP2 is targeted to lipid rafts and is disrupted following MβCD treatment. (a, b) Lipid raft fractionation by Brij 58 insolubility. HEC1A were lysed in 1% Brij 58, and centrifuged in a sucrose density gradient. Ten fractions (400 μl each) were collected from the gradient top and tested for (a) GM1 ganglioside by cholera toxin dot blot and (b) EMP2 (~$M_r$ 20 kDa) using SDS-PAGE and western analysis. (c) Cholesterol dependence of EMP2 lipid raft fractionation. HEC1A cells were preincubated in the absence (−) or presence (+) of MβCB, or repleted with cholesterol after MβCB treatment. Cells were then lysed in 1% Triton X-100, gradient fractionated, and EMP2 detected by western analysis. Experiments were performed independently three times with similar results.

Chlamydiae are bacterial pathogens which have evolved efficient strategies to enter, replicate, and persist inside host epithelial cells, resulting in acute and chronic diseases of humans and other animals. Understanding the molecular basis of initial Chlamydial attachment and entry is necessary to form strategies for prevention and treatment. However, few molecules of either Chlamydial or host origin have emerged as candidates for these processes, and the precise mechanism of infection has not been elucidated. Epithelial membrane protein-2 (EMP2) is a 4-transmembrane protein, highly expressed in epithelial cells of common sites for Chlamydial infection.

The Applicants have discovered that EMP2 resides in lipid rafts and is the target membrane microdomain for Chlamydial infection. They have also found that Chlamydial attachment and infection efficiency is linked to levels of EMP2 expression in HEC1A endometrial cells. Either blocking surface EMP2 with anti-EMP2 antibody or recombinant knockdown in EMP2 expression reduced both Chlamydial attachment and infection efficiency, whereas these processes were markedly augmented when EMP2 was recombinantly overexpressed. These findings indicate that EMP2 is a new host protein involved in *Chlamydia* attachment and infection.

Accordingly, in its first aspect, the invention provides compositions of anti-EMP2 antibodies in a physiologically acceptable carrier or a pharmaceutically acceptable carrier and methods of treating *Chlamydia* infections or preventing the entry of *Chlamydia* into a host cell using the anti-EMP2 antibodies.

Human monovalent anti-EMP2 antibody fragments were isolated from a human phage display library, and engineered as bivalent antibody fragments (diabodies) with specificity and avidity to both EMP2 peptides and native cell-surface EMP2 protein. The efficacy of these diabodies were assessed using cell death and apoptosis assays using endometrial cancer cells. In addition, the efficacy of EMP2 diabodies on EC tumors was determined using mouse xenograft models.

Treatment of human endometrial adenocarcinoma cell lines with anti-EMP2 diabodies was found to induce significant cell death and caspase 3 cleavage in vitro. These responses correlated with cellular EMP2 expression, and were augmented by progesterone (which physiologically induces EMP2 expression). In vivo, treatment of subcutaneous human xenografts of HEC-1A cell lines with anti-EMP2 diabodies suppressed tumor growth, and induced striking xenograft cell death.

Accordingly, in its second aspect, the invention provides compositions of EMP2 inhibitors in a physiologically acceptable carrier or a pharmaceutically acceptable carrier and methods of treating cancers which express or overexpress EMP2.

In both aspects, the invention provides exemplary anti-EMP2 antibodies for use in the diagnosis and treatment of cancer as well as for the treatment and prevention of infection by *Chlamydia*.

DEFINITIONS

Unless otherwise stated, the following terms used in the specification and claims have the meanings given below.

It is noted here that as used in this specification and the appended claims, the singular forms "a," "an," and "the" include plural reference unless the context clearly dictates otherwise.

Chlamydiae are obligate intracellular bacteria that infect animals, including mammals and birds, particularly at the epithelial lining of the lung, conjunctivae or genital tract. The term "*Chlamydia*" references the most common species of *Chlamydia* (i.e., *Chlamydia trachomatis, Chlamydia psittaci, Chlamydia pecorum* and *Chlamydia pneumoniae*). Recently, the newly designated species of *Chlamydia, C. pneumoniae* (formerly *C. trachomatis* TWAR) has been implicated as a major cause of epidemic human pneumonitis and perhaps may play a role in atherosclerosis.

"Inhibitors" are agents that inhibit a recited activity, function or entity. For example an inhibitor of *Chlamydia* infection blocks or reduces the ability of a *Chlamydia* bacteria to cause an infection. An inhibitor of *Chlamydia* entry into a host cell is an agent which blocks, prevents, decreases, reduces, or delays the entry of the bacteria into the host cell. An inhibitor of EMP2 binding to an anti-EMP2 antibody is an agent which reduces or competes with the binding of the EMP2 to the anti-EMP2 antibody.

An "EMP2 inhibitor" is an agent which interferes with the function, activity, or levels of EMP2. A EMP2 inhibitor can be EMP2 polypeptide; an anti-EMP2 antibody; an EMP2 siRNA molecule; an EMP2-ribozyme; a compound which competes with binding of to EMP2, or an agent or compound which inhibits the expression, transcription, or translation of EMP2 nucleic acids in a host cell. In some embodiments, the EMP2 inhibitors are provided in a composition also comprising a sterile carrier and/or physiologically acceptable carrier.

Accordingly, in the first aspect of the invention, an "EMP2 *Chlamydia* inhibitor" is an agent which interferes with the ability of *Chlamydia* to infect a host cell by interfering with *Chlamydia*'s ability to interact with, or bind to, EMP2 of the host cell. A EMP2 *Chlamydia* inhibitor can be EMP2 polypeptide; an anti-EMP2 antibody; an EMP2 siRNA molecule; an EMP2-ribozyme; a compound which competes with binding of *Chlamydia* to EMP2, or an agent or compound which inhibits the expression, transcription, or translation of EMP2 nucleic acids in a host cell. In some embodiments, the EMP2 *Chlamydia* inhibitors are provided in a composition also comprising a sterile carrier and/or physiologically acceptable carrier.

A "host cell" is a living cell which is capable of being infected with *Chlamydia* and expresses EMP2. Exemplary host cells are mammalian epithelial cells, including epithelial cells of the mucosa or eye. The host cells may be in vivo or in vitro.

Modulators are agents which can increase or decrease a referenced activity. Modulators include inhibitors and activators which have effects opposite to inhibitors (e.g., increase, stimulate, augment, enhance, accelerate) a referenced activity or entity.

The amino acid sequence of an EMP2 polypeptide according to the invention 1) comprises, consists of, or consists essentially of an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 15, 20, 25, 50, 75, 100, 125, 150 or more amino acids, to a polypeptide of SEQ ID NO:1 and 2) can either specifically bind to an antibody, e.g., polyclonal antibody, raised against an epitope of EMP2 or inhibit the ability of *Chlamydia* to enter a host cell expressing the EMP2 polypeptide of SEQ ID NO:1 or inhibit the infectivity of *Chlamydia*. In some embodiments, the EMP2 polypeptide is a fragment comprising, consisting of, or consisting essentially of the sequence of EMP2 from position 16 to 64, 20 to 60, 20 to 50, 20 to 40, or 30 to 64 or 40 to 64 of SEQ ID NO:1. In some embodiments, the EMP2 polypeptide is a fragment comprising, consisting of, or consisting essentially of the sequence of EMP2 from position 60 to 100, 80 to 150, 100 to 150, 110 to 140, 120 to 140, 50 to 150, or 100 to 160 of SEQ ID NO:1. In some embodiments, the EMP2 fragment comprises an epitope recognized by an anti-EMP2 antibody. In some embodiments of the invention's first aspect, the epitope recognized by an anti-EMP2 antibody inhibits the ability of *Chlamydia* to enter or bind a host cell expressing EMP2. In some embodiments of any of the above, the EMP2 fragment may be from 15 to 25, 15 to 40, 25 to 50, 50 to 100 amino acids long, or longer. In some embodiments, for either aspect, the EMP2 polypeptide is a polypeptide which binds a diabody having the KS49 or KS83 heavy and light chain sequences as disclosed herein.

An EMP2 polypeptide according to the invention may be a conservatively modified variant of a polypeptide of SEQ ID NO:1. Accordingly, in some embodiments of the above, the EMP polypeptide consists of the sequence of EMP2 of SEQ ID NO:1 or a fragment thereof. The fragment may be from 15 to 25, 15 to 40, 25 to 50, 50 to 100 amino acids long, or longer. The fragment may correspond to that of EMP2 from position 16 to 64 of SEQ ID NO:1. In other embodiments, the EMP2 polypeptide or fragment comprises a sequence of EMP2 of SEQ ID NO:1 or SEQ ID NO:2 having from 1, 2, 3, 4, or 5 conservative amino acid modifications or 1, 2, 3, 4, or 5 substitutions with a artificial chemical mimetic of the corresponding naturally occurring amino acid. The fragment may be from 15 to 25, 15 to 40, 25 to 50, 50 to 100 amino acids long, or longer. In some other embodiments still, the EMP2 polypeptide sequence can be that of a mammal including, but not limited to, primate, e.g., human; rodent, e.g., rat, mouse, hamster; cow, pig, horse, sheep. The proteins of the invention include both naturally occurring or recombinant molecules. In some embodiments, the amino acids of the EMP2 polypeptide are all naturally occurring amino acids as set forth below. In other embodiments, one or more amino acids may be substituted by an artificial chemical mimetic of a corresponding naturally occurring amino acids.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Methods for obtaining (e.g., producing, isolating, purifying, synthesizing, and recombinantly manufacturing) polypeptides are well known to one of ordinary skill in the art.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As to "conservatively modified variants" of amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

An "anti-EMP2 antibody" or "EMP2 antibody" according to the invention is an antibody which can bind to the EMP2 polypeptide of SEQ ID NO:1. In the first aspect of the invention, the antibodies according can act to inhibit the ability of *Chlamydia* to enter a host cell or cause infection. Without being wed to theory, it is believed that the antibodies act to inhibit the ability of *Chlamydia* to enter the host cell or cause an infection by reducing the availability of the host's endogenous EMP2 for interacting or binding with *Chlamydia*. The antibodies for use according to the invention in either aspect include, but are not limited to, recombinant antibodies, polyclonal antibodies, monoclonal antibodies, chimeric antibodies, human monoclonal antibodies, humanized or primatized monoclonal antibodies, and antibody fragments. The antibodies preferably bind to an external loop sequence of EMP2. In some embodiments, the antibodies bind to a polypeptide having the sequence of SEQ ID NO:2.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$—$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

Accordingly, in either aspect of the invention, the term antibody also embraces minibodies, diabodies, triabodies and the like. Diabodies are small bivalent biospecific antibody fragments with high avidity and specificity. Their high signal to noise ratio is typically better due to a better specificity and fast blood clearance increasing their potential for diagnostic and therapeutic targeting of specific antigen (Sundaresan et al., *J Nucl Med* 44:1962-9 (2003). In addition, these antibodies are advantageous because they can be engineered if necessary as different types of antibody fragments ranging from a small single chain Fv to an intact IgG with varying isoforms (Wu & Senter, *Nat. Biotechnol.* 23:1137-1146 (2005)). In some embodiments, the antibody fragment is part of a diabody. In some embodiments, in either aspect, the invention provides high avidity antibodies for use according to the invention.

The following human-origin antibody sequences encode for high-avidity antibodies specific for human (KS49, KS83) and mouse (KS83) EMP2 and have antibody variable region heavy and light chains suitable for use in either aspect of the invention:

```
KS49 heavy chain
                                                         (SEQ ID NO: 6)
M A Q V Q L V Q S G G G V V Q P G R S L R L S C A A S G F T F S S Y A M H W V R Q A P G K G L E W V A V I S Y D G S N K Y Y A D S V K G R F T I S R D N S K N T L Y L Q M N S L R

A E D T A V Y Y C A R D R R G R K S A G I D Y W G Q G T L V T V S S

KS49 light chain
                                                         (SEQ ID NO: 7)
D I Q M T Q S P S S L S A S V G D R V T I T C Q A S Q D I S N Y L N W Y Q Q K P G K A P K L L I Y A A S S L Q S G V P S R F S G S G S G T D F T L T I S S L Q P E D F A T Y Y C L Q D Y

N G W T F G Q G T K V D I K R A A A E Q K L I S E E D L N G A A

KS83 heavy chain
                                                         (SEQ ID NO: 8)
M A Q V Q L V E S G G G L V Q P G G S L R L S C A A S G F T F S S Y A M H W V R Q A P G K G L E W V A V I S Y D G S N K Y Y A D S V K G R F T I S R D N S K N T L Y L Q M N S L R

A E D T A V Y Y C A R T V G A T G A F D I W G Q G T M V T V S S S

KS83 light chain
                                                         (SEQ ID NO: 9)
D I V M T Q S P S T V S A S V G D R V I I P C R A S Q S I G K W L A W Y Q Q K P G K A P K L L I Y K A S S L E G W V P S R F S G S G S G T E F S L T I S S L Q P D D S A T Y V C Q Q S H

N F P P T F G G G T K L E I K R A A A E Q K L I S E E D L N G A A
```

Other diabodies for use according to either aspect of the invention include KS41 and KS89:

```
KS41
                                                         (SEQ ID NO.: 10)
M A Q V Q L V Q S G G G L V Q P G R S L R L S C A A S G F S F S E Y P M H W V R

Q A P G R G L E S V A V I S Y D G E Y Q K Y A D S V K G R F T I S R D D S K S T V

Y L Q M N S L R P E D T A V Y Y C A R T I N N G M D V W G Q G T T V T V S S

KS41
                                                         (SEQ ID NO.: 11)
D I V M T Q S P S S L S A S V G D R V T I T C R A S Q G I R N D L G W Y Q Q K P G

K A P E L L I Y G A S S L Q S G V P S R F S G S G S G T D F T L T I S S L Q P E D S A

T Y Y C L Q D Y N G W T F G Q G T K L E I K R A A A E Q K L I S E E D L N G A A

KS89
                                                         (SEQ ID NO.: 12)
M A Q V Q L V Q S G G G L V Q P G R S L R L S C A A S G F S F S E Y P M H W V R

Q A P G R G L E S V A V I S Y D G E Y Q K Y A D S V K G R F T I S R D D S K S T V

Y L Q M N S L R P E D T A V Y Y C A R T I N N G M D V W G Q G T T V T V S S

KS89
                                                         (SEQ ID NO.: 13)
D I V M T Q S P S S L S A S V G D R V T I T C R A S Q G I R N D L G W Y Q Q K P G

K A P E L L I Y G A S S L Q S G V P S R F S G S G S G T D F T L T I S S L Q P E D S A

T Y Y C L Q D Y N G W T F G Q G T K L E I K R A A A E Q K L I S E E D L N G A A
```

Anti-EMP-2 variable region sequences, used to encode proteins on backbones including for native antibody, fragment antibody, or synthetic backbones, can avidly bind EMP-2. Via this binding, these proteins can be used for EMP-2 detection, and to block EMP-2 function. Expression of these variable region sequences on native antibody backbones, or as an scFv, triabody, diabody or minibody, labeled with radionuclide, are particularly useful in the in vivo detection of EMP-2 bearing cells. Expression on these backbones or native antibody backbone are favorable for blocking the function of EMP-2 and/or killing EMP-2 bearing cells (e.g. gynecologic tumors) in vivo.

In some embodiments, the present invention provides anti-EMP-2 sequences comprising CDR regions of an antibody selected from KS49, KS83, KS41, and KS89, as shown in FIG. 24. The CDR regions provided by the invention may be used to construct an anti-EMP-2 binding protein, including without limitation, an antibody, a scFv, a triabody, a diabody, a minibody, and the like. In a certain embodiment, an anti-EMP-2 binding protein of the invention will comprise at least one CDR region from an antibody selected from KS49, KS83, KS41, and KS89. Anti-EMP-2 binding proteins may comprise, for example, a CDR-H1, a CDR-H2, a CDR-H3, a CDR-L1, a CDR-L2, a CDR-L3, or combinations thereof, from an antibody provided herein. In particular embodiments of the invention, an anti-EMP-2 binding protein may comprise all three CDR-H sequences of an antibody provided herein, all three CDR-L sequences of an antibody provided herein, or both. Anti-EMP2 CDR sequences may be used on an antibody backbone, or fragment thereof, and likewise may include humanized antibodies, or antibodies containing humanized sequences. These antibodies may be used, for example, to detect EMP-2, to detect cells expressing EMP-2 in vivo, or to block EMP-2 function. In some embodiments, the CDR regions may be defined using the Kabat definition, the Chothia definition, the AbM definition, the contact definition, or any other suitable CDR numbering system.

In some embodiments, the CDRs are as follows:

```
CDR 1 Heavy
                              (SEQ ID NO.: 14)
SYAMH (49)

(SEQ ID NO.: 14)
SYAMH (83)

(SEQ ID NO.: 15)
EYPMH (41)

(SEQ ID NO.: 15)
EYPMH (89)

CDR 2 Heavy
                              (SEQ ID NO.: 16)
```

-continued

```
VISYDGSNKYYADSVKG (49)

(SEQ ID NO.: 16)
VISYDGSNKYYADSVKG (83)

(SEQ ID NO.: 17)
VISYDGEYQKYADSVKG (41)

(SEQ ID NO.: 17)
VISYDGEYQKYADSVKG (89)

CDR 3 Heavy
                              (SEQ ID NO.: 39)
DRRGRKSAGIDY (49)

(SEQ ID NO.: 37)
TVGATGAFDI (83)

(SEQ ID NO.: 41)
TINNGMDV (41)

(SEQ ID NO.: 41)
TINNGMDV (89)

CDR 1 Light
                              (SEQ ID NO.: 18)
QASQDISNYLN (49)

(SEQ ID NO.: 19)
RASQSIGKWLA (83)

(SEQ ID NO.: 20)
RASQGIRNDLG (41)

(SEQ ID NO.: 20)
RASQGIRNDLG (89)

CDR 2 Light
                               (SEQ ID NO.: 21
AASSLQS (49)

(SEQ ID NO.: 22)
KASSLEG (83)

(SEQ ID NO.: 23)
GASSLQS (41)

(SEQ ID NO.: 23)
GASSLQS (89)

CDR 3 Light
                              (SEQ ID NO.: 40)
LQDYNGWT (49)

(SEQ ID NO.: 38)
QQSHNFPPT (83)

(SEQ ID NO.: 40)
LQDYNGWT (41)

(SEQ ID NO.: 40)
LQDYNGWT (89)
```

Diabody Sequence (KS49)

```
Heavy chain, KS49
                                                                   (SEQ ID NO.: 6)
M A Q V Q L V Q S G G G V V Q P G R S L R L S C A A S G F T F S S Y A M H W V R Q A P G K G L E W V A V I S Y D G S N K Y Y A D S V K G R F T I S R D N S K N T L

Y L Q M N S L R A E D T A V Y Y C A R D R R G R K S A G I D Y W G Q G T L V T V

S (SEQ ID NO.: 14)
CDR1 SYAMH
```

```
                                                     (SEQ ID NO.: 16)
CDR2 VISYDGSNKYYADSVKG

Light chain, KS49
                                                      (SEQ ID NO.: 7)
D I Q M T Q S P S S L S A S V G D R V T I T C Q A S Q D I S N Y L N W Y Q Q K P G K A P K L L I Y A A S S L Q S G V P S R F S G S G S G T D F T L T I S S L Q P E D F A

T Y Y C L Q D Y N G W T F G Q G T K V D I K R A A A E Q K L I S E E D L N G A A (SEQ ID NO.: 18)
CDR1 QASQDISNYLN (SEQ ID NO.: 21)
CDR2 AASSLQS
```

Diabody Sequence (KS83)

```
Heavy chain, KS83
                                                      (SEQ NO.: 8)
M A Q V Q L V E S G G G L V Q P G G S L R L S C A A S G F T F S S Y A M H W V R Q A P G K G L E W V A V I S Y D G S N K Y Y A D S V K G R F T I S R D N S K N T L

Y L Q M N S L R A E D T A V Y Y C A R T V G A T G A F D I W G Q G T M V T V S S (SEQ ID NO.: 14)
CDR1 SYAMH (SEQ ID NO.: 16)
CDR2 VISYDGSNKYYADSVKG

Light Chain, KS83
                                                      (SEQ ID NO.: 9)
D I V M T Q S P S T V S A S V G D R V I I P C R A S Q S I G K W L A W Y Q Q K P G K A P K L L I Y K A S S L E G W V P S R F S G S G S G T E F S L T I S S L Q P D D S A T

Y V C Q Q S H N F P P T F G G G T K L E I K R A A A E Q K L I S E E D L N G A A (SEQ ID NO.: 19)
CDR1 RASQSIGKWLA (SEQ ID NO.: 22)
CDR2 KASSLEG
```

Diabody Sequence (KS41)

```
Heavy Chain, KS41
                                                     (SEQ ID NO.: 10)
M A Q V Q L V Q S G G G L V Q P G R S L R L S C A A S G F S F S E Y P M H W V R Q A P G R G L E S V A V I S Y D G E Y Q K Y A D S V K G R F T I S R D D S K S T V

Y L Q M N S L R P E D T A V Y Y C A R T I N N G M D V W G Q G T T V T V S S (SEQ ID NO.: 15)
CDR 1 EYPMH (SEQ ID NO.: 17)
CDR 2 VISYDGEYQKYADSVKG

Light Chain, KS41
                                                     (SEQ ID NO.: 11)
D I V M T Q S P S S L S A S V G D R V T I T C R A S Q G I R N D L G W Y Q Q K P G K A P E L L I Y G A S S L Q S G V P S R F S G S G S G T D F T L T I S S L Q P E D S A

T Y Y C L Q D Y N G W T F G Q G T K L E I K R A A A E Q K L I S E E D L N G A A (SEQ ID NO.: 20)
CDR 1 RASQGIRNDLG
```

-continued

CDR 2 GASSLQS (SEQ ID NO.: 23)

Diabody Sequence (KS89)

Heavy Chain, KS89
(SEQ ID NO.: 12)
M A Q V Q L V Q S G G G L V Q P G R S L R L S C A A S G F S F S <u>E Y P Mt H</u> W V R Q A P G R G L E S V A <u>V I S Y D G E Y Q K Y A D S V K G</u> R F T I S R D D S K S T V

Y L Q M N S L R P E D T A V Y Y C A R T I N N G M D V W G Q G T T V T V S S

CDR1 EYPMH (SEQ ID NO.: 15)

CDR2 VISYDGEYQKYADSVKG (SEQ ID NO.: 17)

Light Chain, KS89
(SEQ ID NO.: 13)
D I V Met T Q S P S S L S A S V G D R V T I T C <u>R A S Q G I R N D L G</u> W Y Q Q K P G K A P E L L I Y <u>G A S S L Q S</u> G V P S R F S G S G S G T D F T L T I S S L Q P E D S A

T Y Y C L Q D Y N G W T F G Q G T K L E I K R A A A E Q K L I S E E D L N G A A

CDR1 RASQGIRNDLG (SEQ ID NO.: 20)

CDR2 GASSLQS (SEQ ID NO.: 23)

In some embodiments, the invention provides antibodies (e.g., diabodies, minibodies, triabodies) or fragments thereof having the CDRs of a diabody selected from KS49, KS83, KS41, and KS89. In some embodiments, these antibodies lack the polyhistine tag. In other embodiments, the diabodies possess the light and heavy chain of a KS49, KS83, KS41, or KS89 diabody. In still other embodiments, the antibodies are substantially identical in sequence to a diabody selected from the group consisting of KS49, KS83, KS41, and KS89 with or without the polyhistidine tag. In still other embodiments, the antibodies are substantially identical in sequence to the light and heavy chain sequences of a diabody selected from the group consisting of KS49, KS83, KS41, and KS89. These identities can be 65%, 70%, 75%, 80%, 85%, 90%, and preferably 91%, 92%, 93%, 94%, 95%, 96%, 97%, 98% or 99% or greater amino acid sequence identity. In some further embodiments of any of the above, the antibodies comprise CDRs sequences identical to those of the KS49, KS83, KS41, or KS89 diabody.

Diabodies, first described by Hollinger et al., PNAS (USA) 90(14): 6444-6448 (1993), may be constructed using heavy and light chains disclosed herein, as well as by using individual CDR regions disclosed herein. Typically, diabody fragments comprise a heavy chain variable domain ($V_H$) connected to a light chain variable domain ($V_L$) by a linker which is too short to allow pairing between the two domains on the same chain. Accordingly, the $V_H$ and $V_L$ domains of one fragment are forced to pair with the complementary $V_H$ and $V_L$ domains of another fragment, thereby forming two antigen-binding sites. Triabodies can be similarly constructed with three antigen-binding sites. An Fv fragment contains a complete antigen-binding site which includes a $V_L$ domain and a $V_H$ domain held together by non-covalent interactions. Fv fragments embraced by the present invention also include constructs in which the $V_H$ and $V_L$ domains are crosslinked through glutaraldehyde, intermolecular disulfides, or other linkers. The variable domains of the heavy and light chains can be fused together to form a single chain variable fragment (scFv), which retains the original specificity of the parent immunoglobulin. Single chain Fv (scFv) dimers, first described by Gruber et al., J. Immunol. 152(12):5368-74 (1994), may be constructed using heavy and light chains disclosed herein, as well as by using individual CDR regions disclosed herein. Many techniques known in the art can be used to prepare the specific binding constructs of the present invention (see, U.S. Patent Application Publication No. 20070196274 and U.S. Patent Application Publication No. 20050163782, which are each herein incorporated by reference in their entireties for all purposes, particularly with respect to minibody and diabody design).

Bispecific antibodies can be generated by chemical cross-linking or by the hybrid hybridoma technology. Alternatively, bispecific antibody molecules can be produced by recombinant techniques (see: bispecific antibodies). Dimerization can be promoted by reducing the length of the linker joining the VH and the VL domain from about 15 amino acids, routinely used to produce scFv fragments, to about 5 amino acids. These linkers favor intrachain assembly of the VH and VL domains. A suitable short linker is SGGGS (SEQ ID NO.: 24), but other linkers can be used. Thus, two fragments assemble into a dimeric molecule. Further reduction of the linker length to 0-2 amino acids can generate trimeric (triabodies) or tetrameric (tetrabodies) molecules.

Accordingly, this invention for the first time identifies the sequence of recombinant antibodies, thereby permitting production of recombinant anti-EMP2 on desirable backbones, and in therapeutically and diagnostically useful amounts. The KS83 and KS49 recombinant sequences have been constructed as in scFv, diabody, and native antibody formats. Sufficient protein amounts and purity have been achieved to document binding specificity in vitro. Cytolytic and tumor-ablative function of human ovarian, endometrial, and glioblastoma cell lines have been demonstrated in vitro and in vivo. The sequences are also useful when incorporated onto a suitable backbone in producing recombinant anti-EMP2 proteins (scFv, triabody, diabody, minibody, and native antibody formats) for imaging or in vivo therapy.

For preparation of antibodies, e.g., recombinant, monoclonal, or polyclonal antibodies, many techniques known in the art can be used (see, e.g., Kohler & Milstein, *Nature* 256:495-497 (1975); Kozbor et al., *Immunology Today* 4:72 (1983); Cole et al., in *Monoclonal Antibodies and Cancer Therapy*, Alan R. Liss, Inc., pp. 77-96 (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121: 210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Using Antibodies, A Laboratory Manual* (1998) for a description of immunoassay formats and conditions that can be used to determine specific immunoreactivity).

For example, rabbit polyclonal antibodies to EMP2 are known in the art (see, Wang et al., *Blood* 97:3890-3895 (2001)). Such antibodies may be obtained using glutathione-S-transferase-EMP2 fusion proteins. Rabbit antibodies can be generated against the first extracellular region of the gene (from amino acid 16 to 64) constructed as a glutathione-S-transferase (GST)-EMP2 fusion protein. The EMP2 peptide can be cloned by PCR using the following primers: CGC GGATCCTCTACCATTGACAATGCCTGG (SEQ ID NO.: 25) (forward; BamHI underlined); CCG GAATTCTTACGCCTGCATCACAGAATAACC (SEQ ID NO.: 26) (reverse, EcoRI underlined). The PCR product can be directionally cloned into the BamHI and EcoRI sites of the pGEX-4T-1 vector that contains GST gene (Pharmacia). The EMP2 fragment is cloned in frame with the GST to create a fusion protein. The insert can be confirmed by sequencing. The GST fusion protein can be produced as previously described (see, Smith D B et al., *Gene* 67:31-40 (1988)). Bacteria in log phase ($OD_{600}$ 0.6 to 0.9) can be induced for 2.5 to 3 hours at 37° C. with 1 mM isopropyl-1-thio-β-D-galactopyranoside. Bacteria are lysed, and the soluble fraction loaded onto a glutathione-Sepharose column (Pierce, Rockford, Ill.). The columns are washed with 10 bed volumes of phosphate-buffered saline (PBS)/EDTA. The fusion protein elutes from the column using 20 mM reduced glutathione (Sigma, St Louis, Mo.) in 50 mM Tris-Cl, pH 8.0. For antibody preparation, rabbits are immunized twice with the GST-EMP2 fusion protein, and serum is collected, starting 2 weeks after the last immunization (Research Genetics, Huntsville, Ala.).

Example 6 exemplifies an approach for obtaining fully human monoclonal antibodies to EMP2. These antibodies can be produced using recombinant phage-display technology from a human antibody phage-display gene library. Such monoclonal antibodies to human EMP2 can be used for diagnostic purposes, in cancer therapy, and as EMP2 Chlamydial inhibitors for prevention or treatment of *Chlamydia* infection. Monoclonal antibodies to mouse EMP2 can be similarly prepared for use in validating the therapeutic strategy in preclinical mouse models of cancer or *Chlamydia* infection in vivo.

In some embodiments, the invention provides an "EMP2 siRNA" for use in preventing, treating or inhibiting a *Chlamydia* infection or a cancer overexpressing EMP2. In this embodiment, the siRNA has a sequence which is complementary to that of SEQ ID NO:3 and is capable of reducing the expression of EMP2 in a target cell of the host.

An "siRNA" or "RNAi" refers to a nucleic acid that forms a double stranded RNA, which double stranded RNA has the ability to reduce or inhibit expression of a gene or target gene when the siRNA expressed in the same cell as the gene or target gene. "siRNA" or "RNAi" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 or about 24-29 nucleotides in length, e.g., 20, 21, 22, 23, 24, 25, 26, 27, 28, 29, or 30 nucleotides in length.

Figure 5:
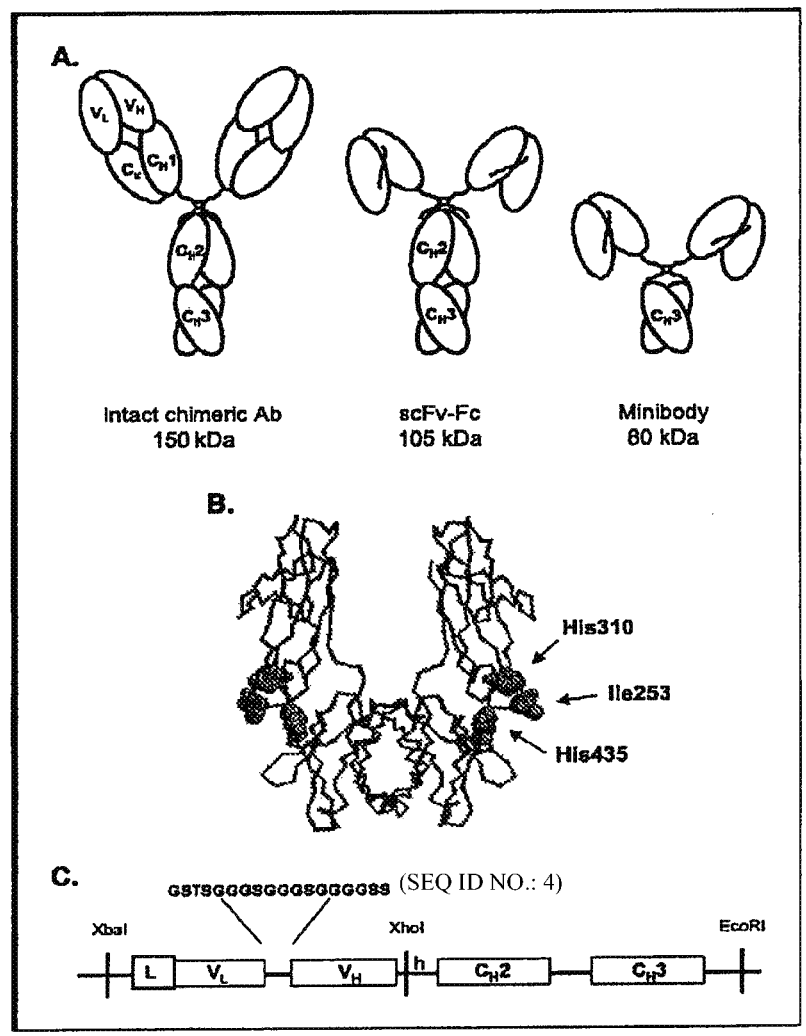
FIG. 5A-C. Depiction of a chimeric antibody for use according to the invention as may be made by use of phage display methodology.

The design and making of siRNA molecules and vectors are well known to those of ordinary skill in the art. For instance, an efficient process for designing a suitable siRNA is to start at the AUG start codon of the mRNA transcript (e.g., see, FIG. 5) and scan for AA dinucleotide sequences (see, Elbashir et al., *EMBO J* 20:6877-6888 (2001)). Each AA and the 3' adjacent nucleotides are potential siRNA target sites. The length of the adjacent site sequence will determine the length of the siRNA. For instance, 19 adjacent sites would give a 21 Nucleotide long siRNA siRNAs with 3' overhanging UU dinucleotides are often the most effective. This approach is also compatible with using RNA pol III to transcribe hairpin siRNAs. RNA pol III terminates transcription at 4-6 nucleotide poly(T) tracts to create RNA molecules having a short poly(U) tail. However, siRNAs with other 3' terminal dinucleotide overhangs can also effectively induce RNAi and the sequence may be empirically selected. For selectivity, target sequences with more than 16-17 contiguous base pairs of homology to other coding sequences can be avoided by conducting a BLAST search (see, www.ncbi.nlm.nih.gov/BLAST).

The siRNA can be administered directly or an siRNA expression vectors can be used to induce RNAi. A vector can have inserted two inverted repeats separated by a short spacer sequence and ending with a string of T's which serve to terminate transcription. The expressed RNA transcript is predicted to fold into a short hairpin siRNA. The selection of siRNA target sequence, the length of the inverted repeats that encode the stem of a putative hairpin, the order of the inverted repeats, the length and composition of the spacer sequence that encodes the loop of the hairpin, and the presence or absence of 5'-overhangs, can vary. A preferred order of the siRNA expression cassette is sense strand, short spacer, and antisense strand. Hairpin siRNAs with these various stem lengths (e.g., 15 to 30) are suitable. The length of the loops linking sense and antisense strands of the hairpin siRNA can have varying lengths (e.g., 3 to 9 nucleotides, or longer). The vectors may contain promoters and expression enhancers or other regulatory elements which are operably linked to the nucleotide sequence encoding the siRNA.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers. These control elements may be designed to allow the clinician to turn off or on the expression of the gene by adding or controlling external factors to which the regulatory elements are responsive.

In some embodiments, the EMP2 inhibitor is an EMP2 ribozyme which can inhibit the expression of EMP2 when present in a cell. Ribozymes are enzymatic RNA molecules capable of catalysing the specific cleavage of RNA. The mechanism of ribozyme action involves sequence specific hybridisation of the ribozyme molecule to complementary target RNA, followed by an endonucleolytic cleavage. Within the scope of the invention are engineered hammerhead motif ribozyme molecules that specifically and efficiently catalyse endonucleolytic cleavage of EMP2 mRNA, including particularly the mRNA of SEQ ID NO:3. Specific ribozyme cleavage sites within any potential RNA target are initially identified by scanning the target molecule for ribozyme cleavage sites, which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. Both anti-sense RNA and DNA molecules and ribozymes of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors, which incorporate suitable RNA polymerase promoters such as the T7 or SP6 polymerase promoters. Methods of making ribozymes are well known in the art (see, for instance, U.S. Patent Application Publication No. 20060062785).

Construction of suitable vectors for the EMP2 siRNA or EMP2 Ribozymes containing the desired EMP2 siRNA or EMP2 Ribozyme sequences and control sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and religated in the form desired.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

The terms "identical" or percent "identity," in the context of two or more nucleic acids or polypeptide sequences, including EMP2 siRNA and EMP2 polypeptides, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to the full length of the reference sequence, usually about 25 to 100, or 50 to about 150, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher et al., *J. Biol. Chem.* 273(52):35095-35101 (1998).

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic acid concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., John Wiley & Sons.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

The EMP2 antibody or EMP2 polypeptide according to the invention can have a label or detectable moiety attached thereto. A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "test compound" or "candidate molecule" or "modulator" or grammatical equivalents as used herein describes any molecule, either naturally occurring or synthetic, e.g., protein, polypeptide, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, RNAi, oligonucleotide, etc. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 Daltons and less than about 2500 Daltons, preferably less than about 2000 Daltons, preferably between about 100 to about 1000 Daltons, more preferably between about 200 to about 500 Daltons.

"Determining the functional effect" refers to assaying for a compound that increases or decreases a parameter that is indirectly or directly under the influence of a polynucleotide or polypeptide for use according to the invention, e.g., measuring physical and chemical or phenotypic effects. Such functional effects can be measured by any means known to those skilled in the art, e.g., changes in spectroscopic (e.g., fluorescence, absorbance, refractive index), hydrodynamic (e.g., shape), chromatographic, or solubility properties for the protein; measuring inducible markers or transcriptional activation of the protein; measuring binding activity or binding assays, e.g. binding to antibodies; measuring changes in ligand binding affinity; e.g., via chemiluminescence, fluorescence, colorimetric reactions, antibody binding, inducible markers, and ligand binding assays.

Samples or assays for identifying a EMP2 inhibitors of the invention are conducted in the presence of the candidate inhibitor and then the results are compared to control samples without the inhibitor to examine for the desired activity or to determine the functional effect of the candidate inhibitor. A positive reference control which is an agent having the desired activity may be used. In the case of EMP2 polypeptides, the positive control agent may be EMP2 itself. Control samples (untreated with inhibitors) are assigned a relative of 100%. Inhibition is achieved when the activity value relative to the control is about 80%, preferably 50%, more preferably 25 to 0%. Suitable methods for identifying inhibitors for use according to the invention are set forth in the Examples.

"Cancer" refers to human cancers and carcinomas, sarcomas, adenocarcinomas, lymphomas, leukemias, etc., including solid tumors and lymphoid cancers, kidney, breast, lung, kidney, bladder, colon, ovarian, prostate, pancreas, stomach, brain, head and neck, skin, uterine, testicular, esophagus, and liver cancer, lymphoma, including non-Hodgkin's and Hodgkin's lymphoma, leukemia, and multiple myeloma. "Urogenital cancer" refers to human cancers of urinary tract and genital tissues, including but not limited to kidney, bladder, urinary tract, urethra, prostrate, penis, testicle, vulva, vagina, cervical and ovary tissues. The cancers to be detected, diagnosed or treated herein express or overexpress EMP2. cancers which overexpress EMP2 include, but are not limited to, endometrial cancer, ovarian cancer, glioblastoma, breast cancer, prostate cancer, testicular cancer, and myeloma.

In one embodiment of the invention's second aspect, a diagnostic or prognostic assay will be performed to determine whether the patient's cancer is characterized by overexpression of EMP2. Various assays for determining such amplification/overexpression are contemplated and include the immunohistochemistry, FISH and shed antigen assays, southern blotting, or PCR techniques. Moreover, the EMP2 overexpression or amplification may be evaluated using an in vivo diagnostic assay, e.g. by administering a molecule (such as an antibody) which binds the molecule to be detected and is tagged with a detectable label (e.g. a radioactive isotope) and externally scanning the patient for localization of the label. In some embodiments, the cancer to be treated is not yet invasive, but overexpresses EMP2.

"Therapy resistant" cancers, tumor cells, and tumors refers to cancers that have become resistant or refractory to either or both apoptosis-mediated (e.g., through death receptor cell signaling, for example, Fas ligand receptor, TRAIL receptors, TNF-R1, chemotherapeutic drugs, radiation) and non-apoptosis mediated (e.g., toxic drugs, chemicals) cancer therapies, including chemotherapy, hormonal therapy, radiotherapy, and immunotherapy. The invention contemplates treatment of both types.

"Overexpression" refers to RNA or protein expression of EMP2 in a tissue that is significantly higher that RNA or protein expression of in a control tissue sample. In one embodiment, the tissue sample is autologous. Cancerous test tissue samples associated with invasiveness, metastasis, hormone independent (e.g., androgen independence), or refractoriness to treatment or an increased likelihood of same typically have at least two fold higher expression of EMP2 mRNA or protein, often up to three, four, five, eight, ten or more fold higher expression of EMP2 protein in comparison to cancer tissues from patients who are less likely to progress to metastasis or to normal (i.e., non-cancer) tissue samples. Such differences may be readily apparent when viewing the bands of gels with approximately similarly loaded with test and controls samples. Prostate cancers expressing increased amounts of EMP2 are more likely to become invasive, metastasize, or progress to treatment refractory cancer. Various cutoffs are pertinent for EMP2 overexpression, since it is possible that a small percentage of EMP2 positive cells in primary tumors may identify tumors with a high risk for recurrence and metastasis. The terms "overexpress," "overexpression" or "overexpressed" interchangeably refer to a gene that is transcribed or translated at a detectably greater level, usually in a cancer cell, in comparison to a normal cell of the same type. Overexpression therefore refers to both overexpression of protein and RNA (due to increased transcription, post transcriptional processing, translation, post translational processing, altered stability, and altered protein degradation), as well as local overexpression due to altered protein traffic patterns (increased nuclear localization), and augmented functional activity, e.g., as in an increased enzyme hydrolysis of substrate. Overexpression can also be by 50%, 60%, 70%, 80%, 90% or more (2-fold, 3-fold, 4-fold) in comparison to a non-cancerous cell of the same type. The overexpression may be based upon visually detectable or quantifiable differences observed using immunohistochemical methods to detect EMP2 protein or nucleic acid.

The terms "cancer that overexpresses EMP2" and "cancer associated with the overexpression of EMP2" interchangeably refer to cancer cells or tissues that overexpress EMP2 in accordance with the above definition.

The terms "cancer-associated antigen" or "tumor-specific marker" or "tumor marker" interchangeably refers to a molecule (typically protein, carbohydrate or lipid) that is preferentially expressed in a cancer cell in comparison to a normal cell, and which is useful for the preferential targeting of a pharmacological agent to the cancer cell. A marker or antigen can be expressed on the cell surface or intracellularly. Oftentimes, a cancer-associated antigen is a molecule that is overexpressed or stabilized with minimal degradation in a cancer cell in comparison to a normal cell, for instance, 2-fold overexpression, 3-fold overexpression or more in comparison to a normal cell. Oftentimes, a cancer-associated antigen is a molecule that is inappropriately synthesized in the cancer cell, for instance, a molecule that contains deletions, additions or mutations in comparison to the molecule expressed on a normal cell. Oftentimes, a cancer-associated antigen will be expressed exclusively in a cancer cell and not synthesized or expressed in a normal cell.

Compositions.

When used for pharmaceutical purposes with regard to either aspect of the invention, the EMP2 inhibitors used according to the invention are typically formulated in a suitable buffer, which can be any pharmaceutically acceptable buffer, such as phosphate buffered saline or sodium phosphate/sodium sulfate, Tris buffer, glycine buffer, sterile water, and other buffers known to the ordinarily skilled artisan such as those described by Good et al., *Biochemistry* 5:467 (1966). The compositions can additionally include a stabilizer, enhancer, or other pharmaceutically acceptable carriers or vehicles. A pharmaceutically acceptable carrier can contain a physiologically acceptable compound that acts, for example, to stabilize the nucleic acids or polypeptides of the invention and any associated vector. A physiologically acceptable compound can include, for example, carbohydrates, such as glucose, sucrose or dextrans; antioxidants, such as ascorbic acid or glutathione; chelating agents; low molecular weight proteins or other stabilizers or excipients. Other physiologically acceptable compounds include wetting agents, emulsifying agents, dispersing agents, or preservatives, which are particularly useful for preventing the growth or action of microorganisms. Various preservatives are well known and include, for example, phenol and ascorbic acid. Examples of carriers, stabilizers, or adjuvants can be found in *Remington's Pharmaceutical Sciences, Mack Publishing Company, Philadelphia, Pa.*, 17th ed. (1985).

The pharmaceutical compositions according to the invention comprise a therapeutically effective amount of a EMP2 inhibitor (e.g., EMP2-polypeptide, anti-EMP2 antibody, EMP2 si RNA, or EMP2 ribozyme) according to the invention and a pharmaceutically acceptable carrier. By "therapeutically effective dose or amount" herein is meant a dose that produces effects for which it is administered (e.g., treatment or prevention of a *Chlamydia* infection). The exact dose and formulation will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); *Remington: The Science and Practice of Pharmacy*, 20th Edition, Gennaro, Editor (2003), and Pickar, *Dosage Calculations* (1999)). The EMP2 *Chlamydia* inhibitor, if a salt, is formulated as a "pharmaceutically acceptable salt."

A "pharmaceutically acceptable salt" or to include salts of the active compounds which are prepared with relatively nontoxic acids or bases, according to the route of administration. When inhibitors of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Aside from biopolymers such as nucleic acids and polypeptides, certain compounds of the present invention possess asymmetric carbon atoms (optical centers) or double bonds; the racemates, diastereomers, geometric isomers and individual isomers are all intended to be encompassed within the scope of the present invention. In preferred embodiments, wherein the compound comprises amino acids or nucleic acids, the amino acids and nucleic acids are each the predominant naturally occurring biological enantiomer.

The compositions for administration will commonly comprise an agent as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

Suitable formulations for use in the present invention are found in *Remington: The Science and Practice of Pharmacy*, 20th Edition, Gennaro, Editor (2003) which is incorporated herein by reference. Moreover, for a brief review of methods for drug delivery, see, Langer, Science 249:1527-1533 (1990), which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the compounds of the present invention can be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the inhibitors for use according to the invention can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

In some embodiments, a pharmaceutical composition for intravenous administration may provide from about 0.1 to 100 mg per patient per day. Dosages from 0.1 up to about 100 mg per patient per day may be used. Substantially higher dosages are possible in topical administration. Actual methods for preparing parenterally administrable compositions will be known or apparent to those skilled in the art and are described in more detail in such publications as *Remington: The Science and Practice of Pharmacy,* 21st Edition 2005, Lippincott Williams & Wilkins, Publishers.

The pharmaceutical compositions can be administered in a variety of dosage forms and amounts depending upon the method of administration. For example, unit dosage forms suitable for oral administration include, but are not limited to, powder, tablets, pills, capsules and lozenges. It is recognized that antibodies when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

Pharmaceutical formulations, particularly, of the polypeptide and nucleic acid EMP2 inhibitors for according to the present invention can be prepared by mixing an antibody having the desired degree of purity with optional pharmaceutically acceptable carriers, excipients or stabilizers. Such formulations can be lyophilized formulations or aqueous solutions. Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid) preservatives low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e.g. Zn-protein complexes); and/or non-ionic surfactants. The antibody can be formulated at a concentration of between 0.5-200 mg/ml, or between 10-50 mg/ml.

The compositions containing the EMP2 inhibitors of the invention (e.g., anti-EMP2 antibodies and EMP2 polypeptides) can be administered for therapeutic or prophylactic treatments. In therapeutic applications, compositions are administered to a patient in a "therapeutically effective dose." Single or multiple administrations of the compositions may be administered depending on the dosage and frequency as required and tolerated by the patient. A "patient" or "subject" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human.

The pharmaceutical compositions can comprise additional active agents, including any one or more of the following, analgesics, anti-inflammatories, antibiotics, antimicrobials, lubricants, contraceptives, spermicides, local anesthetics, and anti-puritics.

As used herein, the term "carrier" refers to a typically inert substance used as a diluent or vehicle for an active agent to be applied to a biological system in vivo or in vitro. (e.g., drug such as a therapeutic agent). The term also encompasses a typically inert substance that imparts cohesive qualities to the composition.

In some embodiments, the invention provides a composition comprising an EMP2 inhibitor and a physiologically acceptable carrier at the cellular or organismal level. Typically, a physiologically acceptable carrier is present in liquid, solid, or semi-solid form. Examples of liquid carriers include physiological saline, phosphate buffer, normal buffered saline (135-150 mM NaCl), water, buffered water, 0.4% saline, 0.3% glycine, glycoproteins to provide enhanced stability (e.g., albumin, lipoprotein, globulin, etc.), and the like. Examples of solid or semi-solid carriers include mannitol, sorbitol, xylitol, maltodextrin, lactose, dextrose, sucrose, glucose, inositol, powdered sugar, molasses, starch, cellulose, microcrystalline cellulose, polyvinylpyrrolidone, acacia gum, guar gum, tragacanth gum, alginate, extract of Irish moss, panwar gum, ghatti gum, mucilage of isapol husks, Veegum®, larch arabogalactan, gelatin, methylcellulose, ethylcellulose, carboxymethylcellulose, hydroxypropylmethylcellulose, polyacrylic acid (e.g., Carbopol), calcium silicate, calcium phosphate, dicalcium phosphate, calcium sulfate, kaolin, sodium chloride, polyethylene glycol, and combinations thereof. Since physiologically acceptable carriers are determined in part by the particular composition being administered as well as by the particular method used to administer the composition, there are a wide variety of suitable formulations of pharmaceutical compositions of the present invention (see, e.g., *Remington's Pharmaceutical Sciences*, 17$^{th}$ ed., 1989). The carriers and compositions are preferably sterile.

The compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically or physiologically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate.

Formulations suitable for oral administration can comprise: (a) liquid solutions, such as an effective amount of a packaged platinum-based drug suspended in diluents, e.g., water, saline, or PEG 400; (b) capsules, sachets, or tablets, each containing a predetermined amount of a platinum-based drug, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise an EMP2 *Chlamydia* inhibitor in a flavor, e.g., sucrose, as well as pastilles comprising a polypeptide or peptide fragment in an inert base, such as gelatin and glycerin or sucrose and acacia emulsions, gels, and the like, containing, in addition to the inhibitor, carriers known in the art.

Topical Compositions

In either the first or second aspect, the present invention provides topical pharmaceutical compositions comprising an EMP2 inhibitor according to the invention. More preferably, the inhibitor is a small organic compound, an EMP2 polypeptide, or anti-EMP2 antibody. The inhibitor may be in a unit dosage form comprising per unit dosage an amount of a EMP2 inhibitor as provided above which is effective for treating cancer or inhibiting infection by *Chlamydia*.

Also provided, in the first aspect, are methods of treating *Chlamydia* infections by topically administering an effective amount of such compositions (e.g., in unit dosage form) to, or proximal to, the affected area.

In either aspect, topical formulations of EMP2 inhibitors may be formulated in combination with a pharmaceutically acceptable carrier. Dosage forms for the topical administration of the compounds of this invention include powders, sprays, foams, jellies, ointments, pastes, creams, lotions, gels, solutions, patches, suppositories and liposomal preparations. The dosage forms may be formulated with mucoadhesive polymers for sustained release of active ingredients at the urogenital area. The active compound may be mixed under sterile conditions with a pharmaceutically acceptable carrier, and with any preservatives, buffers, or propellants, which may be required. Topical preparations can be prepared by combining the inhibitor t with conventional pharmaceutical diluents and carriers commonly used in topical dry, liquid, cream and aerosol formulations. Ointment and creams may, for example, be formulated with an aqueous or oily base with the addition of suitable thickening and/or gelling agents. Such bases may include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, and the like. Lotions may be formulated with an aqueous or oily base and, in general, also include one or more of the following: stabilizing agents, emulsifying agents, dispersing agents, suspending agents, thickening agents, coloring agents, perfumes, and the like. Powders may be formed with the aid of any suitable powder base, e.g., talc, lactose, starch, and the like. Drops may be formulated with an aqueous base or nonaqueous base also comprising one or more dispersing agents, suspending agents, solubilizing agents, and the like.

The ointments, pastes, creams and gels also may contain excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays also can contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

In either aspect, the EMP2 inhibitor can be formulated with a pharmaceutically acceptable carrier and at least one of the following second pharmacologic agents: a local anesthetic (e.g., lidocaine, prilocalne, etc.), local anti-inflammatory agent (e.g., naproxen, pramoxicam, etc.), corticosteroid (e.g., cortisone, hydrocortisone, etc.), anti-itch agent (e.g., loperamide, diphylenoxalate, etc.), an agent that interferes with the activation of peripheral sensory neurons, including divalent and trivalent metal ions (e.g., manganese, calcium, strontium, nickel, lanthanum, cerium, zinc, etc.), analgesic agents, a lubricant, yeast-based product (e.g., lyophilized yeast, yeast extract, etc.), a spermicide, growth-promoting and/or wound healing-promoting agent known to promote re-epithelialization (e.g., platelet-derived growth factor (PDGF), interleukin- 11 (IL-11), etc.), anti-microbial agent (e.g., Neosporin, polymyxin B sulfate, bacitracin zinc, etc.), mucoadhesive agent (e.g., cellulose derivatives, etc.), cytoprotectant agent (e.g., colloidal bismuth, misoprostol, sucralfate, etc.) as defined in Goodman and Gilman, *The Pharmacological Basis of Therapeutics*, or menthol.

In the first aspect, the EMP2 *Chlamydia* inhibitor may be present in the composition in unit dosage form effective for the treatment of the *Chlamydia* infection. The at least one second pharmacological compound is typically present in the composition in unit dosage effective for the treatment of a condition(s), symptom(s) or effect(s) associated with or resulting from the *Chlamydia* infection or activity related to its transmission. The topical pharmaceutical compositions also can contain other active ingredients such as antimicrobial agents, particularly antibiotics, anesthetics, analgesics, contraceptive agents, lubricants, spermicides, and antipruritic agents. The topical pharmaceutical compositions can also include one or more preservatives or bacteriostatic agents, e.g., methyl hydroxybenzoate, propyl hydroxybenzoate, chlorocresol, benzalkonium chlorides, and the like. The topical composition may be applied with an applicator, may be coated on either or both surfaces of a condom or diaphragm or other contraceptive device. Particularly preferred antibiotics are those conventionally used to treat a *Chlamydia* infection.

In either aspect of the invention, the dosage of a EMP2 inhibitor depends upon many factors that are well known to those skilled in the art, for example, the particular compound; the condition being treated; the age, weight, and clinical condition of the recipient patient; and the experience and judgment of the clinician or practitioner administering the therapy. An effective amount of the compound is that which provides either subjective relief of symptoms or an objectively identifiable improvement as noted by the clinician or other qualified observer. The dosing range varies with the compound used, the route of administration and the potency of the particular compound.

In either aspect, the invention provides topical sustained and prolonged release pharmaceutical compositions comprising one or more pharmacological compounds described supra, and a pharmaceutically acceptable carrier, to treat a *Chlamydia* infection. Preferably, the compositions are administered in unit dosage form to a subject in need of such treatment. Topical sustained and prolonged release compositions are typically variants which include 1) an absorbent in a hydrophilic base; 2) an absorbent in a hydrophobic base; and 3) coated beads containing an absorbent matrix dispersed in a suitable vehicle.

Such hydrophilic compositions and preparations of the invention comprise a compound of the invention and a polymer, such as cellulose (methyl cellulose, ethyl cellulose, hydroxy propyl cellulose, etc.), higher molecular weight polyethylene glycol, methacrylic-acrylic acid emulsion, hydrogel, carbopol, ethyl vinyl acetate copolymer, or polyester, etc., to bind the compound of interest to the polymer. The compound-polymer matrix is then dispersed in a hydrophilic vehicle to form a semi-solid. After administration of such hydrophilic composition into the appropriate urogenital area, such as, e.g., the vagina or urethral tract, the water in the semi-solid preparation is adsorbed and the polymer matrix with the active ingredient (i.e., the pharmaceutical compound) remains as a coating in the area to which it has been applied. The pharmaceutical compound is then slowly released from this coating.

Hydrophobic compositions and preparations of the invention employ similar polymers as used in the hydrophilic preparations, but the polymer/compound matrix is dispersed into a vehicle, such a plastibase, in the hydrophobic compositions and preparations. Plastibase is a mineral oil base that only partially dissolves the pharmaceutical compound. The semi-solid composition forms a thin coating on the urogenital region to which the composition has been applied (such as, e.g., the vagina or urethral tract) and slowly releases the active compound. The prolonged action is controlled principally by the solubility of the active ingredient in the vehicle.

The present invention also provides coated beads which are produced by first absorbing a compound of the present invention, or a combination of compounds, on a cellulosic material blended with polyethylene glycol, filler, binder and other excipients. The resulting matrix is then extruded and spheronized (e.g., the process of making into spheres) to create small beads. The beads are then coated to an appropriate thickness with one or more of a suitable material, such as a methacrylic-acrylic polymer, polyurethane, ethyl vinyl acetate copolymer, polyester, silastic, etc. The coating on the beads acts as a rate controlling membrane that regulates the release of the compound from the core beads.

Methods of Treatment

In both aspects, the terms "treating" or "treatment" includes:

(1) preventing the disease, i.e., causing the clinical symptoms of the disease not to develop in a mammal that may be exposed to the organism but does not yet experience or display symptoms of the disease, (2) inhibiting the disease, i.e., arresting or reducing the development of the disease or its clinical symptoms. In its first aspect, this includes eliminating the infection or reducing the numbers of *Chlamydia* in the subject or infected tissue.

(3) relieving the disease, i.e., causing regression of the disease or its clinical symptoms.

In either aspect, the EMP2 inhibitors and pharmaceutical compositions according to the invention may be administered by any route of administration (e.g., intravenous, topical, intraperitoneal, parenteral, oral, intravaginal, rectal, occularly). They may be administered as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred. The administration may be local or systemic. They may be administered to a subject who has been diagnosed with the subject disease (e.g., cancer or a *Chlamydia* infection), a history of the disease, or is at risk of the disease (e.g., engages in activities wherein the disease is exposure to *Chlamydia* may occur). They may be administered to a subject whose disease has been difficult to control or recurs after conventional or main-stay therapy.

In the first aspect, they may be administered in conjunction with conventional antibiotic therapy for *Chlamydia* or with contraceptive agents. In some embodiments, the methods include the step of first diagnosing the subject as having a *Chlamydia* infection and then administering the EMP2 *Chlamydia* inhibitor according to the invention. In some further embodiments, the diagnosis is achieved as described below.

In some embodiments, the EMP2 *Chlamydia* inhibitors are used to treat chronic pelvic pain syndromes in a subject with *Chlamydia* infection. The inhibitors in some other embodiments are used to treat ocular infections with *Chlamydia* or trachoma, the primary cause of infectious blindness worldwide. In yet other embodiments, the inhibitors are used to treat inflammatory diseases (e.g., arthritis, arteriosclerosis) in a subject having a *Chlamydia* infection.

In the second aspect, the siRNA and ribozyme EMP2 inhibitor formulations of the invention may be administered to a cell. The cell can be provided as part of a tissue, such as an epithelial membrane, or as an isolated cell, such as in tissue culture. The cell can be provided in vivo, ex vivo, or in vitro. The formulations can be introduced into the tissue of interest in vivo or ex vivo by a variety of methods. In some embodiments of the invention, the nucleic acids of the invention are introduced into cells by such methods as microinjection, calcium phosphate precipitation, liposome fusion, or biolistics. In further embodiments, the nucleic acids are taken up directly by the tissue of interest.

Diagnosis of *Chlamydia* Infection

Diagnosis is based upon symptoms and detection of the bacteria in body fluids or samples as is known to one of ordinary skill in the art. The traditional method of diagnosis is inoculation of monolayer cell culture with clinical specimens, followed by staining and visual examination after 2-3 days. Another more routine method requires the measurement of antichlamydial antibody titer changes in the paired sera (four fold greater rise in titer) and has a low predictive value for ongoing infection. Direct tests such as ELISA and IF (immunofluorescence) are easier to perform and require less time and labor than culturing of the organism. These methods directly measure *Chlamydia* antigens. The antigens used for the serological identification and differentiation of Chlamydiae are cell envelope antigens which are species specific. This antigens can distinguish *C. trachomatis, C. psittaci* and *C. pneumoniae* and among the 15 serovars of *C. trachomatis* (serovar specific antigens). (see, for instance, Black, C. M., *Clin Microbiol Rev* 10: 160-184 (1997)). In addition, DNA amplification methods are commercially available for the detection of *Chlamydia* specific RNA and DNA in body fluids.

Assays in the Diagnosis or Prognosis of Cancers which Express or Over-Express EMP2

The methods described herein involves measuring levels of EMP2 expression. Levels of EMP2 can be determined in a number of ways when carrying out the various methods of the invention. Various measurements of the level of EMP2 can be used for example, in terms of number of EMP2-positive cells per 100 cells in the tissue sample. Another measurement of the level of EMP2 is a measurement of the change in the level of EMP2 over time. These measurements may be expressed in an absolute amount or may be expressed in terms of a percentage increase or decrease over time, in one particularly important measurement, the level of EMP2 is measured in relation to levels in a control cell or gland sample.

Levels of EMP2 are advantageously compared to controls according to the invention. The control maybe a predetermined value, which can take a variety of forms. It can be a single cut-off value, such as a median or mean. It can be established based upon comparative groups, such as in groups not having elevated unopposed estrogen levels and groups having elevated unopposed estrogen levels. Another example of comparative groups would be groups having a particular disease, condition or symptoms and groups without the disease, condition or symptoms such as a group with premalignancy or cancer and a group without premalignancy or cancer. Another comparative group would be a group with a family history of a condition such as cancer and a group without such a family history. The predetermined value can be arranged, for example, where a tested population is divided equally (or unequally) into groups, such as a low-risk group, a medium-risk group and a high-risk group or into quadrants or quintiles, the lowest quadrant or quintile being individuals with the lowest risk or highest amount of EMP2 and the highest quadrant or quintile being individuals with the highest risk or lowest amount of EMP2.

Still other controls can be based on other cells or glands within a single tissue sample. For example, endometrial glands that express EMP2 may be located adjacent to endometrial glands that express reduced levels of EMP2. These glands that express EMP2 can serve as positive controls for comparison with glands having reduced EMP2 antibody staining. Likewise, stromal and other cells in an endometrial tissue sample will express EMP2 and can be used as controls.

The predetermined value of a control will depend upon the particular population selected. For example, an apparently healthy population will have a different "normal" range than will a population which is known, for instance, to have a condition related to endometrial premalignancy, endometrial cancer, or elevated unopposed estrogen levels. Accordingly, the predetermined value selected may take into account the category in which an individual falls. Appropriate ranges and categories can be selected with no more than routine experimentation by those of ordinary skill in the art. By "elevated" it is meant high relative to a selected control. Typically the control will be based on apparently healthy normal individuals in an appropriate age bracket.

It will also be understood that the controls according to the invention may be, in addition to predetermined values, samples of materials tested in parallel with the experimental materials. Examples include samples from control populations or control samples generated through manufacture to be tested in parallel with the experimental samples. As used herein a "matched" control means tissue or cells obtained at the same time from the same subject, for example, parts of a single biopsy, or parts of a single cell sample from the subject.

In a related aspect, the clinical populations can be analyzed by various statistical methods, including, but not limited to, multivariate analysis (see, e.g., Turner et al., *J Clin Oncol* 19(4):992-1000 (2001)). Further, such analysis may include survival analysis and other techniques for elucidating clinical data (see, e.g., Klein and Moeschberger, *Survival Analysis: Techniques for Censored and Truncated Data*, 2003, Springer-Verlag Publishing Co., New York, N.Y.).

The various assays used to determine the levels of EMP2 include: specific binding assays, using materials which bind specifically to EMP2; gel electrophoresis; and the like. Immunoassays may be used according to the invention including sandwich-type assays, competitive binding assays, one-step direct tests and two-step tests such as described herein. Preferably EMP2 levels are determined by nondestructive imaging of EMP2 expression, in preferred embodiments, the imaging is real-time imaging and/or permits visualization of EMP2 distribution.

As disclosed herein, it is also possible to assess likelihood of premalignancy by monitoring changes in the absolute or relative amounts of EMP2 over time. For example, an increase in EMP2 expression in individual endometrial glands correlates with increasing likelihood of endometrial premalignancy arising in such glands. Accordingly one can monitor EMP2 expression over time to determine if the likelihood of endometrial premalignancy in a subject is changing. Increases in relative or absolute EMP2 may indicate an abnormality, for example an onset or progression of endometrial premalignancy or endometrial cancer. Decreases in amounts of EMP2 expressed in endometrial glands over time may indicate a decrease in premalignancy or endometrial cancer remission or regression.

The invention in another aspect provides a diagnostic method to determine the effectiveness of treatments. The "evaluation of treatment" as used herein, means the comparison of a subject's levels of EMP2 measured in samples collected from the subject at different sample times, preferably at least 1 month apart following treatment. The preferred time to obtain the second sample from the subject is at least one month after obtaining the first sample, which means the second sample is obtained at any time following the day of the first sample collection, preferably at least 30, 45, 60 or more days after the time of first sample collection.

The comparison of levels of EMP2 in two or more samples, taken on different days, allows evaluation of disease progression or regression and of the effectiveness of anticancer treatment. The comparison of a subject's levels of EMP2 measured in samples obtained on different days provides a measure to determine the effectiveness of any treatment to avoid or eliminate a premalignancy.

As will be appreciated by those of ordinary skill in the art, the evaluation of the treatment also may be based upon an evaluation of the symptoms or clinical end-points of the associated disease. Thus, the methods of the invention also provide for determining the regression, progression, or onset of a condition which is characterized by increased levels of EMP2. In some instances, the subjects to which the methods of the invention are applied are already diagnosed as having a particular condition or disease. In other instances, the measurement will represent the diagnosis of the condition or disease, in some instances, the subjects will already be undergoing therapy for premalignancy or cancer, while in other instances the subjects will be without present therapy for premalignancy or cancer.

Accordingly, the present invention relates to alterations in EMP2 expression and disorders of EMP2 regulation which play a role in the pathogenesis of cancer (e.g, endometrial premalignancies, and ultimately in the development of endometrial cancer (EC)). By correlating alterations in the expression of EMP2 with disease status, EMP2 is disclosed as a useful biological marker for diagnosis, staging, imaging, and as a therapeutic target for the treatment of cancers which express or overexpress EMP2 (e.g., the premalignant endometrial phenotype and EC).

In one embodiment, a method is disclosed for determining the likelihood of a group of cells becoming cancerous, including determining the level of EMP2 polypeptide in a test sample, where increased levels of EMP2 polypeptide in the test sample relative to a control sample correlates with the cells having an increased likelihood of becoming cancerous. Thus, the invention provides a method for determining whether a subject has or is at risk of having cancer wherein the cancer is of a kind associated with the over-expression of EMP2.

In a related aspect, immunohistochemistry is performed, where the level of EMP2 expression is determined by antibody binding. In one aspect, the antibody binds to an amino acid sequence of EMP2. In a further related aspect, determining the frequency of detecting EMP2 in a sample and comparing the frequency of detection with multiple variables to generate multivariate models for the identification of variables demonstrating statistical significance for patient survival is disclosed, where such variables include ER, PR, vascular, stage, diagnosis, disease status, and survival status.

In another embodiment, a method for monitoring the progression of premalignancy in a subject is disclosed including determining the level of EMP2 polypeptide in cells obtained at a first time, determining the level of EMP2 polypeptide in cells obtained at a second time, and comparing the levels of EMP2 polypeptide the cells at the first and second times, where increased levels of EMP2 polypeptide at the second time relative to the first time correlates with progression of premalignancy to a cancerous stage.

In one embodiment, a method of monitoring the stage of cancer in a subject is disclosed, including identifying a subject presenting cancer, determining EMP2 polypeptide level in a sample of tissue from the subject to establish a baseline EMP2 level for the subject, measuring EMP2 polypeptide level in an endometrial tissue sample obtained from the same subject at subsequent time points, and comparing the measured EMP2 polypeptide level with the baseline EMP2 polypeptide level, where an increase in measured EMP2 polypeptide levels in the subject versus baseline EMP2 polypeptide levels is associated with a cancer which is progressing, and where a decrease in measured EMP2 polypeptide levels versus baseline EMP2 polypeptide level is associated with a cancer which is regressing or in remission.

In another embodiment, a method for screening a candidate compound that affects the premalignant phenotype is disclosed, including culturing tissue or cells, determining the level of EMP2 polypeptide in the cultured tissue or cells at a first time point, contacting the cultured tissue or cells with a candidate compound, determining the level of EMP2 polypeptide in the cultured tissue or cells subsequent to compound contact, and comparing the levels of EMP2 before and after compound contact, where a change in the amount of binding after compound contact correlates with a compound induced alteration in the level of EMP2.

In a related aspect, an increase in the level of EMP2 correlates with the onset of or progression of an premalignant cell phenotype. In a further related aspect, a decrease in the level of EMP2 correlates with the regression of an premalignant phenotype.

In one aspect, the candidate compound is a modulator of a progesterone receptor DNA binding domain, NF-κB, a serum response element, or PPAR.

In some embodiments, the cancer is one which overexpresses EMP2 relative to the non-cancerous state. EMP2 is overexpressed in a number of classes of tumor, including endometrial cancer, ovarian cancer, glioblastoma, breast cancer, prostate cancer, testicular cancer, and myeloma. In some preferred embodiments of any of the above, the antibody used is a diabody (e.g., KS49, KS83, KS41, KS89) as disclosed herein. PCT Patent Publication No. WO 2006/094014 which describes the use of antibodies in detection of EMP2 in the context of endometrial cancer is incorporated herein by reference with respect to the technologies used to detect target molecules in vivo, and particularly, with respect to endometrial cancer. In some embodiments of the second aspect, the subject cancer which expresses or overexpresses EMP2 is not endometrial cancer and/or the subject tissue is not endometrium.

In some embodiments, the invention provides a method for determining the likelihood of an endometrial cell becoming cancerous, comprising: determining the level of endothelial membrane protein 2 polypeptide in a test sample, wherein increased levels of EMP2 polypeptide in the test sample relative to a control sample correlates with the cells having an increased likelihood of becoming cancerous. In some further embodiments, the immunohistochemistry on a group of cells uses an anti-endothelial membrane protein 2 EMP2 antibody or antigen binding fragment thereof; and determines the binding of the antibody or antigen binding fragment thereof to the cells, wherein an increased amount of antibody or antigen-binding fragment thereof bound to the cells relative to a control group correlates with the cells having an increased likelihood of becoming cancerous In additional embodiments, the invention provides methods of monitoring the progression of premalignancy in a subject, comprising: determining the level of epithelial membrane protein 2 (EMP2) polypeptide in cell from a tissue sample obtained at a first time; determining the level of EMP2 polypeptide in a cell from an tissue sample obtained at a second time; and comparing the levels of EMP2 polypeptide n the cell at the first and second times, wherein increased levels of EMP2 polypeptide at the second time relative to the first time correlates with progression of premalignancy to a cancerous stage. In some embodiments, the subject is undergoing drug therapy at the premalignant stage or malignant stage.

In yet other embodiments, the invention provides a method of monitoring the stage of cancer in a subject by identifying a subject presenting the cancer; determining EMP2 polypeptide level in a sample of tissue from the cancer to establish a baseline EMP2 level for the subject; measuring EMP2 polypeptide level in a tissue sample obtained from the same subject at subsequent time points; and comparing the measured EMP2 polypeptide or level with the baseline EMP2 polypeptide level, wherein an increase in measured EMP2 polypeptide in the subject versus baseline EMP2 polypeptide level is associated with a cancer which is progressing, and wherein a decrease in measured EMP2 polypeptide level versus baseline EMP2 polypeptide or polynucleotide level is associated with a cancer which is regressing or in remission.

In some embodiments, the invention provides a kit comprising: an agent which detects the level of epithelial membrane protein 2 (EMP2); a container comprising the agent for detecting the level of EMP2 in a sample; a control; and instructions to provide guidance for carrying out an assay embodied by the kit and for making a determination of the level of EMP2 based upon that assay. In preferred embodiments, the agent is a diabody. In further embodiments of the above, the kit also contains EMP2 protein as a positive control. In some preferred embodiments of any of the above, the antibody used is a diabody (e.g., KS49, KS83, KS41, KS89) as disclosed herein.

In some embodiments, treatment of a cancer which expresses or overexpresses EMP21 generally involve the repeated administration of the EMP2 antibodies, immunoconjugates, inhibitors, and siRNA preparations via an acceptable route of administration such as intravenous injection (IV), at an effective dose. Dosages will depend upon various factors generally appreciated by those of skill in the art, including without limitation the type of cancer and the severity, grade, or stage of the cancer, the binding affinity and half life of the agents used, the degree of EMP2 expression in the target tissues of the patient, the extent of circulating shed EMP2 antigen, the desired steady-state antibody concentration level, frequency of treatment, and the influence of chemotherapeutic agents used in combination with the treatment method of the invention. Daily doses may range from about 0.1 to 100 mg/kg. Doses in the range of 10-500 mg of the mAb or immunoconjugates per week may be effective and well tolerated, although even higher weekly doses may be appropriate and/or well tolerated. The principal determining factor in defining the appropriate dose is the amount of a particular agent necessary to be therapeutically effective in a particular context. Repeated administrations may be required in order to achieve tumor inhibition or regression. Initial loading doses may be higher. The initial loading dose may be administered as an infusion. Periodic maintenance doses may be administered similarly, provided the initial dose is well tolerated.

The invention further provides vaccines formulated to contain EMP2 protein or fragment thereof, particularly, a fragment as recognized by a diabody disclosed herein. The use of a tumor antigen in a vaccine for generating humoral and cell-mediated immunity for use in anti-cancer therapy is well known in the art and, for example, has been employed in prostate cancer using human PSMA and rodent PAP immunogens (Hodge et al., 1995, Int. J. Cancer 63: 231-237; Fong et al., 1997, J. Immunol. 159: 3113-3117).

The invention further provides methods for inhibiting the biological activity of EMP2. The methods comprises contacting an amount of the EMP2 with an antibody or immunoconjugate of the invention under conditions that permit an EMP2-antibody complex to form thereby, respectively, blocking EMP2 activity.

In some embodiments, the invention provides a method of treating cancer, particularly a cancer which overexpresses EMP2 or of inhibiting the growth of a cancer cell overexpressing a EMP2 protein by treating a subject or contacting the cancer cell with an antibody or fragment thereof that recognizes and binds the EMP2 protein in an amount effective to inhibit the growth of the cancer cell. In some embodiments, the cancer cell is an endometrial cancer cell. The contacting antibody can be a monoclonal antibody and/or a chimeric antibody. In some embodiments, the chimeric antibody comprises a human immunoglobulin constant region. In some embodiments, the antibody is a human antibody or comprises a human immunoglobulin constant region. In further embodiments, the antibody fragment comprises an Fab, $F(ab)_2$, or Fv. In other embodiments, the fragment comprises a recombinant protein having an antigen-binding region.

In another embodiment, the invention provides methods for treating cancer, particularly, a cancer overexpressing EMP2 or selectively inhibiting a cell expressing or overexpressing a EMP2 by contacting any one or a combination of the immunoconjugates of the invention with the cell in an amount sufficient to inhibit the cell. Such amounts include an amount to kill the cell or an amount sufficient to inhibit cell growth or proliferation. As discussed supra the dose and dosage regimen will depend on the nature of the disease or disorder to be treated, its population, the site to which the antibodies are to be directed, the characteristics of the particular immunotoxin, and the patient. For example, the amount of immunoconjugate can be in the range of 0.1 to 200 mg/kg of patient weight. The immunoconjugate can comprise the anti-EMP2 antibody or the fragment linked to a therapeutic agent. The therapeutic agent can be cytotoxic agent. The cytotoxic agent can be selected from a group consisting of ricin, ricin A-chain, doxorubicin, daunorubicin, taxol, ethiduim bromide, mitomycin, etoposide, tenoposide, vincristine, vinblastine, colchicine, dihydroxy anthracin dione, actinomycin D, diphteria toxin, *Pseudomonas* exotoxin (PE) A, PE40, abrin, arbrin A chain, modeccin A chain, alpha-sarcin, gelonin mitogellin, retstrictocin, phenomycin, enomycin, curicin, crotin, calicheamicin, sapaonaria officinalis inhibitor, maytansinoids, and glucocorticoidricin. The therapeutic agent can be a radioactive isotope. The therapeutic isotope can be selected from the group consisting of $^{212}Bi$, $^{131}I$, $^{111}In$, $^{90}Y$ and $^{186}Re$.

In any of the embodiments above, a chemotherapeutic drug and/or radiation therapy can be administered further. In some embodiments, the patient also receives hormone antagonist therapy. The contacting of the patient with the antibody or antibody fragment, can be by administering the antibody to the patient intravenously, intraperitoneally, intramuscularly, intratumorally, or intradermally.

In some embodiments, the immunoconjugate has a cytotoxic agent which is a small molecule. Toxins such as maytansin, maytansinoids, saporin, gelonin, ricin or calicheamicin and analogs or derivatives thereof are also suitable. Other cytotoxic agents that can be conjugated to the anti-EMP2 antibodies include BCNU, streptozoicin, vincristine and 5-fluorouracil. Enzymatically active toxins and fragments thereof can also be used. The radio-effector moieties may be incorporated in the conjugate in known ways (e.g., bifunctional linkers, fusion proteins). The antibodies of the present invention may also be conjugated to an effector moiety which is an enzyme which converts a prodrug to an active chemotherapeutic agent. See, WO 88/07378; U.S. Pat. No. 4,975,278; and U.S. Pat. No. 6,949,245. The antibody or immunoconjugate may optionally be linked to nonprotein polymers (e.g., polyethylene glycol, polypropylene glycol, polyoxyalkylenes, or copolymers of polyethylene glycol and polypropylene glycol).

Conjugates of the antibody and cytotoxic agent may be made using methods well known in the art (see, U.S. Pat. No. 6,949,245). For instance, the conjugates may be made using a variety of bifunctional protein coupling agents such as N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, dimethyl linker or disulfide-containing linker (Chari et al. Cancer Research 52: 127-131 (1992)) may be used.

Methods of Administration and Formulation

The anti-EMP2 antibodies or immunoconjugates are administered to a human patient in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred. The administration may be local or systemic.

The compositions for administration will commonly comprise an agent as described herein (dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

Thus, a typical pharmaceutical composition for intravenous administration will vary according to the agent. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that antibodies when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

Pharmaceutical formulations, particularly, of the antibodies and immunoconjugates and inhibitors for use with the present invention can be prepared by mixing an antibody having the desired degree of purity with optional pharmaceutically acceptable carriers, excipients or stabilizers. Such formulations can be lyophilized formulations or aqueous solutions. Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid) preservatives low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e.g. Zn-protein complexes); and/or non-ionic surfactants. The antibody can be formulated at a concentration of between 0.5-200 mg/ml, or between 10-50 mg/ml.

The formulation may also provide additional active compounds, including, chemotherapeutic agents, cytotoxic agents, cytokines, growth inhibitory agent, and anti-hormonal agent. The active ingredients may also prepared as sustained-release preparations (e.g., semi-permeable matrices of solid hydrophobic polymers (e.g., polyesters, hydrogels (for example, poly(2-hydroxyethyl-methacrylate), or poly(vinylalcohol)), polylactides. The antibodies and immunocongugates may also be entrapped in microcapsules prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles and nanocapsules) or in macroemulsions.

The compositions can be administered for therapeutic or prophylactic treatments. In therapeutic applications, compositions are administered to a patient suffering from a disease (e.g., cancer) in a "therapeutically effective dose." Amounts effective for this use will depend upon the severity of the disease and the general state of the patient's health. Single or multiple administrations of the compositions may be administered depending on the dosage and frequency as required and tolerated by the patient. A "patient" or "subject" for the purposes of the present invention includes both humans and other animals, particularly mammals. Thus the methods are applicable to both human therapy and veterinary applications.

In the preferred embodiment the patient is a mammal, preferably a primate, and in the most preferred embodiment the patient is human. Other known cancer therapies can be used in combination with the methods of the invention. For example, the compositions for use according to the invention may also be used to target or sensitize a cell to other cancer therapeutic agents such as 5FU, vinblastine, actinomycin D, cisplatin, methotrexate, and the like.

In other embodiments, the methods of the invention with other cancer therapies (e.g, radical prostatectomy), radiation therapy (external beam or brachytherapy), hormone therapy or chemotherapy. Radical prostatectomy involves removal of the entire prostate gland plus some surrounding tissue. This treatment is used commonly when the cancer is thought not to have spread beyond the tissue. Radiation therapy is commonly used to treat prostate cancer that is still confined to the prostate gland, or has spread to nearby tissue. If the disease is more advanced, radiation may be used to reduce the size of the tumor. Hormone therapy is often used for patients whose prostate cancer has spread beyond the prostate or has recurred. The objective of hormone therapy is to lower levels of the male hormones, androgens and thereby cause the prostate cancer to shrink or grow more slowly.

The combined administrations contemplates coadministration, using separate formulations or a single pharmaceutical formulation, and consecutive administration in either order, wherein preferably there is a time period while both (or all) active agents simultaneously exert their biological activities.

Molecules and compounds identified that indirectly or directly modulate the expression and/or function of a EMP2 can be useful in treating cancers that, respectively, overexpress EMP2. These modulators can be administered alone or co-administered in combination with conventional chemotherapy, radiotherapy or immunotherapy as well as currently developed therapeutics.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

Preferred pharmaceutical preparations deliver one or more active EMP2 modulators, optionally in combination with one or more chemotherapeutic agents or immunotherapeutic agents, in a sustained release formulation. Typically, the EMP2 modulator is administered therapeutically as a sensitizing agent that increases the susceptibility of tumor cells to other cytotoxic cancer therapies, including chemotherapy, radiation therapy, immunotherapy and hormonal therapy.

In therapeutic use for the treatment of cancer, the EMP2 modulators or inhibitors utilized in the pharmaceutical method of the invention are administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of cancer diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular vector, or transduced cell type in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

EXAMPLES

The following examples are offered to illustrate, but not to limit the claimed invention.

Example 1

Methods for Studying Chlamydial Infectivity and EMP2 Chlamydial Inhibitors

A. Endometrial Cell Lines and *Chlamydia* Strains.

The human endometrial adenocarcinoma cell line HEC1A (HTB112, ATCC, Manassas, Va.) was cultured in McCoy 5a media (Invitrogen, Carlsbad, Calif.) supplemented with 10% fetal calf serum (Hyclone, Logan, Utah) at 37° C. in a humidified 5% $CO_2$ and passaged every 7 days. EMP2-modulated HEC1A sublines were stable transfectants with expression plasmids for GFP, a human EMP2-GFP fusion protein, or a human EMP2-specific ribozyme (HEC1A-GFP, HEC1A-hEMP2, and HEC1A-hRV2). EMP2 protein expression levels relative to HEC1A-GFP were 1.0, 8.7, and 0.2, respectively.

An 8-strain mix of human *C. trachomatis* (serovars D, E, F, and K) and *C. muridarum* were purified, aliquoted, and stored at −80° C. until ready for use (see, Caldwell, H. D., et al., Infect Immun 31, 1161-76 (1981). All *Chlamydia* samples were made in Eagle MEM (Invitrogen) with 10% fetal calf serum (Atlanta Biologicals, GA), 3 mg/ml glucose (Fisher Scientific, PA), 1.25 µg/ml Fungizone (Invitrogen), 100 µg/ml Vancomycin (Invitrogen), 100 µg/ml gentamicin (Invitrogen), and 0.5 µg/ml cycloheximide (Sigma, St. Louis, Mo.) and kept on ice until use.

B. Antibodies and Peptides.

Antibodies to human EMP2 were produced by immunization of rabbits with SEQ ID NO.: 2 EDIHDKNAK-FYPVTREGSYG, a peptide in the second extracellular loop of human EMP2 (see, Wang, C. X., et al., Blood 97, 3890-5 (2001)). In peptide blocking experiments, this peptide was used to assure specificity of binding whereas a control 20mer peptide from the first extracellular loop of human EMP2 was used as a negative control. Antibody from the pre-immune rabbits was used as a negative control. For immunohistochemical detection of *Chlamydia* EBs or inclusions, an anti-*Chlamydia* LPS mouse antibody (clone EV1-H1) was used as kindly provided by Dr. Harlan Caldwall (Laboratory of Intracellular Parasites, National Institutes of Health, Hamilton, Mont.). FITC- and Texas Red-conjugated goat anti-rabbit IgG was from Jackson Immunotech (West Grove, Pa.); FITC anti-mouse IgG, and horseradish peroxidase-conjugated anti-rabbit or anti-mouse IgG antibody were from Southern Biotechnology Associates, Birmingham, Ala.). Rabbit anti-human β-actin was from Sigma.

C. *Chlamydia* Infection.

HEC1A cells were plated at a concentration of $2.5 \times 10^5$ cells/ml and incubated overnight to establish mono-layers. Infection with *C. trachomatis* or *C. muridarum* at multiplicity of infection (MOI) of 0.5-3.0 was performed in media containing cycloheximide at 35° C. with 5% $CO_2$ for 24 hours. Cells were fixed in methanol and inclusion bodies were identified immunohistochemically using mouse anti-*Chlamydia* LPS and FITC anti-mouse IgG secondary antibody. Cells were counter stained with Evans Blue, mounted in glycerol, and scored using fluorescence microscopy. For the antibody study, cells were incubated with antibody for 1 hour at 37° C. before the infection step. For peptide blocking, antibody was mixed with peptide at indicated concentrations for 1 hour at room temperature prior to addition to cell cultures.

D. *Chlamydia* Attachment.

HEC1A cells were plated at $1 \times 10^4$ cells/ml and incubated overnight. Cells were infected with *C. trachomatis* at MOI of 50. Cells were then incubated for 1.5 hrs at 4° C. Attached *Chlamydia* elementary bodies were identified using immunohistochemistry as described above, and counted with fluorescent microscopy (magnification, 1000×). For the antibody studies, cells were treated as described above.

E. Fluorescence Microscopy.

*Chlamydia* inclusions and elementary bodies were identified with an epiillumination fluorescent microscope (Olympus, Melville, N.Y.) using FITC and Texas Red filters. *Chlamydia* inclusions were defined by round, regular shape, with a diameter of approximately ⅓ of cell size. In order to prevent biased counting, the plates were scored in a masked fashion by at least two independent observers. 5-10 random fields were selected from each well and the total number of cells with inclusions (C1) and without inclusions (C0) were counted. The rate of infection was calculated (C1/(C1+C0)× 100) from these numbers. For the attachment study, the number of elementary bodies on the cell membrane of 100 cells/slide was counted in a masked fashion. Areas with clustered cells or indistinguishable inclusions were not counted. Experiments were performed with 2-3 replicate samples, and repeated at least three times.

F. Western Immunoblots.

Cellular lysates in Laemmli buffer were treated with peptide-N-glycosidase F (PNGase; New England Biolabs, Beverly, Mass.) to remove N-linked glycans to convert the heterogeneously glycosylated protein into a single ~20 kDa species. Proteins were separated by SDS-PAGE as previously described (see, Wadehra et al., *Mol Biol Cell* 15:2073-2083 (2004), and Wang et al., *Blood* 97:3890-5 (2001)). Blots were probed with anti-EMP2 or anti-β-actin followed by incubation with a horseradish peroxidase-conjugated anti-rabbit or anti-mouse IgG antibody. Proteins were visualized by chemiluminescence (ECL; Amersham Biosciences, Piscataway, N.J.). Negative controls (secondary antibodies alone) produced no signal. Experiments were repeated at least three times.

G. Lipid Raft Fractionation.

$5 \times 10^7$ cells were harvested, washed in PBS, and then resuspended in Tris-buffered saline (50 mM Tris, pH 7.5, 20 mM EDTA, 10 µg/ml aprotinin, 10 µg/ml leupeptin, 1 mM phenylmethylsuflonyl fluoride, and 1 mM $Na_2VO_3$. Cells were lysed by sonication (see, Wadehra et al., *Mol Biol Cell* 15:2073-2083 (2004) and Moran et al., *Immunity* 9:787-96 (1988)) and then dissolved in 1% Triton X-100 or 1% Brij 58 on ice for 60 min. The sample was mixed 1:1 with 80% sucrose (40% final), followed by step overlays with 35 and 5% sucrose. The gradient was centrifuged at 46,000 rpm for 18 h with a Sorvall SW55 rotor, and fractions (400 µl) were collected from the top of the gradient. Samples were then solubilized in Laemmli buffer, treated with PNGase to remove N-glycans, and analyzed by SDS-PAGE. Cholesterol depletion was performed as described previously (see, Claas, C., et al., *J Biol Chem* 276: 7974-84 (2001)). Briefly, cells were washed in PBS to remove serum and then incubated in DMEM containing 20 mM methyl-β-cyclodextrin (Sigma) for 60 min at 37° C. In order to insure a lack of toxicity, cells were analyzed by trypan blue exclusion prior to harvesting. Samples were then treated as described above.

H. Statistical Analysis.

For the anti-EMP2 antibody and EMP2 peptide studies, groups were analyzed by two-tailed Student's paired t test, with a significance level of $p \leq 0.05$. The statistical significance of infection and attachment rate on stably transfected cells was tested using two-tailed two-sample equal variance t-test with a confidence level of $p \leq 0.05$.

Example 2

Localization of EMP2 to Lipid Rafts

To assess whether EMP2 is localized to lipid raft domains in endometrial cells (a Chlamydial host target), EMP2 was evaluated in the HEC1A human endometrial cancer cell line by lipid raft fractionation with Brij 58 and Triton X-100. In HEC1A cells, EMP2 localized to the light, detergent-resistant gradient fractions coinciding with GM1 ganglioside, a lipid raft component (FIG. 1a,b). To confirm the localization of EMP2 to lipid rafts, lysates were prepared in 1% Triton X-100 in the presence or absence of methyl-β-cyclodextrins (MβCD) that selectively deplete cholesterol from cellular membranes and causes loss of protein localization into lipid rafts. In 1% Triton X-100, EMP2 localized to both light, detergent-resistant fractions 3-4 as well as dense fractions 6-7 (FIG. 1c). When cells were incubated for 60 minutes with MβCD in serum free conditions, EMP2 expression completely shifted to soluble, dense fractions in the presence of 1% Triton X-100 (fractions 7-10). Repletion of cholesterol in MβCD-treated cells partially restored EMP2 to the lipid raft fractions. These data indicate that, in HEC1A cells, EMP2 mainly resides within lipid raft microdomains, which are thought to be the microanatomic target for Chlamydia-host cell interaction.

Example 3

Effect of Anti-EMP2 Antibody on Chlamydia Infectivity

Figure 2:
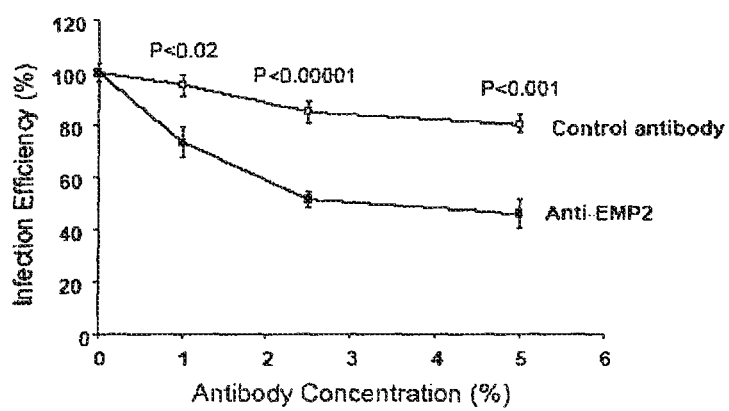
FIG. 2A-B. Illustration of anti-EMP2 antibody inhibition of Chlamydial infection. (a) Effect of anti-EMP2 antibody. HEC1A were infected with *C. trachomatis* (an 8-strain mix of human serovars D-K) in the presence of indicated concentrations of anti-EMP2 or control pre-immune antibody. Chlamydial infection efficiency (% *Chlamydia* inclusions compared to untreated cells) was determined by immunostaining (mean±SEM), and compared at each antibody concentration by student's t test. (b) Effect of EMP2 peptide on anti-EMP2 inhibition. Anti-EMP2 (5%) was pretreated with indicated concentrations of specific EMP2 (second extracellular loop) peptide or control peptide, and then coincubated with cells during *Chlamydia* infection. Infection efficiency was normalized to *Chlamydia* inclusions in cells without peptide treatment, and compared at each concentration of EMP2 or control peptide. Results are representative of 2 or more independent experiments.
Figure 2:
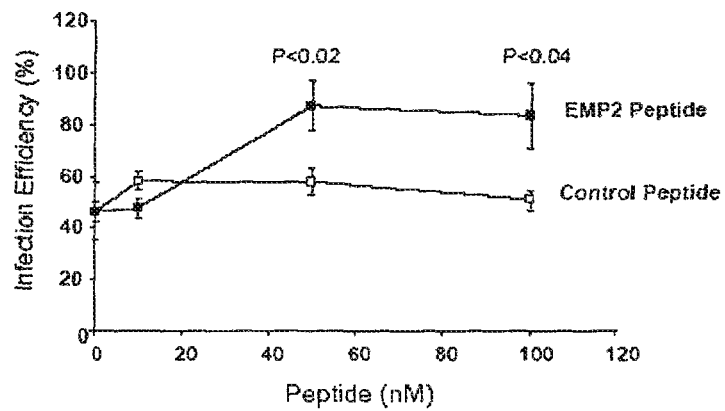

The lipid raft localization of EMP2 in endometrial cells and its control of lipid raft trafficking by integrins, caveolins, and glycosylphosphatidyl inositol-linked proteins (18, 20, 21), raised the possibility that EMP2 might directly or indirectly affect Chlamydial infectivity. To begin testing this hypothesis, anti-EMP2 antibody (specific for the 2nd extracellular loop of EMP2) was added to HEC1A cell cultures, then incubated with C. trachomatis, and infection was measured (Chlamydial inclusions, expressed as 'infection efficiency'', % inclusions relative to HEC1A cells without antibody treatment) (FIG. 2a). Anti-EMP2 antibody produced a dose-dependent inhibition of infection efficiency (reaching less than 50% of HEC1A cells without antibody), at levels that were highly significant compared to control antibody. To determine if the observed inhibition was due to EMP2 specificity, anti-EMP2 was pre-incubated with the relevant second extracellular loop EMP2 peptide, or a control peptide (first extracellular loop) (FIG. 2b). Pre-incubation of anti-EMP2 antibody with the specific EMP2 peptide neutralized the blocking effect of anti-EMP2 antibody, significantly increasing Chlamydia infection efficiency. In contrast, the control peptide at the same concentrations did not significantly increase Chlamydia infection in the presence of anti-EMP2. Thus, the anti-EMP2 effect on Chlamydia infection reflected its specificity for the second extracellular loop of EMP2.

Example 4

Efficiency of Chlamydia Infection with EMP2 Expression

Figure 3:
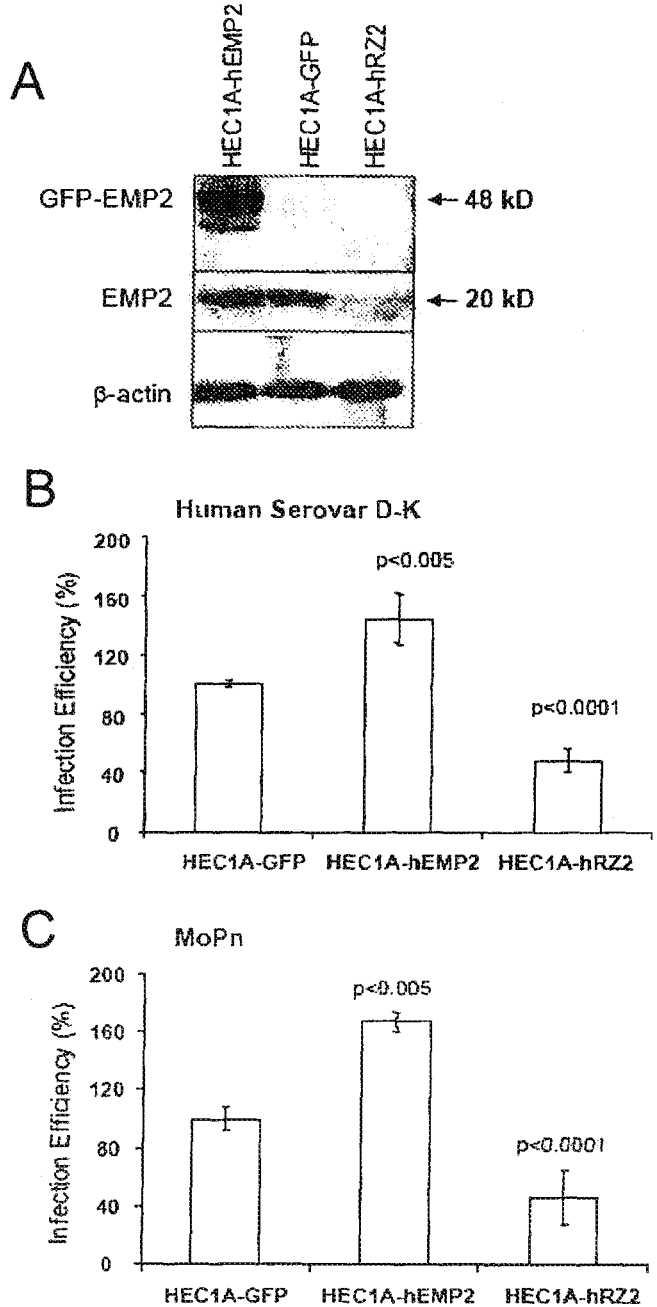
FIG. 3A-C. Illustration that EMP2 expression levels positively correlate with Chlamydial infection efficiency. (a) EMP2 levels were compared by anti-EMP2 western immunoblot in HEC1A cells stably transfected with plasmids for expression of a human EMP2-GFP fusion protein (HEC1A-hEMP2), GFP (HEC1A-GFP), or a EMP2-specific ribozyme (HEC1A-hRZ2). Shorter and longer exposures are shown for the hEMP2-GFP fusion protein (48 kDa) and native EMP2 (20 kDa), respectively. Western immunoblot for β-actin is shown as a loading control. (b, c) Cells were infected with (b) *C. trachomatis* (a mixture of 8 strains comprising serovars D-K) or (c) *C. muridarum* (MoPn), and *Chlamydia* inclusions (% HEC1A-GFP control cells) were scored (mean±SEM) and compared by student's t test to HEC1A-GFP. Data in (b) and (c) are compiled from 5 independent experiments, and each experiment had at least three replicate groups.

As another experimental test, the efficiency of Chlamydia infection in endometrial cells was examined to see if it varied with EMP2 expression. HEC1A cell lines were stably transfected with expression plasmids to overexpress an EMP2 fusion protein (HEC1A-hEMP2), suppress expression of native EMP2 via an EMP2-specific ribozyme (HEC1A-hRZ2), or a control GFP transfectant (HEC1A-GFP) (FIG. 3a). A recent quantitative study showed that EMP2 levels in these overexpressing and ribozyme HEC1A sublines were respectively 8.7-fold and 0.2-fold compared to GFP control cells (data not shown). The three HEC1A sublines were infected with C. trachomatis (FIG. 3b), and Chlamydial infection was quantitated. Compared to control HEC1A-GFP cells, EMP2-overexpressing HEC1A-hEMP2 cells had increased infection efficiency (145%, p<0.005). Reciprocally, EMP2-underexpressing HEC1A-hRV2 cells were impaired for infection efficiency (49%, p<0.0001). Similar results were obtained using a distinct Chlamydia species, C. muridarum (MoPn) (FIG. 3c). Compared to HEC1A-GFP, infection in HEC1A-hEMP2 cells was increased (167%, p<0.005), and in HEC1A-hRV2 was decreased (46%, p<0.0001).

Example 5

EMP2 Directly Mediates Chlamydia Attachment

Figure 4:
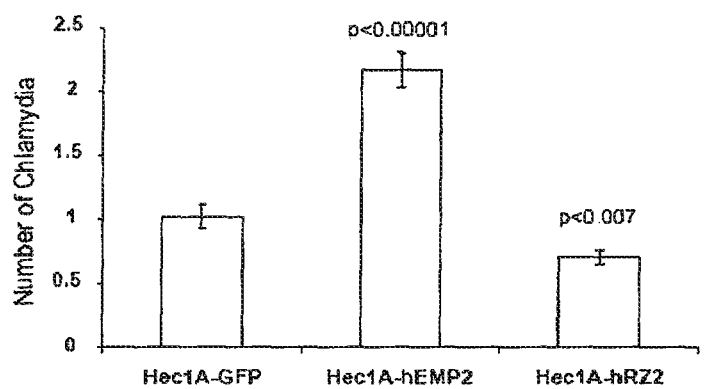
FIG. 4A-B. Illustration that EMP2 affects *Chlamydia* EB attachment. (a) HEC1A-GFP, HEC1A-hEMP2, and HEC1A-hRZ2 were incubated with *C. trachomatis* EBs for 1.5 hrs at 4° C., and the number of attached EB per cell was scored by immunofluorescence with anti-Chlamydial LPS. Values are mean±SEM. More than 800 cells scored per experimental group, and 4 independent experiments were performed. Groups were compared to HEC1A-GFP by equal variance t-test. (b) Representative immunofluorescence microscopy (magnification, 1000×) of HEC1A sublines after EB attachment, stained for EB (anti-Chlamydial LPS; Texas Red), F-actin (FITC-phalloidin), and nuclei (DAPI, blue). (c) HEC1A cells were incubated with *Chlamydia* EB alone (medium), or in the presence of anti-EMP2 or control antibody (2.5%). EB attachment was analyzed as in FIG. 4*a*; anti-EMP2 and control antibody groups were statistically compared to the medium alone group.
Figure 4:
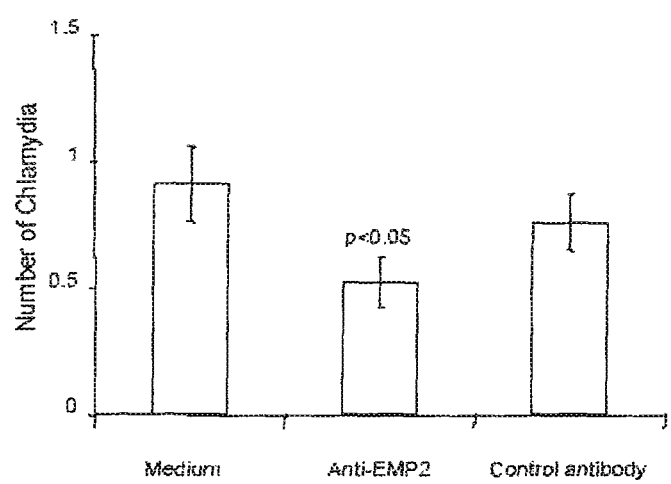

The above findings indicated that Chlamydia infection efficiency was dependent on the level of EMP2 expression, in a manner that could be blocked by anti-EMP2 antibody. While EMP2 might affect various stages of the infection process, one possible mechanism is that EMP2 acts at the initial attachment step. To test this prediction, EMP2-divergent Hec1A sublines were incubated with Chlamydia EBs in the cold, and the number of surface-attached EBs were quantitated. Compared to HEC1A-GFP, EB attachment in HEC1A-hEMP2 cells was increased (230%, p<0.0001). Reciprocally, attachment in HEC1A-hRV2 cells was decreased (70%, p<0.05). EB attachment was also inhibited by anti-EMP2 antibody. Compared to medium only, anti-EMP2 reduced EB attachment (50%, p<0.05); control antibody had no effect (FIG. 4b). These finding indicate that EMP2 directly affects EB attachment.

Example 6

Use of Phage Display Methodology to Obtain Antibodies

Phage display, first established by Smith et al in 1985, can provide an in vitro immune system useful in creating high affinity antibodies to virtually any antigens with a bare minimal recognition region. Selection of antibody using phage antibody libraries with filamentous phage and phagemids mimics humoral immune system that lack cell-mediated responses. Thus, generation of purified antibodies with affinities comparable to ones made by conventional hybridoma technology can be achieved without complications such as self-tolerance, T cell help and antigen presentation (see, Bradbury et al., *J Immunol Methods* 290:29-49 (2004); Marks et al., *Methods Mol Biol* 248:161-76 (2004); Pavlik et al., Hum Antibodies 12: 99-112 (2003); Persic et al., FEBS Lett 443:112-6 (1999); and S. Smith, Science 228:1315-7 (1985)).

For the selection of antibodies against mouse and human epithelial membrane protein-2 (mEMP2 and hEMP2 respectively), a purified phage antibody library expressing a single chain Fv(scFv) with the two V regions linked with a flexible linker is used. V genes may be derived from naturally rearranged V regions found in B-cells and scFv is expressed on pIII, a bacteriophage coat protein.

20 amino acid sequences from the extracellular loop of mEMP2 and hEMP2 such as previously used for polyclonal antibody production are chosen for antigen targets for the phage display. Successful scFv isolation against 20-mer peptide has been previously reported. In order to maintain natural conformation, these peptides are biotinylated at C- and N-termini with 4 amino acid long linkers (GSGS; SEQ ID NO.: 27). 3 rounds of selection using streptavidin and avidin-coated beads are carried out for each sample to isolate high affinity antibodies as previously described. Input and output concentrations of phage antibody libraries and values for recovery and enrichment for each round are calculated.

The specificity of selected antibodies is tested by ELISA, in which 95 colonies picked from the isolated phage populations are incubated with bound mEMP2/hEMP2 peptides on streptavidin coated plates. Most of colonies may show a 4-5 fold increase in reactivity compared to control, indicating their high specificity against antigens. C-mEMP2 samples are used for further identification of anti-mEMP2 antibodies.

Of the highly reactive colonies, 14 colonies/sample are chosen for DNA fingerprinting and subsequent DNA sequence analysis. Protein expression and purification systems are developed for each antibody using H is containing expression vectors, and testing the specificity and affinity of these antibodies is tested via Flow cytometry and Western Blot. Once validity of these antibodies is confirmed, these scFvs are fused to intact Fc region containing $C_H1$, $C_H2$ and/or $C_H3$ domains to produce intact chimeric antibody (see FIG. 5). Useful laboratory methods for performing the above are further disclosed in Bird et al., Trends Biotechnol 9:132-7 (1991); Huston et al., Proc Natl Acad Sci USA 85:5879-83 (1988); Wang et al., Blood 97:3890-5 (2001); Griffiths et al., Embo J 12:725-34 (1993); Kenanova et al., Cancer Res 65:622-31 (2005); Slavin-Chiorini et al., Cancer Res 55:5957s-5967s (1995); and Xu et al., Cancer Res 60:4475-84 (2000).

The Fc-fused antibodies stabilize the antibodies, almost to a degree to natural antibodies but also allow one to detect the antibodies with anti-Fc secondary antibodies conjugated with detectable markers. Thus, the development of these antibodies will provide strong biochemical and therapeutic tools by producing highly purified stable anti-EMP2 antibodies with increased specificity (see, Slavin-Chiorini et al., Cancer Res 55: 5957s-5967s (1995); and Xu et al., Cancer Res 60:4475-84 (2000)).

Example 7

Use of an Anti-EMP2 Diabody to Prevent, Reduce or Treat Chlamydia Infections in the Female Genital Tract (FGT)

Figure 6:
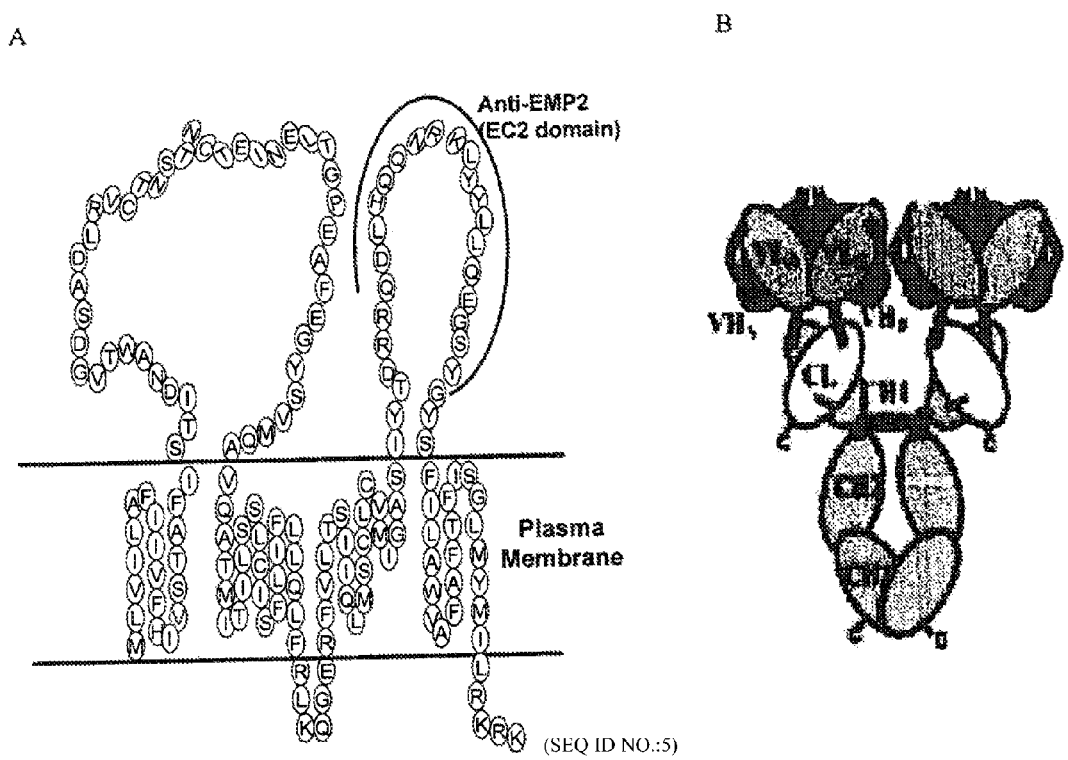
FIG. 6A-B. (A) Sequence and structure of EMP2 molecule. A 24 amino acid peptide from the small extracellular loop was used to generate the anti-EMP2 recombinant Abs. (B) Example of a single chain diabody with two V regions (40) (4).

EMP2 is a transmembrane protein in the GAS-PMP22 family with 4 transmembrane domains and two extracellular loops (FIG. 6A). EMP2 is expressed in murine and human epithelial cell lines. EMP2 is expressed within the murine reproductive tract and ovaries and mediates blastocyst implantation via αVβ3 integrin. In order to extend our in vitro studies to an in vivo model of Chlamydia genital infection, an anti-EMP2 antibody was generated that could be purified to homogeneity. Recombinant monoclonal antibodies against EMP2 were created using a 24 amino acid sequence from the small extracellular loop of murine EMP2 (FIG. 1A), the area previously used to create the polyclonal antibody used in our report (Shimazaki et al., Microbes Infect 9:1003-10 (2007)). Recombinant monoclonal antibodies have been shown to have peptide affinities comparable to ones made by conventional hybridoma technology, but can be achieved without complications such as self-tolerance, T cell help and antigen presentation (Bradbury & Marks, J Immunol Methods 290: 29-49 (2004)).

In order to select for antibodies against mouse EMP2, a purified phage antibody library expressing a single chain Fv(scFv) with the two V regions linked with a flexible linker was used (gift from Dr. James D. Marks) (Bradbury & Marks, J Immunol Methods 290:29-49 (2004)). This resulted in a diabody molecule directed against mouse EMP2 (EMP2 diabody) as shown in FIG. 6B.

Figure 7:
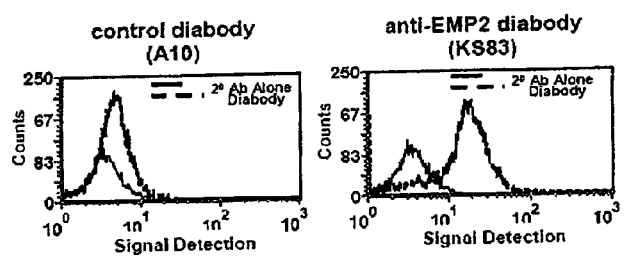
FIG. 7. Flow cytometry showing reactivity against the EMP2 expressing cells with the anti-EMP2 diabody (clone KS83) and no reactivity with a control diabody (clone A10).

Several molecularly-independent clones were observed to have high affinity for mouse EMP2 by ELISA (>5 fold) and five independent diabodies or recombinantly engineered divalent antibody fragments, were created, four with specificity against EMP2 (KS41, KS49, KS83, KS89), and a control diabody that does not recognize EMP2 (A10). The specificity of these diabodies, both reactivity against EMP2 for the KS series and no reactivity against EMP2 for the control A10 were verified by ELISA against the specific peptide used to select the antibody and by flow cytometry using cells that are known to either express EMP2 or lack EMP2 expression. FIG. 7 shows a representative flow cytometry confirmation of reactivity.

Masking EMP2 Reduces the Local Bacterial Load of Chlamydia muridarum (MoPn) In Vivo.

Figure 8:
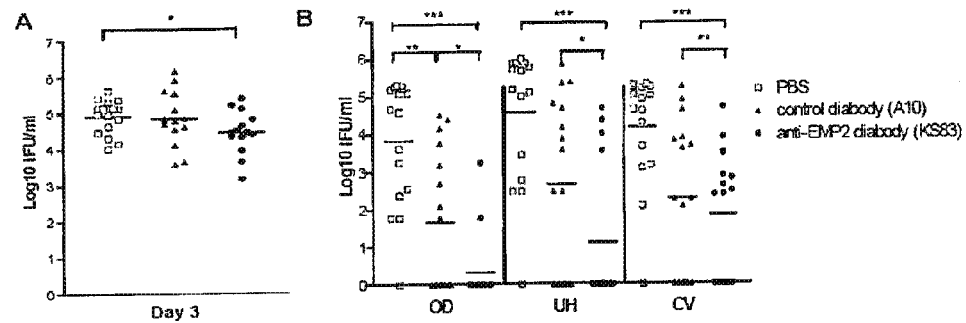
FIG. 8A-B. Mice were hormonally synchronized and vaginally pretreated with PBS, 10 μg/mouse of control or anti-EMP2 diabody (clone KS83) and mice were infected (day 0) with MoPn as described in the text. A) Swabs were collected 3 days after infection and B) regions of the FGT: OD, oviducts; UH, uterine horn and CV, cervical-vaginal, were collected the following day, homogenized, and IFUs determined. Brackets indicate statistical comparisons, *$p<0.05$, $p<0.005$, *$p<0.0001$ by two-tailed Student's t test, n=16/grp. Data are compiled from 2 experiments.

We have recently reported that preventing the ligation of EMP2 or an associated complex on a variety of host cells in vitro with MoPn significantly blocked the organism's ability to infect various cell lines (Shimazaki et al., Microbes Infect 9:1003-10 (2007)). Whether blocking EMP2 on epithelial cells in the murine FGT could affect subsequent bacterial burden in vivo was next investigated. Mice were synchronized by administering progesterone by subcutaneous injection of 2.5 mg/mouse Depo-Provera 7 days prior to infection. This treatment is necessary in mice to avoid keratinizing epithelial cells and facilitate MoPn infectivity. Groups of mice were either vaginally pretreated with an anti-EMP2 diabody, a control diabody or the vehicle alone, PBS, for 20 minutes and then infected by vaginal deposition of $1.5 \times 10^5$ infectious forming units (IFU) C. muridarum (MoPn). As can be appreciated in FIG. 8A, a single pretreatment with a small amount of anti-EMP2 diabody significantly reduced initial infection levels in the FGT as determined from vaginal swabs taken every 3rd day. Tissue was collected from 3 regions of the FGT; oviducts (OD), uterine horns (UH) and cervical-vaginal (CV) region which includes the endocervix as previously described. Examination of bacterial burden in FGT regions revealed a significant decrease in MoPn levels compared to mice pretreated with control diabody. Further, pretreatment with anti-EMP2 diabody reduced ascending infection since the majority of anti-EMP2 diabody treated mice were negative for MoPn (FIG. 8B).

Figure 9:
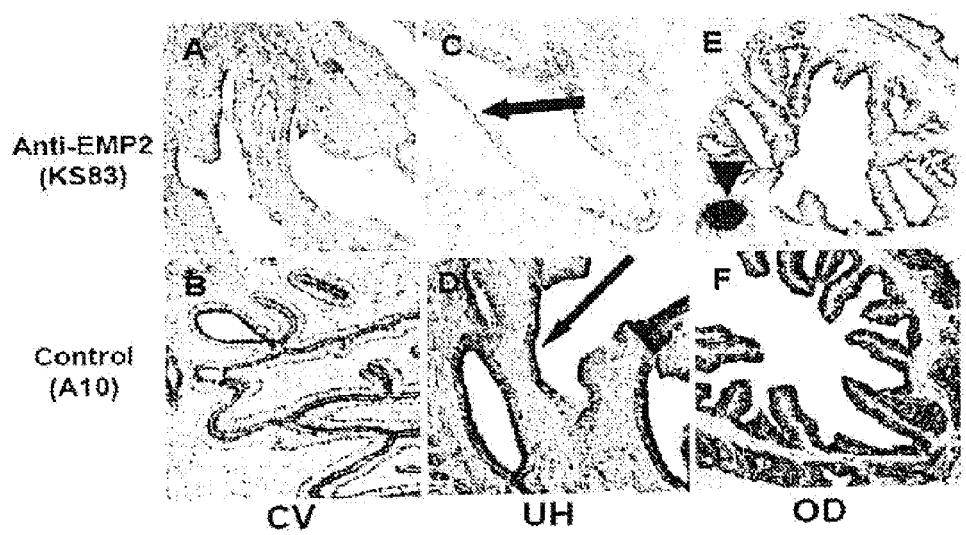
FIG. 9A-F. The GT regions from mice pretreated with anti-EMP2 diabody KS83 (A, C & E) or control A10 (B, D & F) were harvested after 24 hours and IHC staining was performed on formalin-fixed, paraffin-embedded sections with a 1:500 dilution of anti-EMP2 immune sera. Arrow: EMP2 expression in epithelial cells & arrowhead: EMP2 staining of ova, inset.
Figure 10:
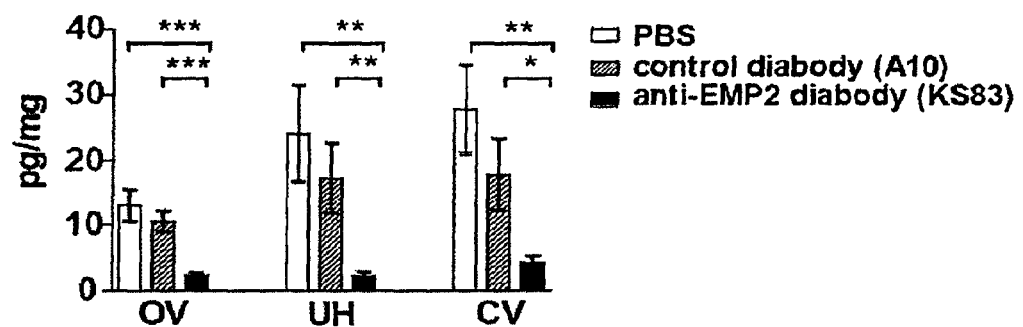
FIG. 10. FGT tissues from pretreated mice were collected 4 days after infection, homogenized and the supernatant collected following filtration through 0.22 μm filters and stored at −80° C. pending the ELISA assay. Protein ELISA for IFNγ was performed using a commercial kit (eBioscience). IFNγ protein levels were determined and expressed as pg per milligram of tissue collected. Data are expressed as the mean+SD of picograms IFNγ per mg of protein. Brackets indicate statistical significance, *$p<0.05$, Student's t-test, n=16/grp.
Figure 11:
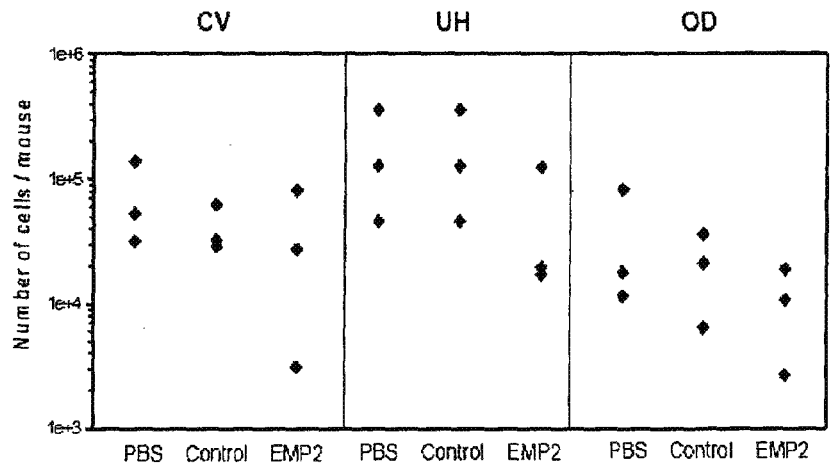
FIG. 11. Mice were pretreated with diabodies or vehicle and infected GT were collected 4 days later, treated with collagenase and stained with CD4, CD3, Ly6G and CD45. Each data point is a pool of 10 mice showing the numbers of or Ly6G+CD4-CD3-neutrophils.
Figure 12:
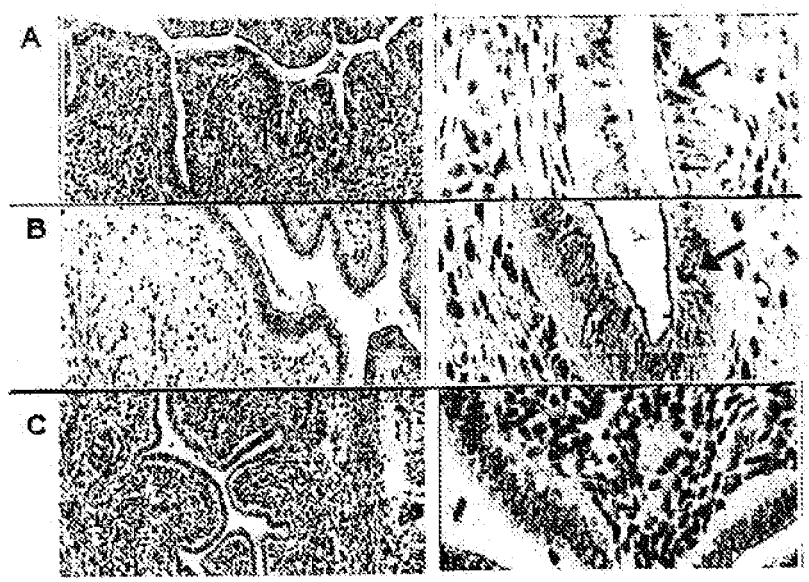
FIG. 12A-C. Formalin-fixed, paraffin-embedded sections of UH were obtained from ovarectomized CF-1 mice 3 days after receiving progesterone (A) estradiol (B), or no hormonal treatment (C) and IHC stained with anti-murine EMP2 sera. Magnification left (100×) and right (400×).
Figure 13:
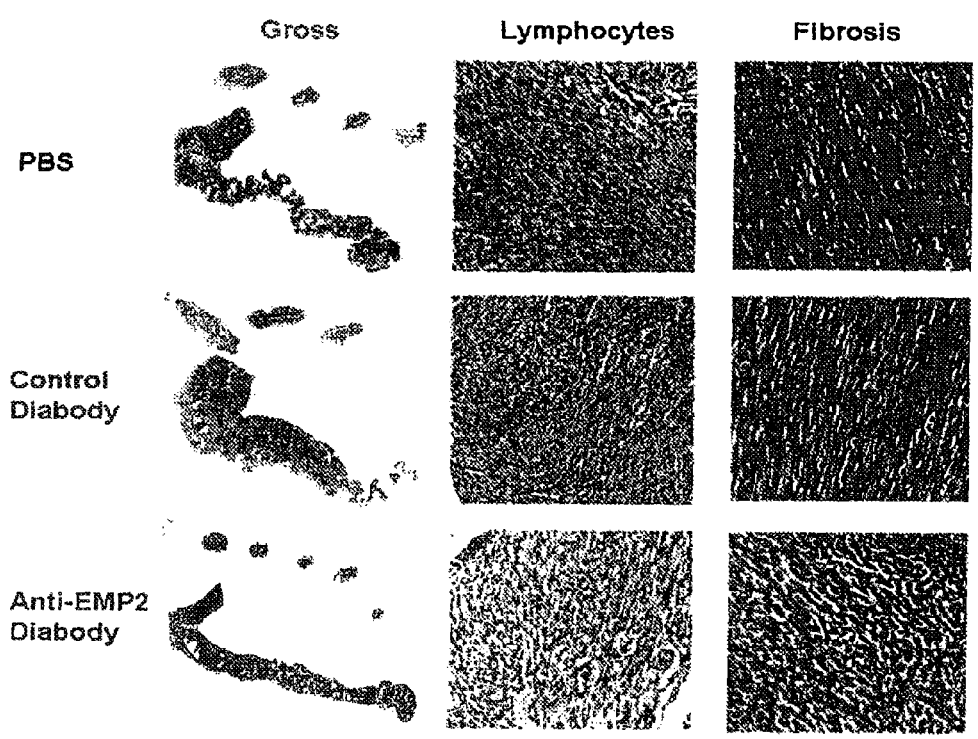
FIG. 13. Effects of no antibody (PBS), control diabody, and test antibody in the tissue indicated. Five-week old BALB/c mice were intravaginally pre-treated for 30 min with PBS, control diabody (A10), or anti-EMP2 diabody (KS49), prior to the infection with *C. muridarum* (MoPn). Left, gross pathology at day 14; Middle, histopathology with hematoxylin and eosin at day 3 (200× magnification). Note recruitment of lymphocyte aggregates (arrows) and fibrosis (arrowheads). Right, histopathology (200× magnification) with trichrome stain, where blue indicates collagen deposition related to fibrosis.
Figure 14:
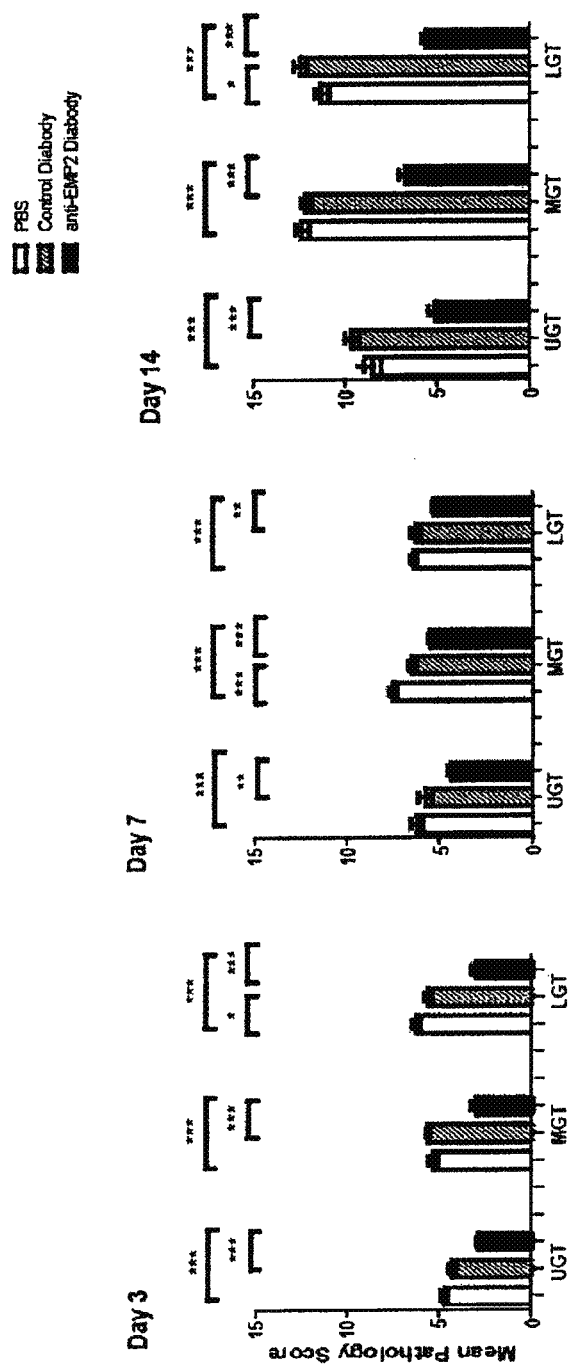
FIG. 14. Effects of no antibody (PBS), control diabody, and test antibody in the tissues indicated. Five-week old BALB/c mice were intravaginally pre-treated for 30 min with PBS, control diabody (A10), or anti-EMP2 diabody (KS49), prior to the infection with *C. muridarum* (MoPn). Genital tracts were obtained at day 3, 7, and 14 after infection, and divided into oviduct (UGT), uterine horn (MGT), and cervico-vaginal (LGT) segments. Histologic sections from each segment were quantitatively scored from 10-20 mice; mean±SEM are shown. Student's t test comparisons are shown (*, $p<0.05$; ***, $p<0.001$).

EMP2 is expressed on epithelial cells of the murine FGT in vivo (Shimazaki et al., Microbes Infect 9:1003-10 (2007); Wadehra et al., Dev Biol 287:336-45 (2005)) and ligation with anti-EMP2 diabody may reduce infectivity by modulating EMP2 expression. To determine whether pretreatment with anti-EMP2 modulates expression within the FGT, immunohistochemical staining (IHC) staining was next performed. As shown in FIG. 9, mice vaginally pretreated with anti-EMP2 diabody showed reduced and altered expression of EMP2 using IHC detection of EMP2 within formalin-fixed, paraffin-embedded sections of FGT compared to control diabody treated mice. Vaginal pretreatment with anti-EMP2 diabody (KS83) reduced the overall expression of EMP2 on epithelial cells as compared to epithelial cells from control diabody pretreated mice (FIG. 9). The diabody was able to reach the oviducts (OD) as EMP2 pretreatment also reduced expression on epithelial cells, however the ova which are adjacent to oviduct tissue serve as a positive internal control as they intensely express EMP2 (FIG. 9E inset, arrowhead) even in anti-EMP2 diabody pretreated mice. Interestingly, anti-EMP2 treatment reduced expression on the apical surface of epithelial cells (FIGS. 9C & D, arrows).

Immune Parameters are Reduced by Blocking the Interaction of EMP2 with MoPn.

Pretreatment with anti-EMP2 diabody was also able to reduce activation of the local immune response reflecting a reduction in vaginal infection. The cytokine IFNγ is secreted by CD4, CD8 and NK cells which appear in GT tissue shortly after infection (Maxion et al., *Infect Immun* 72:6330-40 (2004); Darville et al., *Infect Immun* 69:3556-61 (2001)). Expression of IFNγ by ELISA was examined using a commercially available kit (eBioscience) in homogenized regions of the GT obtained 4 days after pretreatment and infection as described above. As shown in FIG. 10, analysis revealed a significant decrease in IFNγ protein levels in the CV and UH regions, markedly diminished levels within the OD and suggesting that cells secreting IFNγ were reduced in number in mice pretreated with EMP2 diabody.

Fewer leukocytes ought to be present in the FGT of mice pretreated with an anti-EMP2 diabody to reflect the reduction in bacterial burden and decrease in local IFNγ protein levels. Accordingly, the number of polymorphonuclear (PMN) cells in pretreated mice early after infection was evaluated. Briefly, mice were pretreated with anti-EMP2, diabody control or vehicle and infected as above. Early after infection (4 days), FGT tissues were collected and stained for cell surface markers of immune cells. As shown in FIG. 11, diminished numbers of PMN (Ly6G/C+CD3−CD4−) were observed, particularly in the OD of the FGT. This observation confirms the ability of anti-EMP2 diabody treatment to reduce MoPn tissue burden and IFNγ levels in vivo which results in diminished numbers of accumulating leukocytes. Taken together, the results show that pretreatment of mice with anti-EMP2 diabodies significantly reduces the ascending bacterial burden and inflammatory response in the FGT following infection with *C. muridarum*. Accordingly, masking EMP2 in individuals should reduce *C. trachomatis* genital infection and pelvic inflammatory disease and sexual transmission.

Our laboratory recently found that progesterone treatment results in increased EMP2 surface expression (data not shown) and pretreatment of mice with progesterone is understood to increase the susceptibility to infection in vivo. The effect on surface expression of EMP2 of progesterone therapy in vivo was next tested.

Ovariectomized female mice were treated with daily injections of 100 ng per mouse of 17β estradiol or 1 mg per mouse of progesterone dissolved in 100 μL of sesame oil, or sesame oil alone (Sigma). Mice were euthanized at various time points and genital tracts were processed for IHC using mEMP2 antisera or control rabbit serum. Tissue blocks were immunostained using an antigen retrieval technique according to published protocol, and rabbit polyclonal antibodies generated against mouse EMP2 were previously described (Wang et al., *Blood* 97:3890-3895 (2001)). In ovariectomized mice EMP2 is not detected by immunohistochemistry, however treatment with progesterone or estradiol, induces expression of EMP2 on the endoplasmic reticulum and golgi of the luminal and glandular epithelium at 3 days (FIG. 12). Expression is observed on the apical plasma membrane at an earlier time point (not shown). Taken together, these data support a novel approach, GT tissue pretreatment with anti-EMP2 to reduce MoPn genital infection.

Example 8

Effect of Treatment with Anti-EMP2 Diabodies on Endometrial Adenocarcinoma Cells In this study, recombinant human anti-EMP2 diabodies were developed using filamentous bacteriophage library methodology, and assessed the efficacy of these diabodies in growth, apoptosis, and xenograft tumor formation by EC cell lines. Diabody avidity and specificity for EMP2 peptide and native protein were confirmed by ELISA and flow cytometry using multiple cell lines. Biologically, treatment of various human endometrial adenocarcinoma cell lines with these anti-EMP2 diabodies resulted in a significant increase in caspase-dependent apoptotic cell death in vitro, and reduced tumor volume and viability in vivo. The results indicate that EMP2 is a targetable molecule for pharmacological induction of apoptosis in EC cell lines.

It is notable that a human immunoglobulin gene library permitted successful production of anti-human EMP2 antibodies. While these antibodies in effect detected a self-antigen, they should not be construed as a native autoimmune specificity, since the combinatorial library permits the creation of VH/VL pairings that may not have been represented in the native clonal populations (Marks et al., *Methods Mol Biol* 248:161-76 (2004)). Conversely, the direct yield of human immunoglobulin reagents with such biologic activity avoids the complexity of reengineering non-human epitopes while retaining antigen specificity and avidity in rodent-derived reagents (Wu et al., *NatBiotechnol* 23:1137-46 (2005)).

Successful therapeutic targeting of antibodies depends on tissue penetration and uptake, rapid blood clearance, and serum stability. Small antibody fragments such as scFv have rapid tissue penetration and fast clearance from the circulation, but as monovalent reagents are limited by low binding affinity and avidity (Adams et al., *Cancer Res* 53:4026-34 (1993); Colcher et al., *Q J Nucl Med* 42:225-41 (1998); Milenic et al., *Cancer Res* 51:6363-71 (1991); Yokota et al., *Cancer Res* 52:3402-8 (1992)). Accordingly, we engineered selected anti-EMP2 scFv fragments into bivalent diabodies, which are known to have an increased avidity and stability, by shortening the linker region of scFv's between heavy chain variable region ($V_H$) and light chain variable region ($V_L$) (Holliger et al., *Nat Biotechnol,* 23:1126-36 (2005); Nielsen et al., *Cancer Res* 60:6434-40 (2000)), SDS-PAGE and size exclusion FPLC data confirmed successful diabody formation with >95% purity, and >20-fold increase in binding activity compared to original scFvs.

FACS analysis of anti-hEMP2 and anti-mEMP2 diabodies demonstrated similar binding activity to native surface EMP2. This was specific for EMP2, since it was dependent on levels of native or engineered EMP2 expression. Interestingly, whereas anti-hEMP2 and anti-mEMP2 diabodies were species specific for isolated peptides by ELISA, they showed cross-species reactivity for cell surface human and mouse EMP2. It should be noted that the selecting hEMP2 and mEMP2 peptide antigens shared 90% sequence similarity and 50% sequence identity. Thus, the key contact residues for this set of anti-EMP2 diabody clones may target the species-conserved homologous peptides. Why might this crossreactivity be detected with the native protein, but not the isolated peptide. First, typical for tetraspan proteins, we predict that native EMP2 exists as a multimer on the membrane. This would increase the avidity of diabody binding compared to isolated peptide in ELISA format. Second, in the native protein, the EC2 domain (containing the target peptide) exists as a constrained loop, which due to sequence homology is likely to adopt a similar conformational display. In contrast, free peptide in the ELISA format will represent a set of random peptide conformations. It is thus conceivable that the homologous loop conformation of the hEMP2 and mEMP2 would result in closer binding affinity of the different species for each diabody. The strong cross-species homology of the EC2 peptide, and this apparent topological display suggest that this epitope may be biologically important for the native function of EMP2.

Anti-EMP2 diabody treatment exhibited significant antiproliferative effects by increasing caspase 3-related apoptosis in multiple endometrial adenocarcinoma cell lines. These effects on cell growth inhibition and apoptosis correlated with EMP2 expression levels of independent cell lines, suggesting that binding of EMP2 induced apoptosis signaling. In support of this idea, progesterone induction of EMP2 expression increased diabody-mediated cell death in RL95-2 cells. Alternatively, recent data has shown that intravaginal injection of anti-EMP2 diabody in the murine genital tract dramatically reduced EMP2 expression in native endometrial epithelium (Shimazaki et al., *Microbes Infect* 9:1003-10 (2007)). It should be noted that EMP2 exists in a physical complex with FAK and certain integrin isoforms and promotes FAK-Src activation (Morales et al., *FAK-Src Regulated PVR Response is EMP2 Dependent*, Submitted 2008). Since divergent signaling pathways are induced by integrin ligation, it is conceivable that apoptosis may be favored in the absence of FAK (Mould et al., *CurrOpinCell Biol* 16:544-51 (2004); Renshaw et al., *J Cell Biol* 147:611-8 (1999); Zhao et al., *J Cell Biol* 143:1997-2008 (1998)).

In order to determine the preclinical applicability of targeting EMP2, toxicity experiments were initially performed. It is known that the highest levels of EMP2 occur in the lung, skin, and female reproductive tract (Wang et al., *Blood* 97:3890-5 (2001); Ben et al., *Genomics*, 49:443-7 (1998)). Importantly, anti-EMP2 diabody treatment exhibited minimal toxicity as measured by weight loss, liver function, and changes in histology when administered systemically over a two week time frame. Furthermore, the reduction in tumor volume for both HEC-1A/V and HEC-1A/OE cells with anti-EMP2 diabodies suggest that targeting EMP2 may be a successful for treatment. Interestingly, HEC-1A/V cells which express modest levels of EMP2 on the plasma membrane in culture, in vivo expressed levels of EMP2 comparable to HEC-1A/OE generated tumors. Consequently, HEC-1A/V cells responded significantly to anti-EMP2 diabody treatment.

Apoptosis can involve activation of diverse caspase isoforms, depending on the death receptor-mediated and mitochondrial pathways of apoptosis induction (Rupinder et al., *Vascul Pharmacol*, 46:383-93 (2007)). In this study, caspase 3 activation was assessed, since it is the downstream event of all of these pathways (Rupinder et al., *Vascul Pharmacol*, 46:383-93 (2007)). We note that EMP2 is important for integrin expression and function, and also modifies surface display of GEMs and their associated membrane proteins (see Introduction). Accordingly, EMP2 may modulate integrin-dependent signaling associated with survival signaling, or by other GEM-associated receptors. For example, K-ras and HER-2/neu has been identified as an EC-associated oncogene that stably interacts with the plasma membrane and regulates activation of selective signaling pathways via lateral diffusion and interaction with other molecules (Enomoto et al., *Diagn Mol Pathol* 3:292-7 (1994); Enomoto et al., *Cancer Res*, 53:1883-8 (1993); Niv et al., *J Cell Biol* 157:865-72 (2002)). Thus, several lines of investigation might be pursued to determine mechanism by which anti-EMP2 diabodies elicit apoptosis.

The above results were achieved employing the following methods:

A. Cell Lines.

The human endometrial adenocarcinoma cell line HEC-1A (HTB112, ATCC, Manassas, Va.), RL95-2 (CRL 1671, ATCC), Ishikawa (gift of Dr. Mark Pegram, UCLA), and mouse embryonic fibroblast cell line NIH 3T3 (CRL-1658, ATCC) were cultured in appropriate media supplemented with 10% fetal calf serum at 37° C. in a humidified 5% $CO_2$ and passaged every 7 days. In addition to HEC-1A wild type cells (HEC-1A/WT), HEC-1A sublines were prepared to increase or decrease EMP2 expression using expression plasmids for a human EMP2-GFP fusion protein and control GFP (Wadehra et al., *DevBiol* 287:336-45 (2005)). These sublines were termed HEC-1A/OE, HEC-1A/V, respectively. EMP2 expression levels in each cell line were determined by Western blot analysis.

B. Phage Library Selection.

Phage library selection was carried out as previously described (Blazek et al., *J Virol Methods* 115:83-92 (2004)). Briefly, $10^{12}$-$10^{13}$ phage from the $8.2\times10^8$ member phagemid library were first pre-depleted with 100 μL of streptavidin magnetic beads (Invitrogen, Carlsbad, Calif.) in 2% milk PBS for 1 hour at room temperature. The pre-depleted phage library was then mixed with 10 μg of biotin conjugated 24 amino acid peptides corresponding to the extracellular loop of human and mouse EMP2 (SEQ ID NO.: 28 SEQ ID NO.: 42 DIHDKNAKFYPVTREGSYGGSGSK and SEQ ID NO.: 29 DLHQQNRKLYYLLQEGSYGGSGSK respectively) (Wang et al., *Blood* 97:3890-5 (2001)) for 1 hour at room temperature. 100 uL of 2% milk PBS pre-blocked streptavidin magnetic beads were added to the phage mixture and rotated for 15 min at room temperature. Beads were washed extensively with 0.1% PBS/Tween, 2% milk PBS, and finally with PBS, and bound phage was eluted out with 1 mL of 100 mM triethylamine, neutralized with 500 ul of 1M Tris-HCl pH 7.4, and added to 10 mL of exponentially growing *E. coli* TG1. Culture was then plated on 150 mm culture plates with 2× TY 100 μg/ml ampicillin, 2% glucose agar plates (2× TY/amp/glu) overnight at 37° C. The next day, colonies were scraped from the plates and used to amplify the phage for the second round of selection described above. A total of three selections were performed before screening and characterization of the selected phage antibodies.

C. Diabody Construction and Production.

Binding specificity of expressed single chain Fv (ScFv) was analyzed by Enzyme-Linked ImmunoSorbent Assay (ELISA) as previously described (Marks et al., *Methods Mol Biol* 248:161-76 (2004)) (see ELISA section below for details). Single chain Fv clones with high reactivity were selected for the construction of diabodies. A number of different ScFv clones were characterized and confirmed by DNA fingerprinting (Gussow et al., *Nucleic Acids Res* 17:4000 (1989); Marks et al., *J Mol Biol* 222:581-97 (1991)) and DNA sequencing (Schier et al., *J Mol Biol* 255:28-43 (1996)). pHEN phagemids from selected phage were isolated using QIAprep Spin Miniprep Kit (Qiagen, Valencia, Calif.). Single chain Fv inserts were then digested and cloned into pSYN I vector in frame with a c-Myc and 6 His (SEQ ID NO.: 30) tag at the C-terminus. In order to convert ScFv fragments into diabody, 15 amino acid linker region (AGTGGTGGAG-GCGGTTCAGGCGGAGGTGGCTCTGGCG-GTGGCGGATCG; SEQ ID NO.: 31) of the ScFv was shortened into 5 amino acid linker (AGTGGTGGAGGATCG; SEQ ID NO.: 32) using QuikChange site-directed mutagenesis kit (Stratagene, La Jolla, Calif.) (Adams et al., *Br J Cancer* 77:1405-12 (1998)). Deletion mutation was confirmed by DNA sequencing analysis.

Expression and purification of the selected diabodies were carried out using a modified protocol described by Marks et al. (Marks et al., *Methods Mol Biol* 248:161-76 (2004)). Single colonies were picked from the plate, inoculated into 1 L/colony of 2×TY with 100 µg/mL ampicillin (2×TY/amp) at 250 rpm at 37° C. When $A_{600}$ reached 0.8-1.0, protein expression was induced by addition of 1 mM IPTG. The culture was shaken at 120 rpm at 30° C. for 4 hours and spun at 7000 rpm for 15 min at 4° C. Pellets were then re-suspended in 20 mL of periplasmic buffer (200 mM Tris-HCl, 20% sucrose, 1 mM EDTA, pH 7.5), and 290,000 units of lysozyme (Epicentre, Madison, Wis.) was added to each mixture. The mixtures were incubated at room temperature for 5 min and spun at 7000 rpm for 15 min at 4° C. The pellets were then re-suspended with 20 ml of 40 mM $MgSO_4$ and left on the ice for 10 min. The samples were spun again, and the supernatants from this spin were combined with the first supernatants. The mixture was then filtered with 0.45 µm filters, and dialyzed in dialysis buffer (300 mM NaCl, 20 mM HEPES, pH 8.0) overnight at 4° C. Next morning, the samples were filtered again with 0.2 µm filters and run through 5 mL of the Ni-NTA column (Qiagen). The column was washed with 20 mL wash buffer (300 mM NaCl, 20 mM imidazole, 20 mM HEPES, 0.05% Tween, pH 8.0), and bound diabodies were eluted with 5 ml elution buffer (300 mM NaCl, 250 mM imidazole, 20 mM HEPES, pH 8.0), dialyzed in endotoxin free PBS overnight at room temperature. Samples were filtered with 0.22 µm filters, and stored at −20° C. until their use. Purity of the preparation was determined by size exclusion chromatography profile (FPLC; Superdex 75, Amersham Pharmacia Biotech, Uppsala, Sweden) as necessary.

For preparative analysis of the diabody, purified diabody preparations were run on 4-20% Tris-Glycine gel (Invitrogen) and bands were visualized using GelCode Blue Stain Reagent (Pierce, Rockford, Ill.). Gels were scanned and the band intensities were analyzed using the Image J program (National Institute of Health, Bethesda, Md.).

D. Enzyme-Linked Immunosorbent Assay (ELISA).

10 µg/mL of biotinylated 24 amino acid peptide (see the phage library selection section above) was coated onto streptavidin-coated 96-well plates (Roche Applied Science, Indianapolis, Ind.) in PBS for 1 hour at room temperature. Plates were then washed with PBS and blocked with 2% milk PBS for 2 hours at 37° C. Expressed phage antibodies or diabodies were added to each well, incubated at room temperature for 1 hour, and washed with 0.05% PBS/Tween three times. Bound antibodies or diabodies were detected with mouse anti-c-Myc (9E10) antibody (Calbiochem, San Diego, Calif.), followed by horseradish peroxidase (HRP) conjugated anti-mouse antibody (BD Bioscience Pharmingen, Franklin Lakes, N.J.) and TMB solution (eBioscience, San Diego, Calif.). Plates were read by microplate reader Model 550 (Bio-Rad, Hercules, Calif.) at 450 nm.

E. Fluorescent Activated Cell Sorting (FACS) Analysis.

Cells were detached from a flask with 2 mM EDTA, spun at 1000 rpm for 3 min, and re-suspended with BD Cytofix/Cytoperm solution (BD Bioscience Pharmingen) to final concentration of $1 \times 10^7$ cells/mL. Cells were washed with BD Perm/Wash buffer (BD Bioscience Pharmingen), followed by a 30 min incubation with BD Perm/Wash buffer containing 2% BSA on ice. After spinning at 2000 rpm, cells were resuspended with BD Perm/Wash buffer containing 1 µg of purified monoclonal diabody in 96 well plates on ice for 1 hour. Cells were then washed with 200 µL of BD Perm/Wash buffer three times. Bound monoclonal diabodies were detected with mouse anti-c-Myc (9E10) antibody (Calbiochem), followed by R-PE conjugated anti-mouse secondary antibody (BD Bioscience Pharmingen).

G. Serum Stability Assay.

Diabody preparations were diluted in 200 µL of human or mouse serum to a final concentration of 5 µg/mL and plated in a 96 well plate. The plate was incubated at 37° C. for 15 min, 24 hours, 48 hours, or 72 hours. Samples were collected, and the diabody serum stability was determined via ELISA method described above.

H. Cellular Cytostasis.

$5 \times 10^4$ cells were incubated in 96 well plates with 0-25 µg/mL diabody. At 0 and 24 hours, cells were stained with toluidine blue, and then lysed in 2% SDS (Biowhittaker, Walkersville, Md.). The number of cells at each timepoint was quantitated in triplicate by the absorbance at 595 nm, and the standard error of the mean was calculated. Each experiment was repeated at least three times.

I. Cell Death Analysis.

For cell death analysis, cells ($5 \times 10^5$) were incubated in 6-well plates in 10% FCS medium. Cells were incubated with 12.5 µg/ml diabody A10 (control), KS49, or KS83 for 72 hrs. For hormone treatment, RL95-2 cells at 60-70% confluence were washed in PBS, and subsequently incubated with progesterone (Sigma., St. Louis, Mo.) in treatment medium (DMEM/Ham's F-12 supplemented with 0.5% charcoal-stripped FBS (Omega Scientific, Tarzana, Calif.), 1% penicillin-streptomycin, and 1% L-glutamine). Progesterone was and added to treatment medium at 25 µM as previous described (Wadehra et al., *Reprod Biol Endocrinol* 6:15 (2008)). Cell viability was determined by trypan blue exclusion.

To determine the rate of apoptosis, cells were stained with annexin V (Becton Dickinson Biosciences, Torrey Pines, Calif.) and 7-aminoactinomycin D (7AAD) or propidium iodide. Cells were harvested at 24-48 hours after diabody treatment as indicated in the figure legends. The cells were incubated for 15 minutes on ice with annexin V-Cy3 and 7AAD as per manufacturer's instructions, and analyzed on a flow cytometer (Becton Dickinson Biosciences).

J. Caspase 3 Activity.

Cells were incubated as above and harvested 48 hours after diabody treatment. Samples were normalized based on cell number and lysed by boiling for 5 minutes in Laemmli buffer (62.5 mM Tris-Cl, pH 6.8, 10% glycerol, 2% SDS, 0.01% bromophenol blue, 2% βME). The lysate was separated on a 12% SDS-polyacrylamide gel and transferred to a nitrocellulose membrane (Amersham Pharmacia). Membranes were incubated with 10% milk in PBS containing 0.1% Tween-20. An anti-caspase 3 mouse monoclonal antibody, 2 ng/µL final concentration (BD Biosciences), or anti-fl-actin (Sigma) was added and incubated for 1 hour. The membrane was washed 3 times with PBS/Tween-20 and then incubated for 45 minutes with a horseradish peroxidase-labeled secondary antibody (goat anti-mouse immunoglobulin G [IgG] or goat anti-rabbit IgG, 1:2000 dilution; Jackson ImmunoResearch Laboratories, West Grove, Pa.). Proteins were detected by chemiluminescence (Amersham Pharmacia).

K. Native Tissue Toxicity.

Six to eight week old female wildtype (C57BL/6) mice were obtained from JAX Laboratories. Animals were inoculated intravenously with increasing concentrations (0.5-5 mg/kg) of A10 diabody control, anti-EMP2 diabodies (K83, K49), or a vehicle control (sterile PBS). Three mice were utilized per group and were injected twice a week. After 14 days, serum was collected, and mice were euthanized by cervical dislocalization. Tissue (kidney, liver, spleen, lung, skin) were collected and fixed in formalin. Samples were processed by the Tissue Procurement Laboratory at UCLA. Toxicity in tissue was assessed using hemotoxylin and eosin and validated by a pathologist. Serum alanine aminotransferase (ALT) and direct and total bilirubin were assessed by the UCLA Medical Center Clinical Laboratories.

L. Tumor Xenografts and Treatment.

Four to six-week-old nude BALB/c female mice were obtained from Charles River Laboratories (Wilmington, Mass.) and maintained at the University of California, Los Angeles in accordance with IRB procedures. Animals were inoculated s.c. with $1\times10^6$ HEC-1A/V and HEC-1A/OE cells into the right and left shoulder flanks. Once tumors reached 2-3 mm (largest diameter, day 13), tumors were injected biweekly with 1 mg/kg anti-EMP2 diabody 83, control diabody 10, or a vehicle control (sterile saline) for up to three weeks. Six mice were utilized per group. Tumors were measured every 3-4 days using vernier calipers, and tumor volumes were calculated by the formula $\pi/6\times$ larger diameter$\times$ smaller diameter (Agus et al., Cancer Res 59:4761-4 (1999)). At day 30, tumors were excised and fixed in formalin. Tumors were processed for hemotoxylin and eosin staining by the Tissue Procurement Laboratory at UCLA. In addition, some sections were stained for EMP2 expression as outlined below.

M. Immunohistochemistry.

The expression of EMP2 in paraffin fixed tissue has been previously described (Wadehra et al., Cancer 107:90-8 (2006)). Briefly, sections were processed for antigen retrieval by incubating slides at 95° C. for 20 minutes in 0.1 M citrate, pH 6.0. Sections were stained using primary hEMP2 antiserum (1:400) or the corresponding preimmune control at the same dilution overnight at 4 C. The antibody signal was detected according to the manufacturer's instructions using the Vectastain ABC kit (Vector Labs, Burlingame, Calif.). EMP2 expression was visualized using diaminobenzidine. Nuclei were counterstained using hemotoxylin.

N. Statistical Analysis.

For the ELISA analysis, groups were analyzed by two-tailed Student's paired t-test at a 95% confidence level. Differences in the in vitro anti-proliferative and in vivo effects of diabodies were evaluated using Student's unpaired t-test at a 95% confidence level (GraphPad Prism version 3.0; GraphPad Software, San Diego, Calif.).

The following experimental results were obtained:

A. Construction and Expression of Anti-EMP2 Diabodies.

Anti-EMP2 scFv was isolated using phage library expressing $8.2\times10^8$ variable scFv as previously described (Blazek et al., J Virol Methods 115:83-92 (2004)). EMP2 specific scFv were selected using 24 amino acid-long peptides that represent second extracellular domain (ECD) of human (hEMP2) and mouse EMP2 (mEMP2). Fourteen clones were identified by hEMP2 ELISA, and of these, three independent clones were found to be independent by sequence features. Three independent clones were constructed and produced as diabodies; all were positive by ELISA, and one (KS49) was positive by flow cytometry for native EMP2 binding (see below). Fourteen clones were identified by mEMP2 ELISA, and of these, three independent clones were found to be independent by sequence features. Three independent clones were constructed and produced as diabodies; all were positive by ELISA, and one (KS83) was positive by flow cytometry for native EMP2 binding. As negative controls, two random pre-selection scFvs were chosen (A10 and B3): none were positive by ELISA with hEMP2 or mEMP2 in either the scFv or diabody format.

For the present study, KS49 and KS83 were chosen as representative scFv for hEMP2 and mEMP2, respectively. Two random pre-selection scFv, A10 and B3, were used as negative control antibodies. In order to increase the avidity of the selected scFv, we created divalent diabodies by shortening the scFv linker region to 5 amino acids (FIG. 15A) (Adams et al., Br J Cancer 77:1405-12 (1998)). Diabodies were expressed in TG1 E. coli and purified as previously published (see Methods).

B. SDS-PAGE and Size Exclusion FPLC Analysis of Purified Anti-EMP2 Diabodies.

Analysis of purified diabody proteins by SDS-PAGE in a reducing condition showed a single band around 25 kDa, which corresponds to an appropriate size of scFv or diabody monomer (FIG. 15A) (Olafsen et al., Protein Eng Des Sel 17:21-7 (2004)). Size exclusion chromatography also demonstrated the formation of a dimer with a protein retention time at 20.23 min (average of two experiments), matching with the expected size of the diabody (FIG. 15B) (Olafsen et al., Protein Eng Des Sel 17:21-7 (2004)). Both data indicated >95% purity of the prepared diabody samples.

C. Antigen Specificity of Anti-EMP2 Diabodies.

Figure 15:
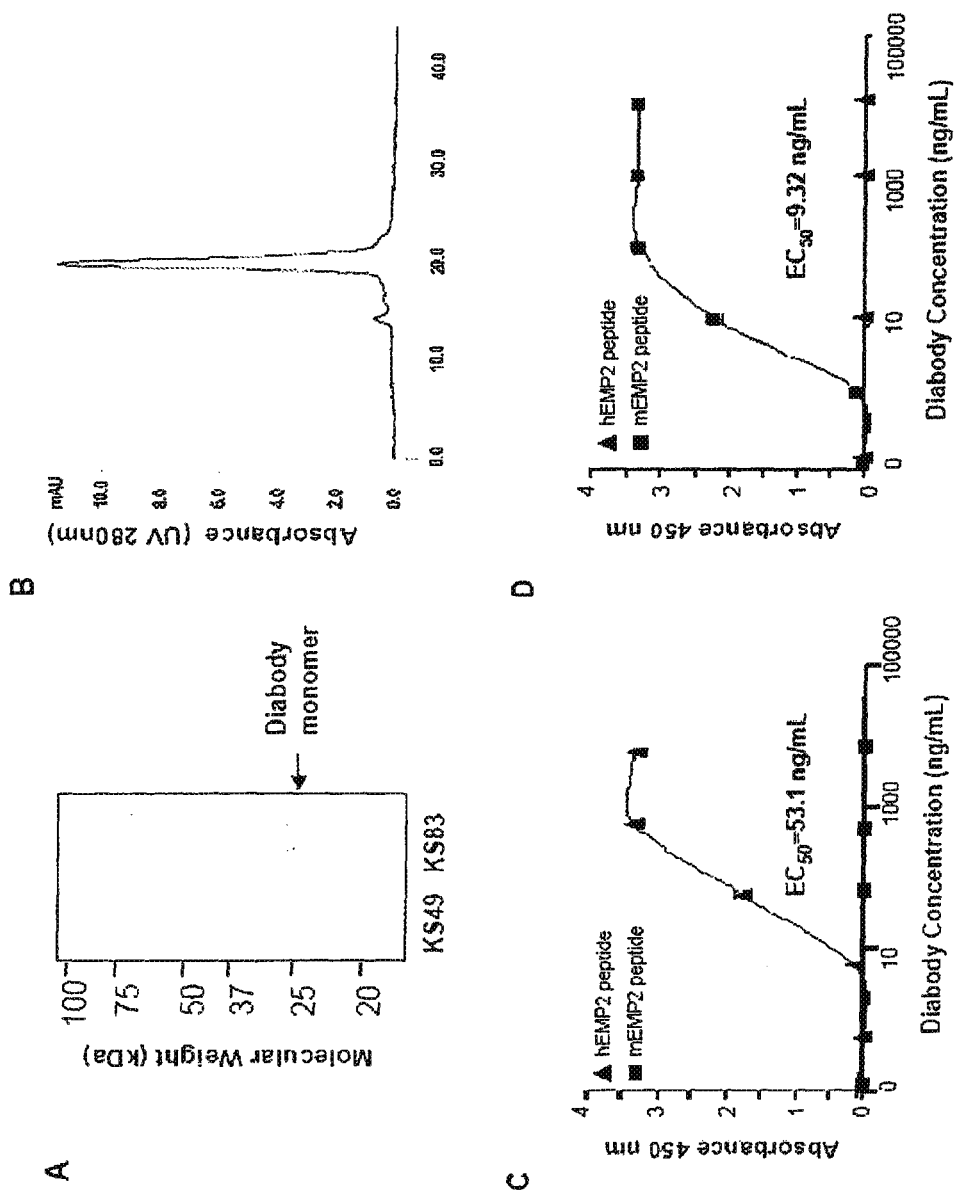
FIG. 15A-D. Biochemical characterization of constructed diabodies. (A) SDS-PAGE and Coomassie staining analysis of purified diabodies. Lane 1: KS49; Lane 2: KS83. Arrow indicates an appropriate molecular weight of diabody monomer. (B) Size-exclusion FPLC of purified diabody on a Superdex 75 column. Retention time of each sample was compared with appropriate molecular weight standards. (C) ELISA dose-response assay of KS49 diabody. Plates were coated with hEMP2 peptides, and 10-fold dilutions (1:10-1:1×10$^5$) of the diabody preparations were assayed for binding. (D) ELISA dose-response assay of KS83 diabody. Plates were coated with mEMP2 peptides, and 10-fold dilutions (1:10 to 1:1×10$^6$) of the diabody preparations were assayed for binding. For (C) and (D), EC$_{50}$ was calculated. Results are representative of 3 independent experiments.

Specificity and titer of selected diabodies were initially tested by ELISA using plates coated with hEMP2 or mEMP2 peptides. KS49, a diabody selected against hEMP2 peptide, showed significant binding to hEMP2, whereas binding to mEMP2 was below detection (data not shown). Reciprocally, KS83, a diabody selected against mEMP2 peptide, showed high reactivity to mEMP2 peptide, whereas reactivity to hEMP2 peptide was below detection (data not shown). Negative control diabodies A10 and B3 demonstrated minimal reactivity to either hEMP2 or mEMP2 peptides. As shown in FIGS. 15C and D, diabody titration analysis showed a dose-dependent binding of the KS49 and KS83 to the hEMP2 and mEMP2 antigens respectively. KS49 and KS83 efficiently bound to their appropriate antigen with $EC_{50}$ (the antibody concentration at which 50% of maximum binding occurs) of 53.1 ng/mL and 9.32 ng/mL, respectively. Using monovalent scFv products of these two antibodies, the $EC_{50}$ for cognate EMP2 peptide was >2 µg/mL (data not shown). Thus, divalency contributed to the avidity of the two anti-EMP2 diabodies.

Figure 16:
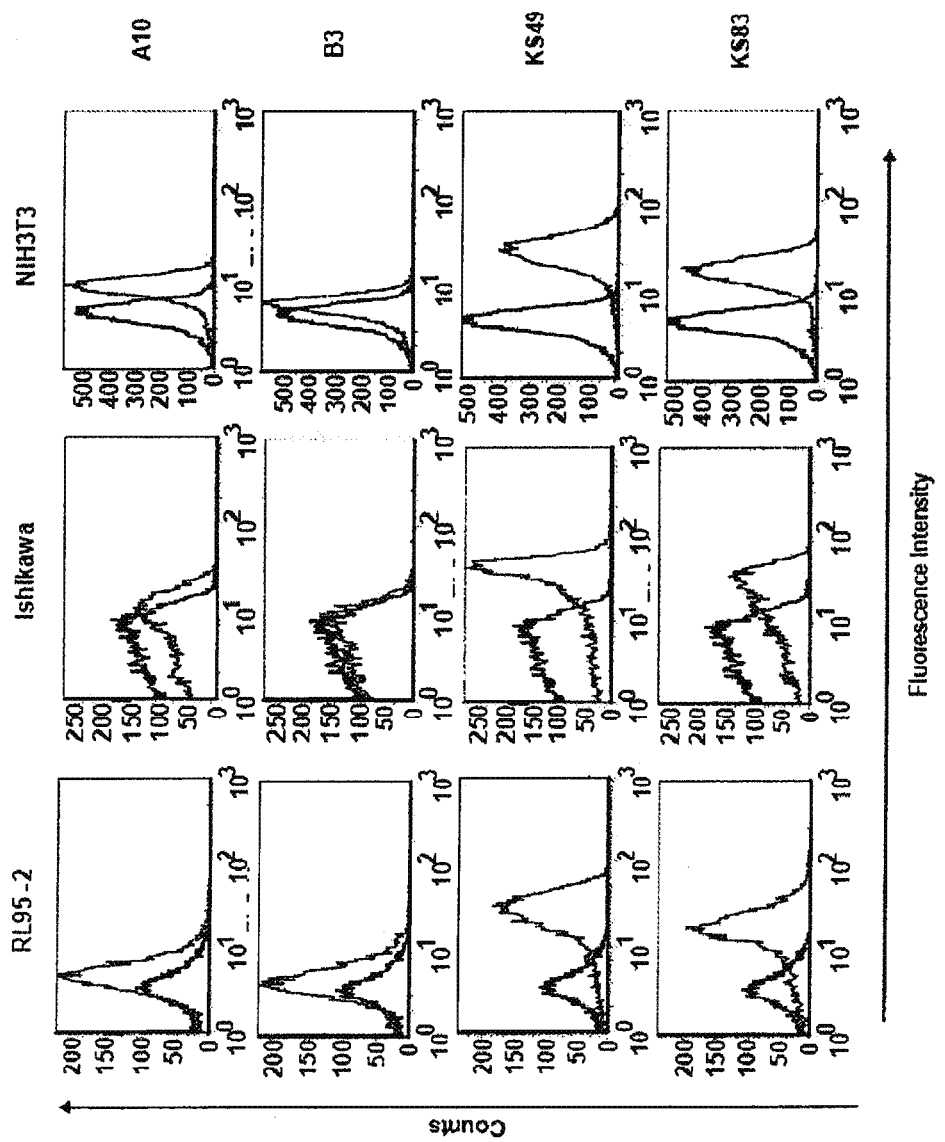
FIG. 16. Cellular binding analysis of purified diabodies using flow cytometry. Cellular binding of purified diabodies (labeled on right) was tested on RL95-2, Ishikawa, and NIH 3T3 cells using flow cytometry. Three independent experiments were performed with similar results; a representative graph is shown.

Binding activity of diabodies was further assessed by FACS analysis using human endometrial adenocarcinoma cell lines RL95-2, Ishikawa, and the murine fibroblast cell line NIH 3T3, all of which are known to express EMP2 (representative data shown in FIG. 16). Both KS49 and KS83 showed significant reactivity against all three cell lines regardless of the difference in host species. This species cross reactivity may reflect the close homology between human and mouse EMP2 second extracellular domains (50% sequence identity and 90% sequence similarity; see Methods). Control diabodies A10 and B3 showed minimal detection against all cell lines, confirming the specificity of the anti-EMP2 diabodies against EMP2 proteins.

Diabody Stability in Serum.

One of the practical usages of diabodies is therapeutic targeting of cancer tumors (Cochlovius et al., *J Immunol* 165:888-95 (2000)). In order to assess the stability of anti-EMP2 diabodies in physiological condition, 5 µg/mL of diabodies were incubated in either human or mouse serum at 37° C. for 15 min, 24, 48, and 72 hours. The retained stability was measured using an ELISA. The binding activity of the diabody was maintained over the 72 hour-period in both human and mouse serum (data not shown). The specificity, which was detected using relevant and irrelevant peptide antigens, was also retained for the prolonged incubation period.

Antibodies to EMP2 Inhibit Cellular Growth.

Figure 17:
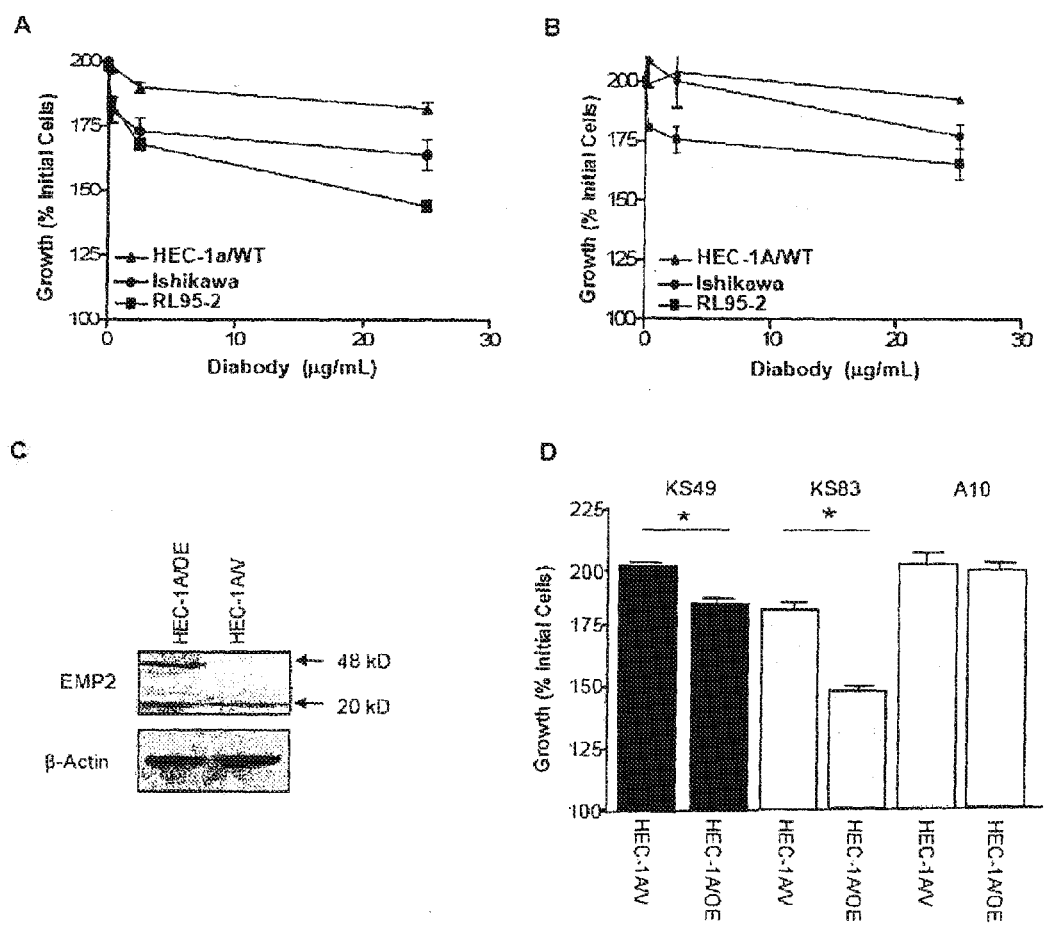
FIG. 17A-D. Diabodies induce cytostasis. 0-to-25 µg/ml of diabody KS83 (A) or KS49 (B) were added to endometrial carcinoma cell lines HEC-1A, Ishikawa, and RL95-2 in triplicate for 24 hours. Cytostasis was calculated as the ratio of final/initial cells plated using the absorbances at 595 nm. (C) Western immunoblots for EMP2 from extracts of HEC-1A/V and HEC-1A/EMP2. Western immunoblot for β-actin was used as a loading control. (D) 25 µg/ml of diabodies KS83, KS49 or the control diabody A10 were added to HEC-1A vector control cells (HEC-1A/V) or cells that overexpress EMP2 (HEC-1A/OE) in triplicate for 24 hours. Comparison by student's t test, *p<0.05.

To determine if selective targeting of EMP2 may be an effective therapy in EC, the endometrial adenocarcinoma cell lines RL95-2, Ishikawa, and HEC-1A-WT were utilized. Cells were treated with KS49, KS83, or the control diabody A10 (FIG. 17). Compared to control diabody, anti-EMP2 diabodies induced cellular cytostasis within 24 hours. When cells were incubated with a range of recombinant antibody from 0-25 µg/mL, the recombinant clones KS49 and KS83 had a dose-dependent, anti-proliferative effect on the endometrial cell lines RL95-2 and Ishikawa (FIGS. 17A and B). In contrast, diabodies against EMP2 exhibited small effects on HEC-1A-WT cells, which have been shown to bear little EMP2 on the plasma membrane (Wadehra et al., *DevBiol* 287:336-45 (2005)). Previous studies have characterized HEC-1A/OE cells which overexpress EMP2 as a GFP fusion protein (Wadehra et al., *DevBiol* 292:430-41 (2006); Wadehra et al., *DevBiol* 287:336-45 (2005)). In these cells, EMP2 protein levels are increased approximately 4 fold (FIG. 17C). Strikingly, diabodies KS83 and KS49 significantly inhibited growth of HEC-1A/OE cells by 55% and 21%, respectively, over cells treated with the control diabody A10 (FIG. 17).

F. Diabodies to EMP2 Induce Apoptosis.

Figure 18:
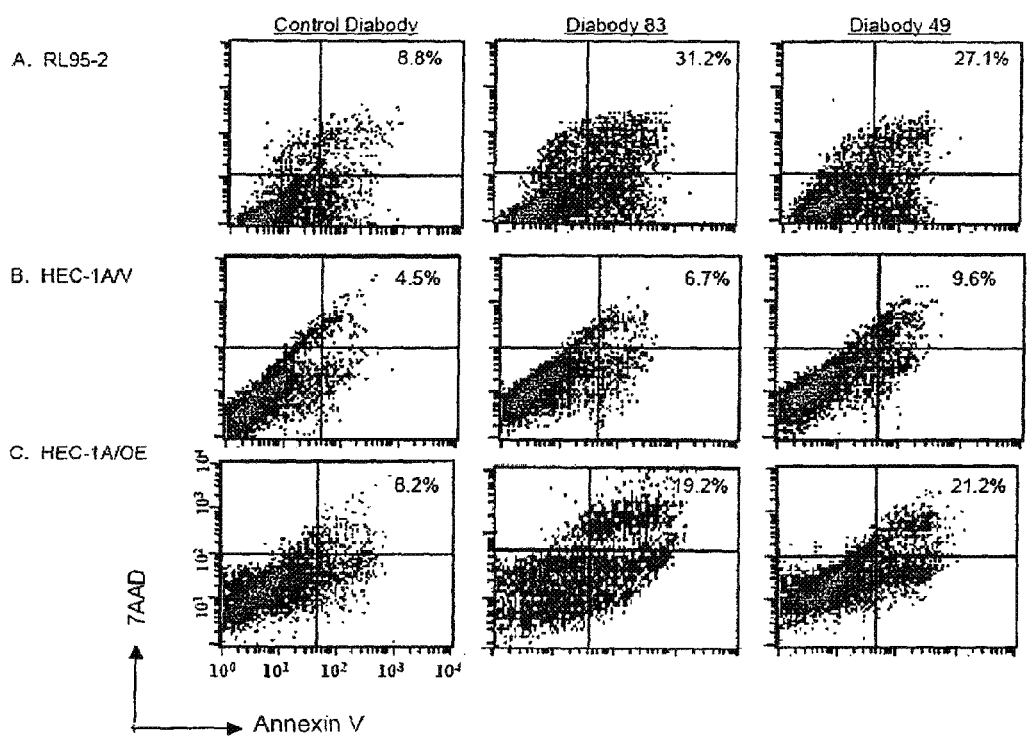
FIG. 18A-C. Diabodies promote apoptosis. (A) RL95-2, (B) HEC-1A/V, and (C) HEC-1A/OE cells were incubated with 12.5 µg/ml KS49, KS89, or A10 (control) diabody for 24 hours. Cells were washed and stained with annexin V and 7AAD. Staining is expressed as the % annexin V-7AAD positive cells above the isotype control. The experiment was repeated 3 times with similar results; a representative graph is depicted.

To correlate the decrease in cell number with an increase in cell death, cells were assessed for apoptotic cells using flow cytometry. Endometrial carcinoma cell lines were treated with 12.5 µg/mL KS49, KS83, or control A10 diabodies for 24 hours. Apoptotic cells were detected with annexin V and 7-AAD and analyzed by flow cytometry. Anti-EMP2 diabodies induced pronounced cell death in RL95-2 cells (FIG. 18A). Small effects were seen in HEC-1A-GFP cell lines, but cell death was enhanced by overexpression of EMP2 (HEC-1A/OE) (FIGS. 18B and C). Thus, anti-EMP2 diabodies specifically increased apoptosis, in a manner associated with increased EMP2 surface expression.

G. Synergistic Effects of Progesterone.

RL95-2 expresses functional PR-A and PR-B receptors, and their expression of EMP2 is regulated by progesterone (Wadehra et al., *Reprod Biol Endocrinol* 6:15 (2008)). As progesterone increases EMP2 expression, we predicted that progesterone treatment may enhance the rate of anti-EMP2 diabody mediated apoptosis in RL95-2 cells as these cells express functional progesterone receptors (Myers et al., *J Clin Endocrinol Metab*, 86:2323-6 (2001); Schneider et al., *J Soc Gynecol Investig* 5:334-8 (1998)). Cells were stained with annexin V and propidium iodide and analyzed by flow cytometry. Dramatically, the combination of progesterone (P4) and KS49 or KS83 treatment increased the number of annexin V, propidium iodide positive cells by 16.5% and 19% respectively compared to cells treated with diabody alone (FIG. 19A).

Figure 19:
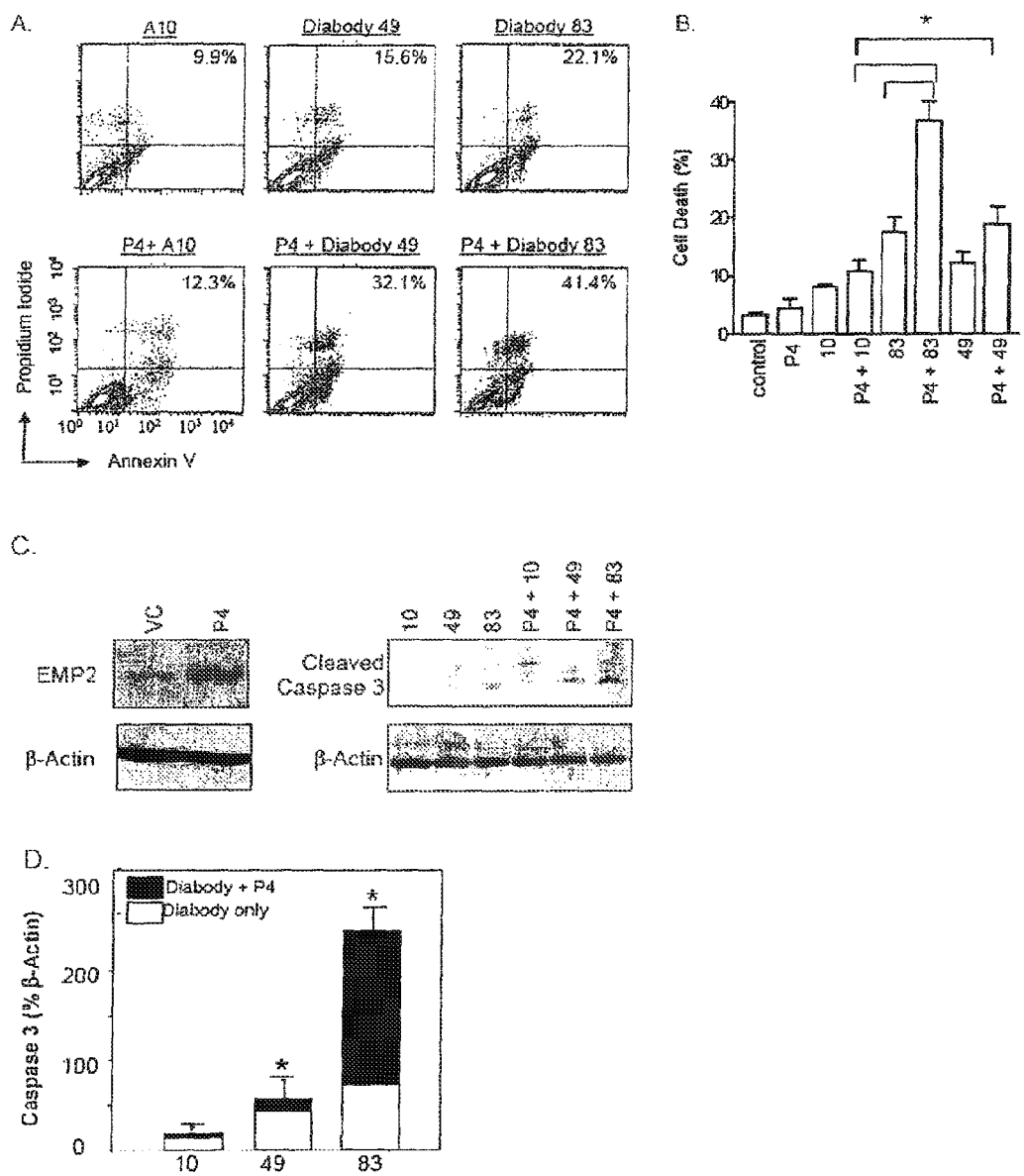
FIG. 19A-D. Progesterone augments diabody mediated apoptosis. (A) RL95-2 cells were treated with progesterone P4 (25 µM) or vehicle control (ethanol) in combination with 12.5 µg/ml KS49, KS89, or A10 (control) diabody for 24 hours. Cells were stained for annexin V and propidium iodide, and apoptosis and cell death were further quantitated using flow cytometry. Staining is expressed as the % annexin V-propidium iodide positive cells above the isotype control. (B) RL95-2 cells were treated with progesterone P4 (25 µM) or vehicle control (ethanol) and diabodies KS83, KS49, or A10 for 72 hours. Cell death was determined by trypan blue exclusion, and depicted as a % of the total number of cells counted. *p<0.05 (C) EMP2 expression, apoptosis and cell death were further quantitated using western blot analysis. Western immunoblots for EMP2 from extracts of RL95-2 cells cultured for 72 hours with 25 µM progesterone (P4) or a vehicle control (VC; ethanol). Cleaved caspase 3 (Δ caspase 3) was assessed after 24 hours of treatment. β-actin serves as the loading control. The experiment was repeated 3 times, and a representative graph is depicted. (D) Statistical analysis of cleaved caspase 3 relative to β-actin expression, compared by student's t test; *p<0.05.
Figure 20:
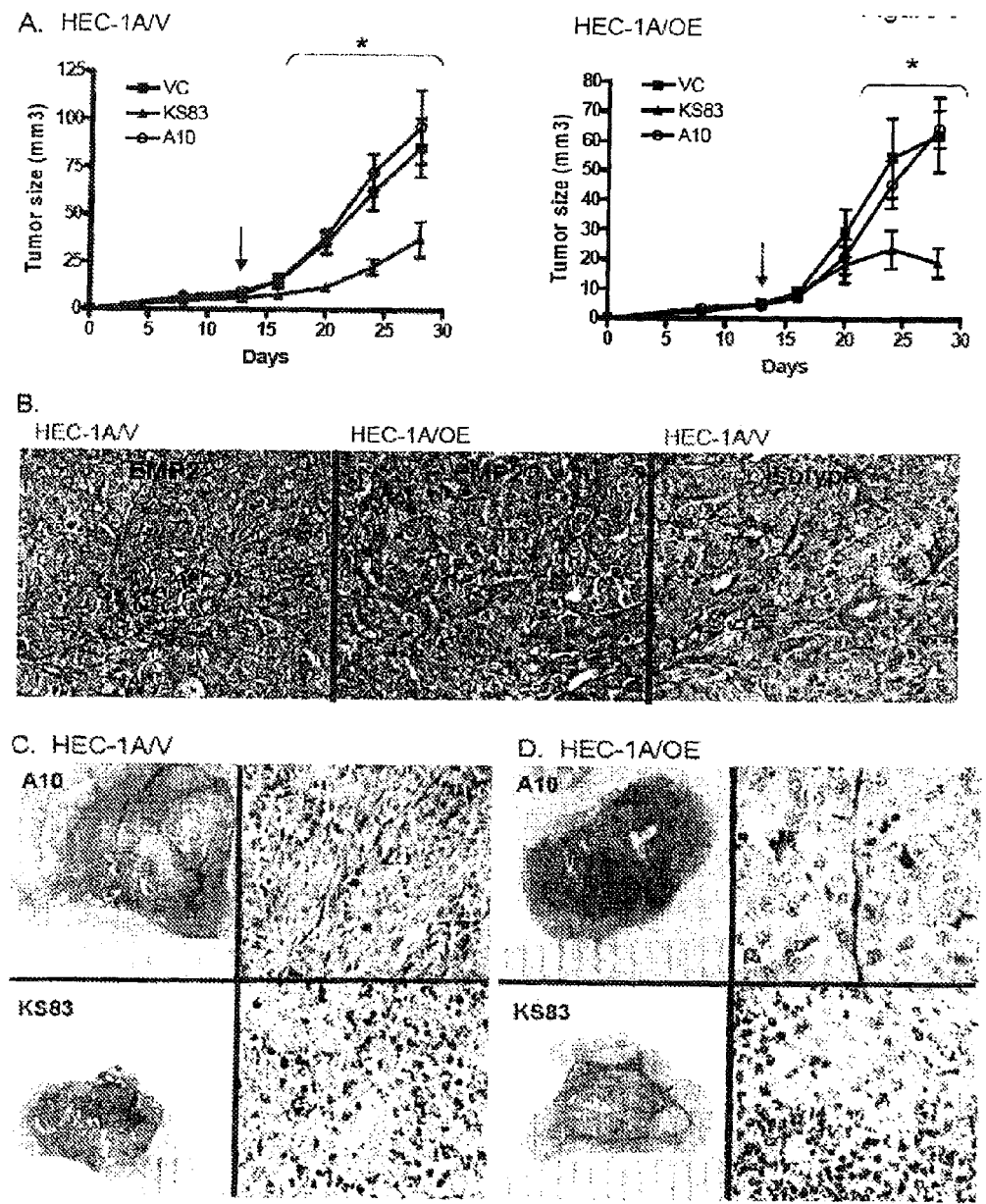
FIG. 20A-D. Anti-EMP2 diabodies reduce tumor load in vivo. (A) HEC-1A/V or HEC-1A/OE cells were injected s.c. into nude Balb/c female mice (left panel). At day 13 (arrow), mice were injected twice a week with 1 mg/kg of anti-EMP2 diabody 83, control diabody A10, or sterile saline. Tumor volume was calculated using calipers. n=6. (B) EMP2 expression was analyzed in untreated tumors using immunohistochemistry using EMP2 antisera or control antisera. Magnification: 20×. (C, D) At day 31, mice were euthanized and tumor histology was assessed by hemotoxylin and eosin staining. A representative panel depicts excised tumors (left; scalebar, m) and the corresponding histology (right; 40× magnification) for HEC-1A/V (C) and HEC-1A/OE (D). Comparison by student's t test, *p<0.05.
Figure 21:
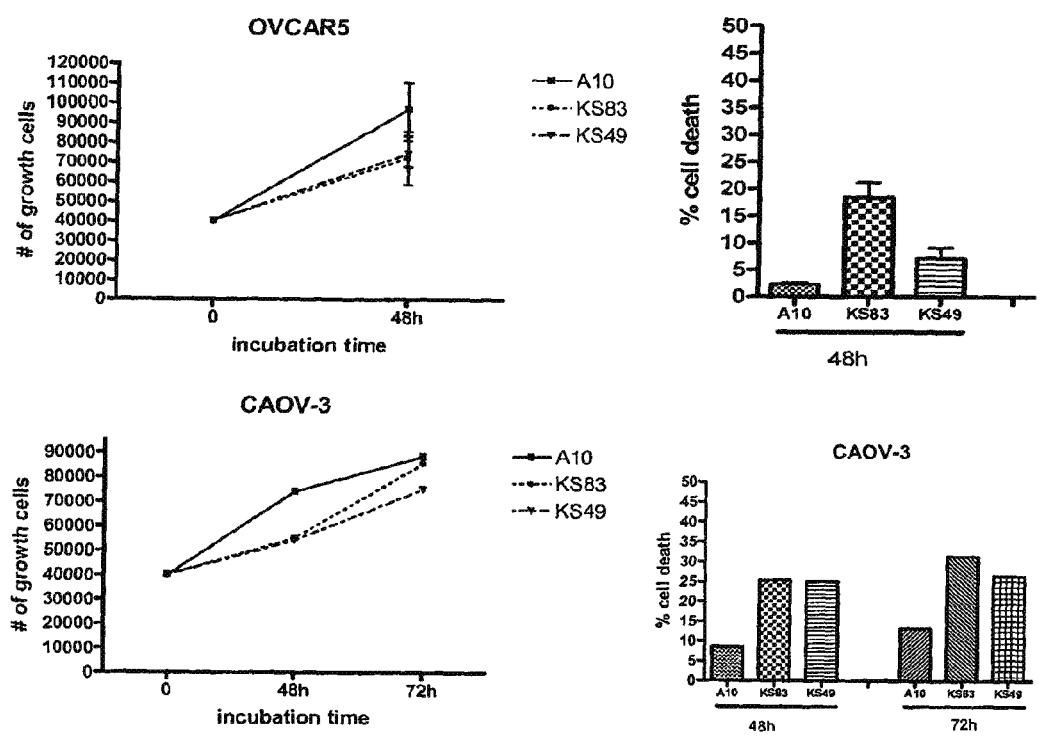
FIG. 21. Four different human ovarian cancer cell lines (OVCAr5, CAOV-3, OVCA 432, OVCA433) were cultured for 48 or 72 hours with 20 microgram/mL diabody in RPMI1640 plus fetal calf serum (10%). 40,000 cells were plated at time zero per well, and the number of viable cells were counted at each of these times. In addition, the percentage of dead cells was scored by trypan blue exclusion. A10, negative control diabody; KS49 and KS83, anti-EMP2 diabodies.
Figure 22:
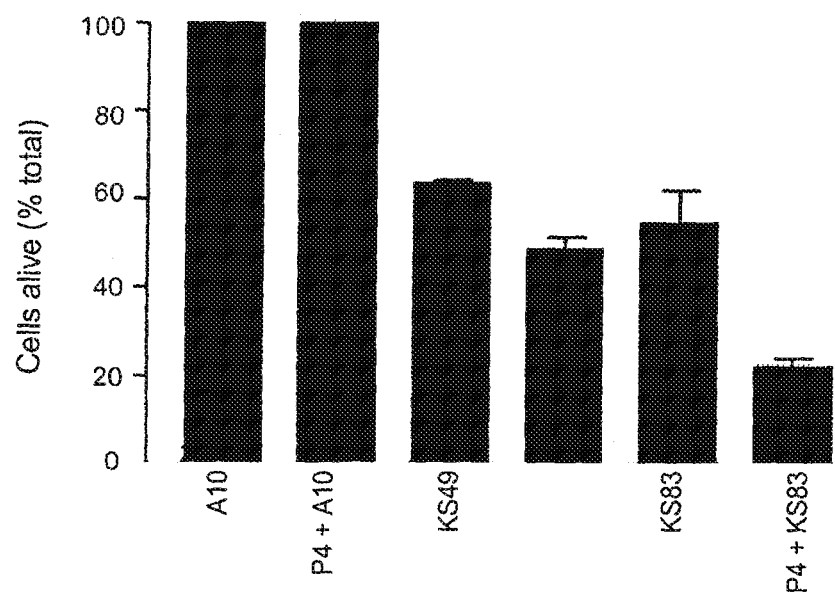
FIG. 22. The human glioblastoma cell line ES was cultured for 72 hours with 20 microgram/mL diabody, with or without progesterone (P4), in RPMI1640 plus fetal calf serum (10%). The percentage of viable cells was scored by trypan blue exclusion, and results from triplicate groups were presented as mean±SEM. A10, negative control diabody; KS49 and KS83, anti-EMP2 diabodies.
Figure 23:
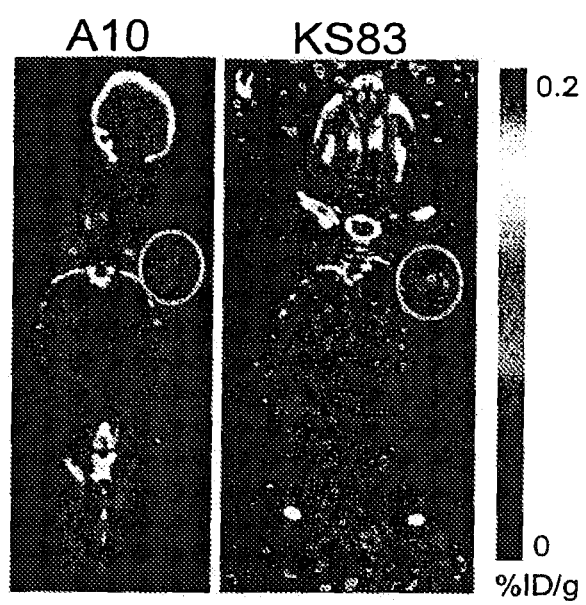
FIG. 23. Nude mice were subcutaneously inoculated with Hec1a (human endometrial carcinoma). When tumor formation reached ~1 cm, mice were intravenously administered with [124]iodine-diabody (25 micrograms, 100 microcuries). 72 hours after administration of diabody, mice were imaged with microPET and CT. A10, negative control diabody; KS83, anti-EMP2 diabody.

To confirm that combination progesterone and EMP2 specific diabodies increase cell death over diabody treatment alone, cells were analyzed by trypan blue exclusion 72 hours after treatment (FIG. 19B). Progesterone and KS83 or KS49 significantly increased cell death over progesterone and control diabody A10 treatment ($p<0.01$ and $p<0.04$; FIG. 20B). Moreover, progesterone significantly increased KS83 diabody treatment by 19.1±3% over KS83 treatment alone ($p<0.05$). Although not significant, progesterone also increased KS49 mediated cell death by 8.1±3% over KS49 treatment alone ($p=0.07$).

The annexin V and propidium iodide staining suggested that anti-EMP2 diabodies induced an apoptotic mode of cell death in RL95-2 cells. To validate this effect, cells were treated with 12.5 µg/ml of the EMP2 specific diabodies KS83 and KS49 or control diabody A10 in the presence or absence of progesterone for 24-36 hours. EMP2 and active caspase 3 was measured in equivalent cell lysates by western blot analysis (FIG. 19C). As expected, progesterone treatment augmented EMP2 expression by approximately 2.5 fold (FIG. 19C, left). Strikingly, significant differences in cleaved caspase 3 was detected upon addition of KS83 compared to the control diabody A10 ($p<0.05$) (FIGS. 19C and D). Strikingly, significantly higher levels of activated caspase 3 were detected upon addition of progesterone and KS49 and KS83 compared to the control A10 ($p<0.05$; $p<0.01$, respectively). These results suggest that progesterone and KS49 or KS83 act synergistically to induce apoptosis of endometrial cancer cells.

H. In Vivo Tumor Targeting.

In order to evaluate the preclinical efficacy of EMP2 therapy, the toxicity of two anti-EMP2 diabodies (KS49 and KS83), and a control diabody (A10) were assessed for toxicity in wildtype C57BL/6 mice. KS49 and KS83 bind a shared epitope in mouse and human EMP2, and are thus useful for assays for toxicity to normal tissues, as well as therapeutic modeling in xenograft assays. To assess normal tissue toxicity, anti-EMP2 and control diabodies were parenterally administered each two days (ranging up to 9 mg/kg) over two weeks in wildtype mice (C57BL/6). No changes were observed in animal weight, or in serum metabolic analytes for liver function (Table 1). Gross and microscopic examination of tissues also showed no abnormalities (data not shown). Notably, this examination reflected an absence of toxicity in lung and skin, which express high levels of EMP2 (Wang et al., *Blood* 97:3890-5 (2001); Ben et al., *Genomics*, 49:443-7 (1998)). Thus, in this limited analysis, no toxicity was detectable by anti-EMP2 diabody to normal tissues.

TABLE 1

Effect of parenteral diabody. Mice were injected i.v. with sterile saline, control diabody A10, or anti-EMP2 diabodies (K83 or K49) biweekly for 14 days.

| | Starting Weight | Final Weight | Direct Bilirubin (mg/dL) | Total Bilirubin (mg/dL) | ALT (U/L) |
|---|---|---|---|---|---|
| Vehicle Control | 19.9 ± 0.7 | 19.8 ± 0.4 | 0 | 0.2 | 45 ± 6 |
| A10 | 18.7 ± 0.2 | 19.5 ± 1.7 | 0 | 0.2 | 36 ± 8 |
| K83 | 18.9 ± 0.9 | 19.8 ± 0.9 | 0 | 0.2 | 44 ± 8 |
| K49 | 19.9 ± 1.4 | 20.3 ± 0.1 | 0 | 0.2 | 37 ± 7 |

3 mice were utilized per group. Mouse weights were determined at the starting and final day, and serum analytes were determined from blood obtained on the final day.

In order to evaluate the efficacy of anti-EMP2 diabodies in vivo, an endometrial cancer xenograft model was created. Tumors from HEC-1A/V and HEC-1A/OE cells were established in the shoulder flanks of female BALB/c nude mice. After detectable tumor formation (day 13), anti-EMP2 diabody KS83, control A10, or a vehicle control (sterile saline) were injected biweekly intra-tumorally, and progression of tumor size was measured by calipers. By day 30, KS83 had profoundly inhibited tumor growth of both HEC-1A/V and HEC-1A/OE tumors (FIG. 20A).

Tumors were excised on day 30. Interestingly, in vivo, both HEC-1A/V and HEC-1A/OE tumors revealed high, comparable levels of EMP2 expression (FIG. 20B). In tumors from both cell types, high levels of EMP2 were observed within the cytoplasm as well as on the membrane. Moreover, excised tumors revealed greater than 4-fold differences in tumor size between KS83 and A10 treatment in HEC-1A/V cells and HEC-1A/OE cells (FIG. 19C, D). Within HEC-1A/V tumors, hemotoxylin and eosin staining revealed large areas of necrosis in tumors treated with KS83 but not with A10 (FIG. 20C). Necrosis was more pronounced in KS83 treated HEC-1A/V than HEC-1A/OE tumors, perhaps as the result of clearance by immune cells (FIG. 20D).

In conclusion, treatment of endometrial adenocarcinoma cells with an highly specific anti-EMP2 diabody resulted in a significant increase in caspase-dependent apoptotic cell death in vitro and a reduction in tumor volume in vivo. These data support EMP2 as a therapeutic target and the use of anti-EMP2 antibodies in the treatment of cancers which express or overexpress EMP2.

Each publication, patent application, patent, and other reference cited herein is incorporated by reference in its entirety to the extent that it is not inconsistent with the present disclosure. In particular, all publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A method for treating cancer in a subject the method comprising the administration of an antibody that binds to Epithelial Membrane Protein 2 (EMP2) wherein the antibody is an isolated antibody that competes for binding to the extracellular loop of human Epithelial Membrane Protein 2 (EMP2) (SEQ ID NO: 42) with an EMP2 inhibitor, wherein the antibody comprises a heavy chain variable region and a light chain variable region, wherein the heavy chain variable region comprises three heavy chain complementary determining regions (HCDRs) and wherein the light chain variable region comprises three light chain variable regions (LCDRs), wherein:

the sequence of HCDR1 is SEQ ID NO: 15,
the sequence of HCDR2 is SEQ ID NO: 17,
the sequence of HCDR3 is SEQ ID NO: 41,
the sequence of LCDR1 is SEQ ID NO: 20,
the sequence of LCDR2 is SEQ ID NO: 23, and
the sequence of LCDR3 is SEQ ID NO: 40.

2. The method of claim 1, wherein the cancer is selected from the group consisting of endometrial cancer, ovarian cancer, glioblastoma, breast cancer, prostate cancer, testicular cancer and myeloma.

3. The method of claim 2, wherein the cancer is endometrial cancer.

4. A method for treating cancer in a subject the method comprising the administration of an antibody that binds to Epithelial Membrane Protein 2 (EMP2) wherein the antibody is an isolated antibody which binds to Epithelial Membrane Protein 2 (EMP2), wherein the antibody comprises a heavy chain variable region and a light chain variable region, wherein the heavy chain variable region comprises three heavy chain complementary determining regions (HCDRs) and wherein the light chain variable region comprises three light chain complementary determining regions (LCDRs), wherein:

the sequence of HCDR1 is SEQ ID NO: 15,
the sequence of HCDR2 is SEQ ID NO: 17,
the sequence of HCDR3 is SEQ ID NO: 41,
the sequence of LCDR1 is SEQ ID NO: 20,
the sequence of LCDR2 is SEQ ID NO: 23, and
the sequence of LCDR3 is SEQ ID NO: 40.

5. The method of claim 4, wherein the cancer is selected from the group consisting of endometrial cancer, ovarian cancer, glioblastoma, breast cancer, prostate cancer, testicular cancer and myeloma.

6. The method of claim 5, wherein the cancer is endometrial cancer.

* * * * *

```
                        SEQUENCE LISTING

<160> NUMBER OF SEQ ID NOS: 44

<210> SEQ ID NO 1
<211> LENGTH: 167
<212> TYPE: PRT
<213> ORGANISM: Homo sapiens

<400> SEQUENCE: 1

Met Leu Val Leu Leu Ala Phe Ile Ile Ala Phe His Ile Thr Ser Ala
1               5                   10                  15

Ala Leu Leu Phe Ile Ala Thr Val Asp Asn Ala Trp Trp Val Gly Asp
                20                  25                  30

Glu Phe Phe Ala Asp Val Trp Arg Ile Cys Thr Asn Asn Thr Asn Cys
            35                  40                  45

Thr Val Ile Asn Asp Ser Phe Gln Glu Tyr Ser Thr Leu Gln Ala Val
        50                  55                  60

Gln Ala Thr Met Ile Leu Ser Thr Ile Leu Cys Cys Ile Ala Phe Phe
65                  70                  75                  80

Ile Phe Val Leu Gln Leu Phe Arg Leu Lys Gln Gly Glu Arg Phe Val
                85                  90                  95

Leu Thr Ser Ile Ile Gln Leu Met Ser Cys Leu Cys Val Met Ile Ala
            100                 105                 110

Ala Ser Ile Tyr Thr Asp Arg Arg Glu Asp Ile His Asp Lys Asn Ala
        115                 120                 125

Lys Phe Tyr Pro Val Thr Arg Glu Gly Ser Tyr Gly Tyr Ser Tyr Ile
    130                 135                 140

Leu Ala Trp Val Ala Phe Ala Cys Thr Phe Ile Ser Gly Met Met Tyr
145                 150                 155                 160

Leu Ile Leu Arg Lys Arg Lys
                165

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: synthetic
      second extracellular loop of human EMP2

<400> SEQUENCE: 2
```

Glu Asp Ile His Asp Lys Asn Ala Lys Phe Tyr Pro Val Thr Arg Glu
1               5                   10                  15

Gly Ser Tyr Gly
            20

<210> SEQ ID NO 3
<211> LENGTH: 1484
<212> TYPE: DNA
<213> ORGANISM: Homo sapiens

<400> SEQUENCE: 3

```
gaggggcccc gccgcctaga gggtggaggg agggcgcgca gtcccagccc agagcttcaa      60
aacagcccgg cggcctcgcc tcgcacccccc agccagtccg tcgatccagc tgccagcgca    120
gccgccagcg ccggcacatc ccgctctggg ctttaaacgt gaccccctcgc ctcgactcgc    180
cctgccctgt gaaatgttg gtgcttcttg ctttcatcat cgccttccac atcacctctg      240
cagccttgct gttcattgcc accgtcgaca atgcctggtg ggtaggagat gagtttttg      300
cagatgtctg gagaatatgt accaacaaca cgaattgcac agtcatcaat gacagctttc    360
aagagtactc cacgctgcag gcggtccagg ccaccatgat cctctccacc attctctgct    420
gcatcgcctt cttcatcttc gtgctccagc tcttccgcct gaagcaggga gagaggtttg    480
tcctaacctc catcatccag ctaatgtcat gtctgtgtgt catgattgcg gcctccattt    540
atacagacag gcgtgaagac attcacgaca aaaacgcgaa attctatccc gtgaccagag    600
aaggcagcta cggctactcc tacatcctgg cgtgggtggc cttcgcctgc accttcatca    660
gcggcatgat gtacctgata ctgaggaagc gcaaatagag ttccggagct gggttgcttc    720
tgctgcagta cagaatccac attcagataa ccattttgta tataatcatt attttttgag    780
gttttctag caaacgtatt gtttccttta aaagccaaaa aaaaaaaaaa aaaaaaaaa      840
aaaaaaaaa aaaaaaaaaa aatccaaaag agagaagagt ttttgcattc ttgagatcag    900
agaatagact atgaaggctg gtattcagaa ctgctgccca ctcaaaagtc tcaacaagac    960
acaagcaaaa atccagcaat gctcaaatcc aaaagcactc ggcaggacat ttcttaacca  1020
tgggggctgtg atggaggag aggagaggct gggaaagccg ggtctctggg gacgtgcttc    1080
ctatgggttt cagctggccc aagcccctcc cgaatctctc tgctagtggt gggtggaaga    1140
gggtgaggtg gggtatagga gaagaatgac agcttcctga gaggtttcac ccaagttcca    1200
agtgagaagc aggtgtagtc cctggcattc tgtctgtatc caaaccagag cccagccatc    1260
cctccggtat tgggggtgggt cagaaaaagt ctcacctcaa tttgccgaca gtgtcacctg  1320
cttgccttag aatggtcat ccttaacctg cgtgccagat ttagactcgt ctttaggcaa    1380
aacctacagc gccccccccct caccccagac ctacagaatc agagtcttca agggatgggg  1440
ccagggaatc tgcatttcta atgcgctccc tgggcaacgc ttca                    1484
```

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence:synthetic
      linker between VL and VH of chimeric antibody

<400> SEQUENCE: 4

Gly Ser Thr Ser Gly Gly Gly Ser Gly Gly Gly Ser Gly Gly Gly Gly
1               5                   10                  15

Ser Ser

<210> SEQ ID NO 5
<211> LENGTH: 167
<212> TYPE: PRT
<213> ORGANISM: Artificial Sequence
<220> FEATURE:
<223> OTHER INFORMATION: Description of Artificial Sequence:synthetic
      EMP2 sequence

<400> SEQUENCE: 5

```
Met Leu Val Ile Leu Ala Phe Ile Ile Val Phe His Ile Val Ser Thr
1               5                   10                  15

Ala Phe Ile Ser Thr Ile Asp Asn Ala Trp Ile Val Gly Asp Ser Ala
            20                  25                  30

Asp Leu Arg Val Cys Thr Asn Ser Thr Leu Cys Thr Glu Ile Asn Glu
        35                  40                  45

Leu Thr Gly Pro Glu Ala Phe Glu Gly Tyr Ser Val Trp Gln Ala Val
    50                  55                  60

Gln Ala Thr Met Ile Thr Ile Leu Ser Ser Leu Cys Ile Ser Phe Leu
65                  70                  75                  80

Ile Phe Leu Leu Gln Leu Phe Arg Leu Lys Gln Gly Glu Arg Phe Val
                85                  90                  95

Leu Thr Ser Ile Ile Gln Leu Met Ser Cys Leu Cys Val Met Ile Gly
            100                 105                 110

Ala Ser Ile Tyr Thr Asp Arg Arg Gln Asp Leu His Gln Gln Asn Arg
        115                 120                 125

Lys Leu Tyr Tyr Leu Leu Gln Gln Gly Ser Tyr Gly Tyr Ser Phe Ile
    130                 135                 140

Leu Ala Trp Val Ala Phe Ala Phe Thr Phe Ile Ser Gly Leu Met Tyr
145                 150                 155                 160

Met Ile Leu Arg Lys Arg Lys
                165
```

<210> SEQ ID NO 6
<211> LENGTH: 123
<212> TYPE: PRT
<213> ORGANISM: Artificial Sequence
<220> FEATURE:
<223> OTHER INFORMATION: Description of Artificial Sequence:synthetic
      human anti-EMP2 antibody KS49 heavy chain variable region

<400> SEQUENCE: 6

```
Met Ala Gln Val Gln Leu Val Gln Ser Gly Gly Gly Val Gln Pro
1               5                   10                  15

Gly Arg Ser Leu Arg Leu Ser Cys Ala Ala Ser Gly Phe Thr Phe Ser
            20                  25                  30

Ser Tyr Ala Met His Trp Val Arg Gln Ala Pro Gly Lys Gly Leu Glu
        35                  40                  45

Trp Val Ala Val Ile Ser Tyr Asp Gly Ser Asn Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Arg Gly Arg Lys Ser Ala Gly Ile Asp Tyr
            100                 105                 110

Trp Gly Gln Gly Thr Leu Val Thr Val Ser Ser
```

<210> SEQ ID NO 7
<211> LENGTH: 124
<212> TYPE: PRT
<213> ORGANISM: Artificial Sequence
<220> FEATURE:
<223> OTHER INFORMATION: Description of Artificial Sequence:synthetic
      human anti-EMP2 antibody KS49 light chain variable region

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Gly Trp Thr
                85                  90                  95

Phe Gly Gln Gly Thr Lys Val Asp Ile Lys Arg Ala Ala Ala Glu Gln
            100                 105                 110

Lys Leu Ile Ser Glu Glu Asp Leu Asn Gly Ala Ala
115                 120

<210> SEQ ID NO 8
<211> LENGTH: 122
<212> TYPE: PRT
<213> ORGANISM: Artificial Sequence
<220> FEATURE:
<223> OTHER INFORMATION: Description of Artificial Sequence:synthetic
      human anti-EMP2 antibody KS83 heavy chain variable region

<400> SEQUENCE: 8

Met Ala Gln Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met His Trp Val Arg Gln Ala Pro Gly Lys Gly Leu Glu
        35                  40                  45

Trp Val Ala Val Ile Ser Tyr Asp Gly Ser Asn Lys Tyr Tyr Ala Asp
50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Thr Val Gly Ala Thr Gly Ala Phe Asp Ile Trp Gly
            100                 105                 110

Gln Gly Thr Met Val Thr Val Ser Ser Ser
        115                 120

<210> SEQ ID NO 9
<211> LENGTH: 125
<212> TYPE: PRT
<213> ORGANISM: Artificial Sequence
<220> FEATURE:
<223> OTHER INFORMATION: Description of Artificial Sequence: synthetic human anti-EMP2 antibody KS83 light chain variable region

<400> SEQUENCE: 9

Asp Ile Val Met Thr Gln Ser Pro Ser Thr Val Ser Ala Ser Val Gly
1               5                   10                  15

Asp Arg Val Ile Ile Pro Cys Arg Ala Ser Gln Ser Ile Gly Lys Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Gly Trp Val Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Ser Ala Thr Tyr Val Cys Gln Gln Ser His Asn Phe Pro Pro
                85                  90                  95

Thr Phe Gly Gly Gly Thr Lys Leu Glu Ile Lys Arg Ala Ala Ala Glu
            100                 105                 110

Gln Lys Leu Ile Ser Glu Glu Asp Leu Asn Gly Ala Ala
        115                 120                 125

<210> SEQ ID NO 10
<211> LENGTH: 119
<212> TYPE: PRT
<213> ORGANISM: Artificial Sequence
<220> FEATURE:
<223> OTHER INFORMATION: Description of Artificial Sequence: synthetic
      human anti-EMP2 antibody KS41 heavy chain variable region

<400> SEQUENCE: 10

Met Ala Gln Val Gln Leu Val Gln Ser Gly Gly Gly Leu Val Gln Pro
1               5                   10                  15

Gly Arg Ser Leu Arg Leu Ser Cys Ala Ala Ser Gly Phe Ser Phe Ser
            20                  25                  30

Glu Tyr Pro Met His Trp Val Arg Gln Ala Pro Gly Arg Gly Leu Glu
        35                  40                  45

Ser Val Ala Val Ile Ser Tyr Asp Gly Glu Tyr Gln Lys Tyr Ala Asp
    50                  55                  60

Ser Val Lys Gly Arg Phe Thr Ile Ser Arg Asp Asp Ser Lys Ser Thr
65                  70                  75                  80

Val Tyr Leu Gln Met Asn Ser Leu Arg Pro Glu Asp Thr Ala Val Tyr
                85                  90                  95

Tyr Cys Ala Arg Thr Ile Asn Asn Gly Met Asp Val Trp Gly Gln Gly
            100                 105                 110

Thr Thr Val Thr Val Ser Ser
        115

<210> SEQ ID NO 11
<211> LENGTH: 124
<212> TYPE: PRT
<213> ORGANISM: Artificial Sequence
<220> FEATURE:
<223> OTHER INFORMATION: Description of Artificial Sequence:synthetic
      human anti-EMP2 antibody KS41 light chain variable region

<400> SEQUENCE: 11

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

```
Leu Gly Trp Tyr Gln Gln Lys Pro Gly Lys Ala Pro Glu Leu Leu Ile
            35                  40                  45

Tyr Gly Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Leu Gln Asp Tyr Asn Gly Trp Thr
                85                  90                  95

Phe Gly Gln Gly Thr Lys Leu Glu Ile Lys Arg Ala Ala Ala Glu Gln
            100                 105                 110

Lys Leu Ile Ser Glu Glu Asp Leu Asn Gly Ala Ala
        115                 120
```

<210> SEQ ID NO 12
<211> LENGTH: 119
<212> TYPE: PRT
<213> ORGANISM: Artificial Sequence
<220> FEATURE:
<223> OTHER INFORMATION: Description of Artificial Sequence: synthetic
      human anti-EMP2 antibody KS89 heavy chain variable region

<400> SEQUENCE: 12

```
Met Ala Gln Val Gln Leu Val Gln Ser Gly Gly Gly Leu Val Gln Pro
1               5                   10                  15

Gly Arg Ser Leu Arg Leu Ser Cys Ala Ala Ser Gly Phe Ser Phe Ser
            20                  25                  30

Glu Tyr Pro Met His Trp Val Arg Gln Ala Pro Gly Arg Gly Leu Glu
        35                  40                  45

Ser Val Ala Val Ile Ser Tyr Asp Gly Glu Tyr Gln Lys Tyr Ala Asp
    50                  55                  60

Ser Val Lys Gly Arg Phe Thr Ile Ser Arg Asp Asp Ser Lys Ser Thr
65                  70                  75                  80

Val Tyr Leu Gln Met Asn Ser Leu Arg Pro Glu Asp Thr Ala Val Tyr
                85                  90                  95

Tyr Cys Ala Arg Thr Ile Asn Asn Gly Met Asp Val Trp Gly Gln Gly
            100                 105                 110

Thr Thr Val Thr Val Ser Ser
        115
```

<210> SEQ ID NO 13
<211> LENGTH: 124
<212> TYPE: PRT
<213> ORGANISM: Artificial Sequence
<220> FEATURE:
<223> OTHER INFORMATION: Description of Artificial Sequence: synthetic
      human anti-EMP2 antibody KS89 light chain variable region

<400> SEQUENCE: 13

```
Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Glu Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Ser Ala Thr Tyr Tyr Cys Leu Gln Asp Tyr Asn Gly Trp Thr
                85                  90                  95

Phe Gly Gln Gly Thr Lys Leu Glu Ile Lys Arg Ala Ala Ala Glu Gln
            100                 105                 110

Lys Leu Ile Ser Glu Glu Asp Leu Asn Gly Ala Ala
        115                 120

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence:synthetic
      human anti-EMP2 antibody KS49 and KS83 heavy chain variable region
      CDR 1 Heavy (CDR-H1)

<400> SEQUENCE: 14

Ser Tyr Ala Met His
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: synthetic
      human anti-EMP2 antibody KS41 and KS89 heavy chain variable region
      CDR 1 Heavy (CDR-H1

<400> SEQUENCE: 15

Glu Tyr Pro Met His
1               5

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: synthetic
      human anti-EMP2 antibody KS49 and KS83 heavy chain variable region
      CDR 2 Heavy (CDR-H2)

<400> SEQUENCE: 16

Val Ile Ser Tyr Asp Gly Ser Asn Lys Tyr Tyr Ala Asp Ser Val Lys
1               5                   10                  15

Gly

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: synthetic
      human anti-EMP2 antibody KS41 and KS89 heavy chain variable region
      CDR 2 Heavy (CDR-H2)

<400> SEQUENCE: 17

Val Ile Ser Tyr Asp Gly Glu Tyr Gln Lys Tyr Ala Asp Ser Val Lys
1               5                   10                  15

Gly

<210> SEQ ID NO 18
<211> LENGTH: 11
<212> TYPE: PRT
<213> ORGANISM: Artificial Sequence
```

```
<220> FEATURE:
<223> OTHER INFORMATION: Description of Artificial Sequence: synthetic
      human anti-EMP2 antibody KS49 light chain variable region CDR 1
      Light (CDR-L1)

<400> SEQUENCE: 18

Gln Ala Ser Gln Asp Ile Ser Asn Tyr Leu Asn
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: synthetic
      human anti-EMP2 antibody KS83 light chain variable region CDR 1
      Light (CDR-L1)

<400> SEQUENCE: 19

Arg Ala Ser Gln Ser Ile Gly Lys Trp Leu Ala
1               5                   10

<210> SEQ ID NO 20
<211> LENGTH: 11
<212> TYPE: PRT
<213> ORGANISM: Artificial Sequence
<220> FEATURE:
<223> OTHER INFORMATION: synthetic human anti-EMP2 antibody KS41 and
      KS89 light chain variable region CDR 1 Light (CDR-L1)

<400> SEQUENCE: 20

Arg Ala Ser Gln Gly Ile Arg Asn Asp Leu Gly
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: synthetic
      human anti-EMP2 antibody KS49 light chain variable region CDR 2
      Light (CDR-L2)

<400> SEQUENCE: 21

Ala Ala Ser Ser Leu Gln Ser
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence:s ynthetic
      human anti-EMP2 antibody KS83 light chain variable region CDR 2
      Light (CDR-L2)

<400> SEQUENCE: 22

Lys Ala Ser Ser Leu Glu Gly
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: synthetic
      human anti-EMP2 antibody KS41 and KS89 light chain variable
      region CDR 2 Light (CDR-L2)
```

<400> SEQUENCE: 23

Gly Ala Ser Ser Leu Gln Ser
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence:synthetic
      short linker joining VH and VL domain

<400> SEQUENCE: 24

Ser Gly Gly Gly Ser
1               5

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: synthetic
      PCR forward primer for cloning EMP2

<400> SEQUENCE: 25
cgcggatcct ctaccattga caatgcctgg                                      30

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: synthetic
      PCR reverse primer for cloning EMP2

<400> SEQUENCE: 26
ccggaattct tacgcctgca tcacagaata acc                                  33

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence:synthetic
      4 amino acid long linker for biotinylation of scFv C- and
      N-termini

<400> SEQUENCE: 27

Gly Ser Gly Ser
1

<210> SEQ ID NO 28
<211> LENGTH: 24
<212> TYPE: PRT
<213> ORGANISM: Artificial Sequence
<220> FEATURE:
<223> OTHER INFORMATION: Description of Artificial Sequence: synthetic
      human EMP2 extracellular loop

<400> SEQUENCE: 28

Asp Ile His Asp Lys Asn Ala Lys Phe Tyr Pro Val Thr Arg Glu Gly
1               5                   10                  15

Ser Thr Gly Gly Ser Gly Ser Lys
            20

<210> SEQ ID NO 29

```
<211> LENGTH: 24
<212> TYPE: PRT
<213> ORGANISM: Artificial Sequence
<220> FEATURE:
<223> OTHER INFORMATION: Description of Artificial Sequence: synthetic
      mouse EMP2 extracellular loop

<400> SEQUENCE: 29

Asp Leu His Gln Gln Asn Arg Lys Leu Tyr Tyr Leu Leu Gln Glu Gly
1               5                   10                  15

Ser Tyr Gly Gly Ser Gly Ser Lys
            20

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: synthetic
      6 His scFv C-terminus tag

<400> SEQUENCE: 30

His His His His His His
1               5

<210> SEQ ID NO 31
<211> LENGTH: 48
<212> TYPE: DNA
<213> ORGANISM: Artificial Sequence
<220> FEATURE:
<223> OTHER INFORMATION: Description of Artificial Sequence: synthetic
      15 amino acid linker region to convert scFv fragments into diabody

<400> SEQUENCE: 31
agtggtggag gcggttcagg cggaggtggc tctggcggtg gcggatcg                    48

<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence: synthetic
      shortened 5 amino acid linker region to convert scFv fragments
      into diabody

<400> SEQUENCE: 32
agtggtggag gatcg                                                        15

<210> SEQ ID NO 33
<211> LENGTH: 257
<212> TYPE: PRT
<213> ORGANISM: Artificial Sequence
<220> FEATURE:
<223> OTHER INFORMATION: Description of Artificial Sequence: synthetic
      KS49 anti-EMP2 diabody

<400> SEQUENCE: 33

Met Ala Gln Val Gln Leu Val Gln Ser Gly Gly Val Val Gln Pro
1               5                   10                  15

Gly Arg Ser Leu Arg Leu Ser Cys Ala Ala Ser Gly Phe Thr Phe Ser
            20                  25                  30

Ser Tyr Ala Met His Trp Val Arg Gln Ala Pro Gly Lys Gly Leu Glu
        35                  40                  45

Trp Val Ala Val Ile Ser Tyr Asp Gly Ser Asn Lys Tyr Tyr Ala Asp
    50                  55                  60
```

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Asp Arg Gly Arg Lys Ser Ala Gly Ile Asp Tyr
                100                 105                 110

Trp Gly Gln Gly Thr Leu Val Thr Val Ser Gly Gly Gly Ser Asp
            115                 120                 125

Ile Gln Met Thr Gln Ser Pro Ser Ser Leu Ser Ala Ser Val Gly Asp
        130                 135                 140

Arg Val Thr Ile Thr Cys Gln Ala Ser Gln Asp Ile Ser Asn Tyr Leu
145                 150                 155                 160

Asn Trp Tyr Gln Gln Lys Pro Gly Lys Ala Pro Lys Leu Leu Ile Tyr
                165                 170                 175

Ala Ala Ser Ser Leu Gln Ser Gly Val Pro Ser Arg Phe Ser Gly Ser
            180                 185                 190

Gly Ser Gly Thr Asp Phe Thr Leu Thr Ile Ser Ser Leu Gln Pro Glu
        195                 200                 205

Asp Phe Ala Thr Tyr Tyr Cys Leu Gln Asp Tyr Asn Gly Trp Thr Phe
        210                 215                 220

Gly Gln Gly Thr Lys Val Asp Ile Lys Arg Ala Ala Ala Glu Gln Lys
225                 230                 235                 240

Leu Ile Ser Glu Glu Asp Leu Asn Gly Ala Ala His His His His His
                245                 250                 255

His

<210> SEQ ID NO 34
<211> LENGTH: 257
<212> TYPE: PRT
<213> ORGANISM: Artificial Sequence
<220> FEATURE:
<223> OTHER INFORMATION: Description of Artificial Sequence: synthetic
      KS83 anti-EMP2 diabody

<400> SEQUENCE: 34

Met Ala Gln Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met His Trp Val Arg Gln Ala Pro Gly Lys Gly Leu Glu
        35                  40                  45

Trp Val Ala Val Ile Ser Tyr Asp Gly Ser Asn Lys Tyr Tyr Ala Asp
    50                  55                  60

Ser Val Lys Gly Arg Phe Thr Ile Ser Arg Asp Asn Ser Lys Asn Thr
 65                 70                  75                  80

Leu Tyr Leu Gln Met Asn Ser Leu Arg Ala Glu Asp Thr Ala Val Tyr
                85                  90                  95

Tyr Cys Ala Arg Thr Val Gly Ala Thr Gly Ala Phe Asp Ile Trp Gly
                100                 105                 110

Gln Gly Thr Met Val Thr Val Ser Ser Gly Gly Gly Ser Asp Ile
            115                 120                 125

Val Met Thr Gln Ser Pro Ser Thr Val Ser Ala Ser Val Gly Asp Arg
        130                 135                 140

Val Ile Ile Pro Cys Arg Ala Ser Gln Ser Ile Gly Lys Trp Leu Ala
145                 150                 155                 160

Trp Tyr Gln Gln Lys Pro Gly Lys Ala Pro Lys Leu Leu Ile Tyr Lys
                165                 170                 175

Ala Ser Ser Leu Glu Gly Trp Val Pro Ser Arg Phe Ser Gly Ser Gly
            180                 185                 190

Ser Gly Thr Glu Phe Ser Leu Thr Ile Ser Ser Leu Gln Pro Asp Asp
        195                 200                 205

Ser Ala Thr Tyr Val Cys Gln Gln Ser His Asn Phe Pro Pro Thr Phe
    210                 215                 220

Gly Gly Gly Thr Lys Leu Glu Ile Lys Arg Ala Ala Glu Gln Lys
225                 230                 235                 240

Leu Ile Ser Glu Glu Asp Leu Asn Gly Ala Ala His His His His
                245                 250                 255

His

<210> SEQ ID NO 35
<211> LENGTH: 254
<212> TYPE: PRT
<213> ORGANISM: Artificial Sequence
<220> FEATURE:
<223> OTHER INFORMATION: Description of Artificial Sequence: synthetic
      KS41 anti-EMP2 diabody

<400> SEQUENCE: 35

Met Ala Gln Val Gln Leu Val Gln Ser Gly Gly Gly Leu Val Gln Pro
1               5                   10                  15

Gly Arg Ser Leu Arg Leu Ser Cys Ala Ala Ser Gly Phe Ser Phe Ser
            20                  25                  30

Glu Tyr Pro Met His Trp Val Arg Gln Ala Pro Gly Arg Gly Leu Glu
        35                  40                  45

Ser Val Ala Val Ile Ser Tyr Asp Gly Glu Tyr Gln Lys Tyr Ala Asp
    50                  55                  60

Ser Val Lys Gly Arg Phe Thr Ile Ser Arg Asp Asp Ser Lys Ser Thr
65                  70                  75                  80

Val Tyr Leu Gln Met Asn Ser Leu Arg Pro Glu Asp Thr Ala Val Tyr
                85                  90                  95

Tyr Cys Ala Arg Thr Ile Asn Asn Gly Met Asp Val Trp Gly Gln Gly
            100                 105                 110

Thr Thr Val Thr Val Ser Ser Ser Gly Gly Gly Ser Asp Ile Val Met
        115                 120                 125

Thr Gln Ser Pro Ser Ser Leu Ser Ala Ser Val Gly Asp Arg Val Thr
    130                 135                 140

Ile Thr Cys Arg Ala Ser Gln Gly Ile Arg Asn Asp Leu Gly Trp Tyr
145                 150                 155                 160

Gln Gln Lys Pro Gly Lys Ala Pro Glu Leu Leu Ile Tyr Gly Ala Ser
                165                 170                 175

Ser Leu Gln Ser Gly Val Pro Ser Arg Phe Ser Gly Ser Gly Ser Gly
            180                 185                 190

Thr Asp Phe Thr Leu Thr Ile Ser Ser Leu Gln Pro Glu Asp Ser Ala
        195                 200                 205

Thr Tyr Tyr Cys Leu Gln Asp Tyr Asn Gly Trp Thr Phe Gly Gln Gly
    210                 215                 220

Thr Lys Leu Glu Ile Lys Arg Ala Ala Ala Glu Gln Lys Leu Ile Ser
225                 230                 235                 240

Glu Glu Asp Leu Asn Gly Ala Ala His His His His His
                245                 250

<210> SEQ ID NO 36
<211> LENGTH: 257
<212> TYPE: PRT
<213> ORGANISM: Artificial Sequence
<220> FEATURE:
<223> OTHER INFORMATION: Description of Artificial Sequence: synthetic
      KS89 anti-EMP2 diabody

<400> SEQUENCE: 36

Met Ala Gln Val Gln Leu Val Gln Ser Gly Gly Gly Leu Val Gln Pro
1               5                   10                  15

Gly Arg Ser Leu Arg Leu Ser Cys Ala Ala Ser Gly Phe Ser Phe Ser
            20                  25                  30

Glu Tyr Pro Met Thr His Trp Val Arg Gln Ala Pro Gly Arg Gly Leu
        35                  40                  45

Glu Ser Val Ala Val Ile Ser Tyr Asp Gly Glu Tyr Gln Lys Tyr Ala
    50                  55                  60

Asp Ser Val Lys Gly Arg Phe Thr Ile Ser Arg Asp Ser Lys Ser
65                  70                  75                  80

Thr Val Tyr Leu Gln Met Asn Ser Leu Arg Pro Glu Asp Thr Ala Val
                85                  90                  95

Tyr Tyr Cys Ala Arg Thr Ile Asn Asn Gly Met Asp Val Trp Gly Gln
            100                 105                 110

Gly Thr Thr Val Thr Val Ser Ser Gly Gly Gly Ser Asp Ile Val
            115                 120                 125

Met Glu Thr Thr Gln Ser Pro Ser Ser Leu Ser Ala Ser Val Gly Asp
130                 135                 140

Arg Val Thr Ile Thr Cys Arg Ala Ser Gln Gly Ile Arg Asn Asp Leu
145                 150                 155                 160

Gly Trp Tyr Gln Gln Lys Pro Gly Lys Ala Pro Glu Leu Leu Ile Tyr
                165                 170                 175

Gly Ala Ser Ser Leu Gln Ser Gly Val Pro Ser Arg Phe Ser Gly Ser
            180                 185                 190

Gly Ser Gly Thr Asp Phe Thr Leu Thr Ile Ser Ser Leu Gln Pro Glu
        195                 200                 205

Asp Ser Ala Thr Tyr Tyr Cys Leu Gln Asp Tyr Asn Gly Trp Thr Phe
    210                 215                 220

Gly Gln Gly Thr Lys Leu Glu Ile Lys Arg Ala Ala Ala Glu Gln Lys
225                 230                 235                 240

Leu Ile Ser Glu Glu Asp Leu Asn Gly Ala Ala His His His His
                245                 250                 255

His

<210> SEQ ID NO 37
<211> LENGTH: 10
<212> TYPE: PRT
<213> ORGANISM: Artificial Sequence
<220> FEATURE:
<223> OTHER INFORMATION: Description of Aritifical Sequence: synthetic
      human anti-EMP2 antibody KS83 heavy chain variable region CDR 3
      Heavy (CDR-H3)

<400> SEQUENCE: 37

Thr Val Gly Ala Thr Gly Ala Phe Asp Ile
1               5                   10

<210> SEQ ID NO 38
<211> LENGTH: 9

```
<212> TYPE: PRT
<213> ORGANISM: Artificial Sequence
<220> FEATURE:
<223> OTHER INFORMATION: Description of Artificial Sequence: synthetic
      human anti-EMP2 antibody KS83 light chain variable region CDR 3
      Light (CDR-L3)

<400> SEQUENCE: 38

Gln Gln Ser His Asn Phe Pro Pro Thr
1               5

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: synthetic
      human anti-EMP2 antibody KS49 heavy chain variable region CDR 3
      Heavy (CDR-H3)

<400> SEQUENCE: 39

Asp Arg Arg Gly Arg Lys Ser Ala Gly Ile Asp Tyr
1               5                   10

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: synthetic
      human anti-EMP2 antibody KS41, KS49, and KS89 light chain variable
      region CDR 3 Light (CDR-L3)

<400> SEQUENCE: 40

Leu Gln Asp Tyr Asn Gly Trp Thr
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artifical Sequence: synthetic
      human anti-EMP2 antibody KS41 and KS89 heavy chain variable region
      CDR 3 Heavy (CDR-H3)

<400> SEQUENCE: 41

Thr Ile Asn Asn Gly Met Asp Val
1               5

<210> SEQ ID NO 42
<211> LENGTH: 24
<212> TYPE: PRT
<213> ORGANISM: Artificial Sequence
<220> FEATURE:
<223> OTHER INFORMATION: synthetic human EMP2 extracellular loop

<400> SEQUENCE: 42

Asp Ile His Asp Lys Asn Ala Lys Phe Tyr Pro Val Thr Arg Glu Gly
1               5                   10                  15

Ser Tyr Gly Gly Ser Gly Ser Lys
            20

<210> SEQ ID NO 43
<211> LENGTH: 122
```

```
<212> TYPE: PRT
<213> ORGANISM: Artificial Sequence
<220> FEATURE:
<223> OTHER INFORMATION: synthetic human anti-EMP2 antibody KS49 heavy
      chain variable region

<400> SEQUENCE: 43

Met Ala Gln Val Gln Leu Val Gln Ser Gly Gly Val Val Gln Pro
1               5                   10                  15

Gly Arg Ser Leu Arg Leu Ser Cys Ala Ala Ser Gly Phe Thr Phe Ser
            20                  25                  30

Ser Tyr Ala Met His Trp Val Arg Gln Ala Pro Gly Lys Gly Leu Glu
        35                  40                  45

Trp Val Ala Val Ile Ser Tyr Asp Gly Ser Asn Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Arg Gly Arg Lys Ser Ala Gly Ile Asp Tyr
            100                 105                 110

Trp Gly Gln Gly Thr Leu Val Thr Val Ser
            115                 120

<210> SEQ ID NO 44
<211> LENGTH: 121
<212> TYPE: PRT
<213> ORGANISM: Artificial Sequence
<220> FEATURE:
<223> OTHER INFORMATION: synthetic human anti-EMP2 antibody KS83 heavy
      chain variable region

<400> SEQUENCE: 44

Met Ala Gln Val Gln Leu Val Glu Ser Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met His Trp Val Arg Gln Ala Pro Gly Lys Gly Leu Glu
        35                  40                  45

Trp Val Ala Val Ile Ser Tyr Asp Gly Ser Asn Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Thr Val Gly Ala Thr Gly Ala Phe Asp Ile Trp Gly
            100                 105                 110

Gln Gly Thr Met Val Thr Val Ser Ser
            115                 120
```